US008691352B2

(12) United States Patent  (10) Patent No.: US 8,691,352 B2
Makino  (45) Date of Patent: Apr. 8, 2014

(54) POLYMERIZABLE COMPOSITION, COLOR FILTER, AND METHOD OF PRODUCING THE SAME, SOLID-STATE IMAGING DEVICE, AND PLANOGRAPHIC PRINTING PLATE PRECURSOR, AND NOVEL COMPOUND

(75) Inventor: Masaomi Makino, Haibara-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/395,849

(22) PCT Filed: Aug. 10, 2010

(86) PCT No.: PCT/JP2010/063585
§ 371 (c)(1),
(2), (4) Date: Mar. 13, 2012

(87) PCT Pub. No.: WO2011/030645
PCT Pub. Date: Mar. 17, 2011

(65) Prior Publication Data
US 2012/0176571 A1    Jul. 12, 2012

(30) Foreign Application Priority Data
Sep. 14, 2009 (JP) ................... 2009-211931

(51) Int. Cl.
*C09K 19/00* (2006.01)
(52) U.S. Cl.
USPC ........... 428/1.31; 349/106; 430/7; 430/281.1; 430/286.1; 430/916; 430/919; 522/14; 522/28; 522/39; 522/65; 522/68; 544/142; 544/145
(58) Field of Classification Search
USPC ........... 428/1.31; 349/106, 110; 430/7, 270.1, 430/286.1, 281.1, 913, 919, 923, 285.1, 430/284.1, 287.1, 916; 359/491.01; 502/187, 168, 522; 544/142, 145; 522/14, 17, 18, 28, 39, 65, 68, 120, 522/121, 130, 140
See application file for complete search history.

(56) References Cited

U.S. PATENT DOCUMENTS

| 4,255,513 A | 3/1981 | Laridon et al. |
| 4,590,145 A | 5/1986 | Itoh et al. |
| 2007/0048663 A1* | 3/2007 | Sakata ................ 430/270.1 |
| 2009/0246651 A1* | 10/2009 | Fujimori et al. ............ 430/7 |

FOREIGN PATENT DOCUMENTS

| CN | 101082684 A | 12/2007 |
| EP | 1 762 894 A1 | 3/2007 |
| JP | 2000-80068 A | 3/2000 |
| JP | 2001-233842 A | 8/2001 |
| JP | 2005-202252 A | 7/2005 |
| JP | 2005-319758 A | 11/2005 |
| JP | 2006-342166 A | 12/2006 |
| JP | 2007-231000 A | 9/2007 |
| JP | 2008-89713 A | 4/2008 |
| JP | 2008-250074 A | 10/2008 |
| JP | 2009-109921 A | 5/2009 |
| JP | 2009-179619 A | 8/2009 |
| JP | 2009179619 A * | 8/2009 |
| JP | 2010-37223 A | 2/2010 |
| JP | 2010-215575 A | 9/2010 |

OTHER PUBLICATIONS

First Office Action, dated Feb. 4, 2013, issued in corresponding CN Application No. 201080040374.6, 19 pages in English and Chinese.
Extended European Search Report dated Dec. 20, 2013 in European Application No. 10815242.2.
Office Action dated Dec. 3, 2013 in Japanese Application No. 2010-173125.

* cited by examiner

*Primary Examiner* — Gwendolyn Blackwell
*Assistant Examiner* — Ruiyun Zhang
(74) *Attorney, Agent, or Firm* — Sughrue Mion, PLLC

(57) ABSTRACT

Disclosed is a photopolymerizable composition which contains a photopolymerization initiator (A) that has a partial structure represented by the following Formula (1) and a polymerizable compound (B). In General formula (1), $R^3$ and $R^4$ each independently represents a hydrogen atom, an alkyl group, an alkenyl group, an alkynyl group, an aryl group, a heteroaryl group or an alkoxy group; $R^3$ and $R^4$ may form a ring with each other; and X represents $OR^5$, $SR^6$, or $NR^{17}R^{18}$. The photopolymerizable composition is capable of forming a cured film that has high sensitivity, excellent intra-membrane curability and excellent adhesion to a support. The cured film is able to maintain a patterned shape even during post-heating after development and has good pattern formability, while coloring due to heating with passage of time being suppressed.

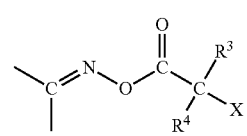

(1)

11 Claims, No Drawings

POLYMERIZABLE COMPOSITION, COLOR FILTER, AND METHOD OF PRODUCING THE SAME, SOLID-STATE IMAGING DEVICE, AND PLANOGRAPHIC PRINTING PLATE PRECURSOR, AND NOVEL COMPOUND

CROSS REFERENCE TO RELATED APPLICATIONS

This application is a National Stage of International Application No. PCT/JP2010/063585, filed on Aug. 10, 2010, which claims priority from Japanese Patent Application No. 2009-211931, filed on Sep. 14, 2009, the contents of all of which are incorporated herein by reference in their entirety.

TECHNICAL FIELD

The present invention relates to a polymerizable composition, a color filter formed by using the polymerizable compound and a method of producing the same, a solid-state imaging device having the color filter, and a planographic printing plate precursor, and a novel compound contained in the polymerizable compound.

BACKGROUND ART

As a photopolymerizable composition, for example, there is a photopolymerizable composition, in which a photopolymerization initiator is added to a polymerizable compound having an ethylenic unsaturated bond. Such a photopolymerizable composition is polymerized and cured by being irradiated with light, and is used for a photocurable ink, a photosensitive printing plate, a color filter, various photoresists, and the like.

Further, there is another embodiment, in which, for example, a photopolymerization initiator generates an acid by being irradiated with light, and the generated acid is used as a catalyst. Specifically, the photopolymerization initiator is used for a material for image formation, forgery prevention, and energy radiation-dose detection, by utilizing the color reaction of a dye precursor catalyzed by the generated acid. Or, the photopolymerization initiator is used for a positive-working photoresist and the like for manufacturing a semiconductor, a TFT, a color filter, a component for a micromachine, and the like, by utilizing a decomposition reaction by the generated acid.

In another embodiment, the photopolymerization initiator is cleaved to generate a radical due to light irradiation, and the generated radical polymerizes a polymerizable compound to form a pattern. By utilizing this, the photopolymerization initiator is used for a negative resist for manufacturing a color filter, a negative resist for image recording such as a printing plate, or the like.

In recent years, in particular, photopolymerizable compositions that are sensitive to a light source having a short wavelength (for example, 365 nm and 405 nm) have been demanded for various uses, and demand for photopolymerization initiators having high sensitivity to such a short wavelength light source has been increasing. However, photopolymerization initiators having excellent sensitivity are generally unstable, and accordingly, photopolymerization initiators simultaneously achieving increased sensitivity and storage stability, are desired.

For this reason, as photopolymerization initiators used for the photopolymerizable composition, oxime ester derivatives are proposed in, for example, U.S. Pat. No. 4,255,513, U.S. Pat. No. 4,590,145, Japanese Patent Application Laid-Open (JP-A) No. 2000-80068, JP-A No. 2001-233842, JP-A No. 2006-342166, and JP-A No. 2007-231000. However, with respect to these known oxime ester compounds, since the reactivity between radical species generated by photodecomposition and a polymerizable compound is low, the curing rate is low, and a sufficient sensitivity has not be obtained.

The photopolymerizable composition is also desired to have excellent preservation stability, and to generate radical species having an excellent reactivity with a polymerizable compound upon exposure of a photopolymerization initiator to light, and to have a high sensitivity.

For example, JP-A No. 2005-202252 discloses a colored radiation-sensitive composition for color filters, which contains an oxime ester compound; however, the storage stability and the sensitivity to lights of short wavelengths were still insufficient.

Moreover, in colored radiation-sensitive compositions for color filters, the reproducibility of color hue after pattern formation is a new problem, and a solution to the problem of change in colorability with the passage of time has been strongly desired.

Meanwhile, for the purpose of improving image quality owing to the light collectivity and the high color separation property of a solid-state imaging device such as a CCD in the color filter for image sensors, there is a strong demand for high color density and reduced thickness of color filters. When a colorant is used in a large amount in order to obtain a high color density, the sensitivity for reproducing a microscopic pixel pattern shape of 2.5 µm or less with high fidelity becomes insufficient, and overall, defects of the pattern tend to occur frequently. In addition, in order to eliminate these defects, light irradiation with higher energy is required and resultantly light exposure time is prolonged, thereby reducing the production yield remarkably.

As described above, from the viewpoint of the necessity of obtaining good pattern formability while containing a colorant (coloring agent) at high concentration in the colored radiation-sensitive composition for color filters, a photopolymerizable composition and photopolymerization initiator each of which has high sensitivity have been desired.

SUMMARY OF THE INVENTION

Technical Problem

Problems to be solved by the present invention is to attain the following objects.

A first object of the present invention is to provide a photopolymerizable composition having a high sensitivity and excellent intra-membrane curability.

A second object of the present invention is to provide a color filter having a coloring pattern which, when the photopolymerizable composition is used for forming a colored area of the color filter, has a favorable patternability and an excellent adhesion to a support and which retains a pattern shape even during post-heating after development and suppresses coloring by heating; and to provide a manufacturing method in which the color filter can be manufactured with a high productivity.

A third object of the present invention is to provide a solid-state image sensing device having a favorable pattern shape and a high resolution, and a liquid crystal display having a favorable pattern shape and a favorable color purity.

A fourth object of the present invention is to provide a planographic printing plate precursor which can form an image with a high sensitivity.

A fifth object of the present invention is to provide a novel oxime ester compound which has a high sensitivity and does not undergo oxygen-induced inhibition of polymerization.

Means for Solving the Problems

As a result of intensive studied, the present inventors have obtained a knowledge that, by using as a photopolymerization initiator an oxime ester compound having a novel specific structure, a photopolymerizable composition which has high reactivity between the oxime ester compound and a polymerizable compound, and a high sensitivity, and also has an excellent preservation stability can be obtained. Concrete measures to solve the above-mentioned problems are shown below.

<1> A photopolymerizable composition including a photopolymerization initiator (A) having a partial structure represented by the following Formula (1) and a polymerizable compound (B).

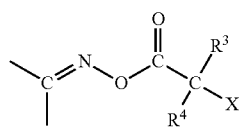
(1)

In Formula (1), $R^3$ and $R^4$ each independently represent a hydrogen atom, an alkyl group, an alkenyl group, an alkynyl group, an aryl group, a heteroaryl group or an alkoxy group. $R^3$ and $R^4$ may bind to one another to form a ring. X represents $OR^5$, $SR^6$ or $NR^{17}R^{18}$. $R^5$, $R^6$, $R^{17}$ and $R^{18}$ each independently represent a hydrogen atom, an alkyl group, an alkenyl group, an alkynyl group, an aryl group or a heteroaryl group. $R^{17}$ and $R^{18}$ may bind to one another to directly form a ring, or form a ring via a divalent linking group.

<2> The photopolymerizable composition according to the item <1>, wherein the photopolymerization initiator having the partial structure represented by the above-described Formula (1) is a compound represented by the following Formula (2).

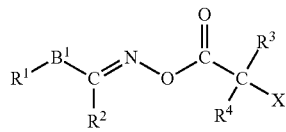
(2)

In Formula (2), $R^1$ and $R^2$ each independently represent a hydrogen atom, an alkyl group, an alkenyl group, an alkynyl group, an aryl group or a heteroaryl group. $R^1$ and $R^2$ may bind to one another to form a ring. $B^1$ represents a single bond or a carbonyl group. $R^3$, $R^4$ and X have the same definition as $R^3$, $R^4$ and X in the above-described Formula (1), respectively.

<3> The photopolymerizable composition according to the item <1> or <2>, wherein the photopolymerization initiator having a partial structure represented by the above-described Formula (1) is a compound represented by the following Formula (3).

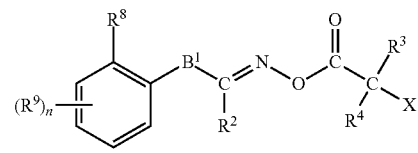
(3)

In Formula (3), $B^1$, X, $R^2$, $R^3$ and $R^4$ each have the same definition as those of $B^1$, X, $R^2$, $R^3$ and $R^4$ in the above-described Formula (2), respectively. $R^8$ represents a hydrogen atom, an alkyl group, an alkoxy group or an alkylthio group. $R^8$ may bind to $R^2$ via a divalent linking group to form a ring structure. $R^9$ represents an alkyl group, an alkenyl group, an aryl group, a heteroaryl group, an alkoxy group, an aryloxy group, an alkylthio group, an arylthio group, an amino group, an arylcarbonyl group, a heteroarylcarbonyl group or a halogen atom. When there is more than one $R^9$, respective $R^9$s may bind to one another via a divalent linking group. n represents an integer of 0 to 2. When n is 2, respective $R^9$s may be the same as or different from each other.

<4> The photopolymerizable composition according to any one of the items <1> to <3>, wherein the photopolymerization initiator having a partial structure represented by the above-described Formula (1) is a compound represented by the following Formula (4) or Formula (5).

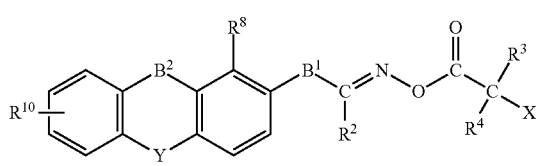
(4)

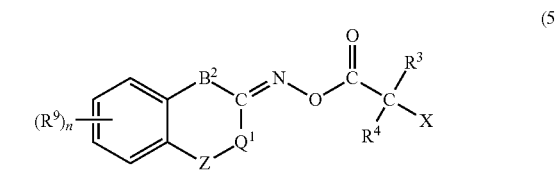
(5)

In Formula (4), $B^2$ represents a single bond, an alkylene group, an oxygen atom, a sulphur atom or a carbonyl group. Y represents an alkylene group, an oxygen atom, a sulphur atom or $NR^{13}$. $R^{13}$ represents an alkyl group or an aryl group. $R^{10}$ represents a hydrogen atom, a halogen atom, an arylcarbonyl group or a heteroarylcarbonyl group. $B^1$, X, $R^2$, $R^3$ and $R^4$ have the same definition as those of $B^1$, X, $R^2$, $R^3$ and $R^4$ in the above-described Formula (2), respectively. $R^8$ has the same definition as $R^8$ in the above-described Formula (3).

In Formula (5), Z represents an alkylene group, an oxygen atom or a sulphur atom. $Q^1$ represents a single bond or a divalent linking group. $B^1$, X, $R^3$ and $R^4$ have the same definition as $B^1$, X, $R^3$ and $R^4$ in the above-described Formula (2), respectively, and $R^9$ and n have the same definition as $R^9$ and n in the above-described Formula (3), respectively. When n is 2, respective $R^9$s may be the same as or different from each other.

<5> The photopolymerizable composition according to any one of the items <1> to <3>, wherein the photopolymerization initiator having a partial structure represented by the above-described Formula (1) is a compound represented by the following Formula (6).

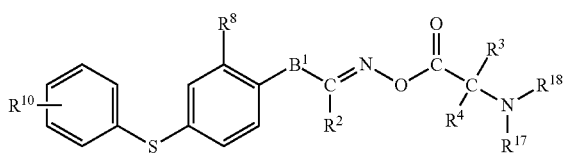

(6)

In the above-described Formula (6), $R^3$, $R^4$, $R^{17}$ and $R^{18}$ have the same definition as $R^3$, $R^4$, $R^{17}$ and $R^{18}$ in the above-described Formula (1), respectively. $B^1$ and $R^2$ have the same definition as $B^1$ and $R^2$ in the above-described Formula (2), respectively. $R^8$ has the same definition as $R^8$ in the above-described Formula (3), and $R^{10}$ has the same definition as $R^{10}$ in the above-described Formula (4).

<6> The photopolymerizable composition according to any one of the items <1> to <4>, wherein the photopolymerization initiator having a partial structure represented by the above-described Formula (1) is a compound represented by the following Formula (7) or Formula (8).

(7)

(8)

In the above-described Formula (7) and Formula (8), $R^{12}$ represents a hydrogen atom, an alkyl group or an aryl group. $Q^2$ represents $-(CH_2)_{n1}-$, and n1 represents an integer of 0 to 2. $R^3$, $R^4$, $R^{17}$ and $R^{18}$ have the same definition as $R^3$, $R^4$, $R^{17}$ and $R^{18}$ in the above-described Formula (1), respectively. $R^2$ and $B^1$ have the same definition as $R^2$ and $B^1$ in the above-described Formula (2), respectively. $R^8$, $R^9$ and n have the same definition as $R^8$, $R^9$ and n in the above-described Formula (3), respectively, and $R^{10}$ has the same definition as $R^{10}$ in the above-described Formula (4). When n is 2, respective $R^9$s may be the same as or different from each other.

<7> The photopolymerizable composition according to any one of the items <1> to <6>, further including a coloring agent (C).

<8> The photopolymerizable composition according to the item <7>, wherein the coloring agent (C) is a pigment, and the photopolymerizable composition further includes a pigment dispersing agent (D).

<9> The photopolymerizable composition according to the item <7> or <8>, wherein the coloring agent is a black coloring agent (C).

<10> The photopolymerizable composition according to any one of the items <7> to <9>, which is used for forming a colored area of a color filter.

<11> A color filter having a support and, on the support, a colored area formed by using the photopolymerizable composition according to the item <10>.

<12> A method for manufacturing a color filter, including:
a process of applying the photopolymerizable composition according to the item <10> to a support to form a photopolymerizable composition layer;
a process of exposing the photopolymerizable composition layer to light patternwise; and
a process of developing the exposed photopolymerizable composition layer to form a colored pattern.

<13> A solid-state image sensing device including the color filter according to the item <11>.

<14> A liquid crystal display including the color filter according to the item <11>.

<15> A planographic printing plate precursor having a photosensitive layer containing the photopolymerizable composition according to any one of the items <1> to <7>.

<16> A compound represented by the following Formulae (6), (7) or (8).

(6)

(7)

(8)

In the above-described Formulae (6) to (8), $R^2$ represents a hydrogen atom, an alkyl group, an alkenyl group, an alkynyl group, an aryl group or a heteroaryl group. $R^3$ and $R^4$ each independently represent a hydrogen atom, an alkyl group, an alkenyl group, an alkynyl group, an aryl group, a heteroaryl group or an alkoxy group. $R^3$ and $R^4$ may bind to one another to form a ring. $R^8$ represents a hydrogen atom, an alkyl group, an alkoxy group or an alkylthio group. $R^8$ may be bind to $R^2$ via a divalent linking group to form a ring structure. $R^9$ represents an alkyl group, an alkenyl group, an aryl group, a heteroaryl group, an alkoxy group, an aryloxy group, an alkylthio group, an arylthio group, an amino group, an arylcarbonyl group, a heteroarylcarbonyl group or a halogen atom. When there is more than one $R^9$, respective $R^9$s may bind to one another via a divalent linking group. n represents an integer of 0 to 2. When n is 2, respective $R^9$s may be the same as or different from each other. $R^{10}$ represents a hydrogen atom, a halogen atom, an arylcarbonyl group or a heteroarylcarbonyl group. $R^{12}$ represents a hydrogen atom, an alkyl group or an aryl group. $R^{17}$ and $R^{18}$ each independently represent a hydrogen atom, an alkyl group, an alkenyl group, an alkynyl group, an aryl group or a heteroaryl group. $R^{17}$ and $R^{18}$ may directly form a ring or may form a ring via a divalent linking group. $B^1$ represents a single bond or a carbonyl group. $Q^2$ represents —$(CH_2)_{n1}$—, wherein n1 represents an integer of 0 to 2.

In the present invention, by using an oxime ester having a novel specific structure as a photopolymerization initiator, a photopolymerizable composition having a high sensitivity is obtained. This is thought to be due to the photopolymerization initiator having a specific structure in the present invention, that is photodegraded by light irradiation to generate radical species have a high reactivity with a polymerizable compound such as a monomer. No undercut is observed on the pattern shape obtained by pattern exposure and little change due to heating after a pattern formation was observed, and thus, a pattern having a stable shape was obtained. This is presumed to be due to the photopolymerization initiator having a specific structure according to the present invention, and having excellent intra-membrane curability.

The photopolymerizable composition layer of the present invention cures with a high sensitivity under air without an oxygen blocking layer. This is thought to be due to generated radicals in the present invention that have a heteroatom at α-position and have a decreased reactivity with oxygen in comparison with existing radicals, whereby inhibition of polymerization by oxygen is not caused.

Effects of the Invention

The present invention can provide a photopolymerizable composition having a high sensitivity and an excellent intra-membrane curability.

The present invention can provide a color filter having a colored pattern which, when the photopolymerizable composition is used for forming a colored area of the color filter, has a favorable patternability and an excellent adhesion to a support and which retains a pattern shape even during postheating after development and avoids coloring by heating; and can provide a manufacturing method in which the color filter can be manufactured with a high productivity.

Further, the present invention can provide a solid-state image sensing device having a favorable pattern shape and a high resolution, and a liquid crystal display having a favorable pattern shape and a favorable color purity.

Further, the present invention can provide a planographic printing plate precursor which can form an image with a high sensitivity.

Further, the present invention can provide a novel oxime ester compound which has a high sensitivity and does not undergo inhibition of polymerization by oxygen.

MODES FOR CARRYING OUT THE INVENTION

A photopolymerizable composition of the present invention is characterized by containing a photopolymerization initiator (A) having a partial structure represented by the following Formula (1) (hereinafter, referred to as "specific oxime compound" as appropriate), and a polymerizable compound (B).

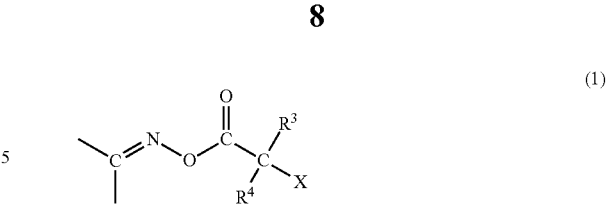

In Formula (1), $R^3$ and $R^4$ each independently represent a hydrogen atom, an alkyl group, an alkenyl group, an alkynyl group, an aryl group, a heteroaryl group or an alkoxy group. $R^3$ and $R^4$ may bind to one another to form a ring. X represents $OR^5$, $SR^6$ or $NR^{17}R^{18}$. $R^5$, $R^6$, $R^{17}$ and $R^{18}$ each independently represent a hydrogen atom, an alkyl group, an alkenyl group, an alkynyl group, an aryl group or a heteroaryl group. $R^{17}$ and $R^{18}$ may directly form a ring or may form a ring via a divalent linking group.

The specific oxime compound (A) used in the present invention has a function as a photopolymerization initiator which decomposes by light irradiation to generate radical initiating species and polymerizes a polymerizable compound (B). In particular, since radical species generated by photodecomposition of a specific oxime compound have a high reactivity with a polymerizable compound, the specific oxime compound has a high polymerization rate and an excellent sensitivity, and therefore, when used as a photopolymerization initiator in a photopolymerizable composition, the specific oxime compound exerts an excellent effect.

In the following, each of the ingredients contained in the polymerizable compound of the present invention will be described.

In the present invention, an alkyl group, an alkenyl group, an alkynyl group, an aryl group, a heteroaryl group, an alkoxy group, an aryloxy group, an alkylthio group, an arylthio group, an amino group, an arylcarbonyl group and a heteroarylcarbonyl group, all of which are groups in Formulae (1) to (8), may further have a substituent unless otherwise specified.

<A Photopolymerization Initiator (A) Having a Partial Structure Represented by Formula (1) (Specific Oxime Compound)>

The specific oxime compound in the present invention is a compound having a partial structure represented by Formula (1).

In Formula (1), in the case where $R^3$ and $R^4$ represent an alkyl group, as the alkyl group which may have a substituent, an alkyl group having 1 to 30 carbon atoms is preferred, an alkyl group having 1 to 20 carbon atoms is more preferred, and an alkyl group having 1 to 10 carbon atoms is still more preferred.

Concretely, examples thereof include a methyl group, an ethyl group, a propyl group, a butyl group, a hexyl group, an octyl group, a decyl group, a dodecyl group, an octadecyl group, an isopropyl group, an isobutyl group, a sec-butyl group, a t-butyl group, a 1-ethylpentyl group, a cyclopentyl group, a cyclohexyl group, a trifluoromethyl group, a 2-ethylhexyl group, a phenacyl group, a 1-naphthoylmethyl group, a 2-naphthoylmethyl group, a 4-methylsulfanylphenacyl group, a 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group, a 3-nitrophenacyl group, an allyl group and a propargyl group.

Among the above-mentioned concrete examples, as the alkyl group, a methyl group, an ethyl group, a propyl group, a 2-ethylhexyl group, an isopentyl group, an ethoxyethyl group, a methoxyethoxyethyl group, a phenoxyethyl group, a methoxyethyl group, a cyclohexylmethyl group, a cyclopentylmethyl group, a tetrahydrofuranylmethyl group, a methoxypropyloxy group, a methoxypropyloxypropyl group, a t-butylmethyl group, an allyl group and a propargyl group are preferred. A methyl group, an ethyl group, a 2-ethylhexyl group, an isopentyl group, an ethoxyethyl group, a methoxyethoxyethyl group, a phenoxyethyl group, a methoxyethyl group, a cyclohexylmethyl group and a t-butylmethyl group are more preferred. A methyl group, an ethyl group, a 2-ethylhexyl group, an isopentyl group, an ethoxyethyl group, a cyclohexylmethyl group, an allyl group and a propargyl group are still more preferred.

In Formula (1), in the case where $R^3$ and $R^4$ represent an alkenyl group, as the alkenyl group which may have a substituent, an alkenyl group having 2 to 20 carbon atoms is preferred, an alkenyl group having 2 to 10 carbon atoms is more preferred, and an alkenyl group having 2 to 8 carbon atoms is still more preferred.

Concretely, examples thereof include a vinyl group and a styryl group.

In Formula (1), in the case where $R^3$ and $R^4$ represent an alkynyl group, as the alkynyl group which may have a substituent, an alkynyl group having 2 to 20 carbon atoms is preferred, an alkynyl group having 2 to 10 carbon atoms is more preferred, and an alkynyl group having 2 to 4 carbon atoms is still more preferred.

Concretely, examples thereof include an acetylenyl group, a propynyl group and a phenylacetylenyl group.

In the case where $R^3$ and $R^4$ represent an aryl group, as an aromatic ring of the aryl group which may have a substituent, an aromatic ring having 6 to 30 carbon atoms is preferred, an aromatic ring having 6 to 20 carbon atoms is more preferred, and an aromatic ring having 6 to 12 carbon atoms is still more preferred.

Concretely, examples thereof include a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, a quarter phenyl group, an o-, m- and p-tolyl group, a xylyl group, an o-, m- and p-cumenyl group, a mesityl group, a pentalenyl group, a binaphthalenyl group, a ternaphthalenyl group, a quarter naphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quarter anthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, an ovalenyl group, a p-chlorophenyl group, a p-bromophenyl group, a p-fluorophenyl group, a p-iodophenyl group, a m-chlorophenyl group, a m-bromophenyl group, a m-fluorophenyl group, a m-iodophenyl group, an o-chlorophenyl group, an o-bromophenyl group, an o-fluorophenyl group, an o-iodophenyl group, a p-methoxyphenyl group, a m-methoxyphenyl group, a p-methylthiophenyl group, a m-methylthiophenyl group and a p-phenylthiophenyl group.

Among the above-mentioned concrete examples, a phenyl group, a 9-fluorenyl group, a p-chlorophenyl group, a p-bromophenyl group, a p-fluorophenyl group, a p-iodophenyl group, a m-chlorophenyl group, a m-bromophenyl group, a m-fluorophenyl group, a m-iodophenyl group, an o-chlorophenyl group, an o-bromophenyl group, an o-fluorophenyl group, an o-iodophenyl group, a p-methoxyphenyl group, a m-methoxyphenyl group, a p-methylthiophenyl group, a m-methylthiophenyl group, a p-phenylthiophenyl group are more preferred, and a p-chlorophenyl group, a p-bromophenyl group, a m-chlorophenyl group and a m-bromophenyl group are still more preferred.

In the case where $R^3$ and $R^4$ represent a heteroaryl group, examples of the heteroaryl group include aromatic groups having 2 to 12 carbon atoms and having a nitrogen atom, an oxygen atom, a sulphur atom or a phosphorus atom.

Concrete examples thereof include a thienyl group, a benzo[b]thienyl group, a naphtho[2,3-b]thienyl group, a thianthrenyl group, a furyl group, a pyranyl group, an isobenzofuranyl group, a chromenyl group, a xanthenyl group, a phenoxathiinyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naphthyridinyl group, a quinoxanilyl group, a quinazolinyl group, a cinnolinyl group, a pteridinyl group, a 4aH-carbazolyl group, a carbazolyl group, β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxazinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinuclidinyl group, a morpholinyl group, and a thioxanetolyl group. Thienyl group, a pyridyl group, a furyl group, a pyranyl group, an imidazolyl group, a thioxanetolyl group and a carbazolyl group are more preferred.

In Formula (1), in the case where $R^3$ and $R^4$ represent an alkoxy group, as the alkoxy group which may have a substituent, an alkoxy group having 1 to 10 carbon atoms is preferred, an alkoxy group having 1 to 5 carbon atoms is more preferred, and an alkoxy group having 1 to 3 carbon atoms is still more preferred.

Concretely, examples thereof include a methoxy group, an ethoxy group, a propyloxy group, a butoxy group and an isopropoxy group.

In Formula (1), X represents $OR^5$, $SR^6$ or $NR^{17}R^{18}$.

Examples of $OR^5$ include a hydroxyl group, a methoxy group, an ethoxy group, a propyloxy group, an isopropyloxy group, a phenoxy group, a (p-methyl)phenoxy group, a (p-t-butyl)phenoxy group, a (p-methoxy)phenoxy group, a (p-hydroxy)phenoxy group, a (p-dimethylamino)phenoxy group, a (p-chloro)phenoxy group, a (p-bromo)phenoxy group, a (p=trifluoromethyl)phenoxy group, a (p-nitro)phenoxy group and a (p-cyano)phenoxy group.

Examples of $SR^6$ include a thiol group, a methylthio group, an ethylthio group, a propylthio group, an isopropylthio group, a phenylthio group, a (p-methyl)phenylthio group, a (p-t-butyl)phenylthio group, a (p-methoxy)phenylthio group, a (p-hydroxy)phenylthio group, a (p-dimethylamino)phenylthio group, a (p-chloro)phenylthio group, a (p-bromo)phenylthio group, a (p-trifluoromethyl)phenylthio group, a (p-nitro)phenylthio group and a (p-cyano)phenylthio group.

Examples of $NR^{17}R^{18}$ include a dimethylamino group, a diethylamino group, a dipropylamino group, a diisopropylamino group, a dibutyamino group, a diphenylamino group, a pyrrolidyl group, a piperidyl group, a morpholino group, a thiomorpholino group, a piperadyl group and an azetidyl group.

X in Formula (1) represents $OR^5$, $SR^6$ and $NR^{17}R^{18}$. Among these, $SR^6$ or $NR^{17}R^{18}$ is preferred, and $NR^{17}R^{18}$ is more preferred, whereby a high reactivity with a polymerizable compound, a high polymerization rate and a high sensitivity are achieved.

Examples of preferred X in Formula (1) include a hydroxyl group, a methoxy group, a thiol group, a methylthio group, a pyrrolidyl group and a morpholino group.

The specific oxime compound may be any compound as long as the compound contains at least one partial structure of Formula (1).

Especially, a compound represented by the following Formula (2) is described.

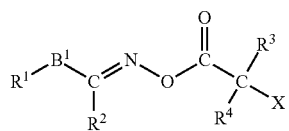

(2)

$R^1$, $R^2$, $R^3$ and $R^4$ in Formula (2) have the same definition as $R^3$ in Formula (1), and $R^1$, $R^2$, $R^3$ and $R^4$ may be the same or different. X in Formula (2) has the same definition as X in Formula (1).

In Formula (2), $B^1$ represents a single bond or a carbonyl group.

The specific oxime compound represented by Formula (2) is still more preferably a compound represented by the following Formula (3).

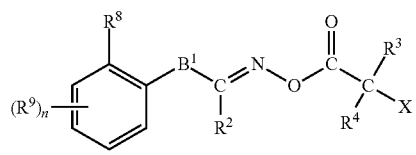

(3)

$B^1$, X, $R^2$, $R^3$ and $R^4$ in Formula (3) have the same definition as $B^1$, X, $R^2$, $R^3$ and $R^4$ in Formula (2). $R^8$ represents a hydrogen atom, an alkyl group, an alkoxy group or an alkylthio group. $R^8$ may bind to $R^2$ via a divalent linking group to form a ring structure. $R^9$ represents an alkyl group having 1 to 10 carbon atoms, an alkenyl group having 1 to 10 carbon atoms, an aryl group having 6 to 20 carbon atoms, a heteroaryl group having 2 to 20 carbon atoms, an alkoxy group having 1 to 10 carbon atoms, an aryloxy group having 6 to 20 carbon atoms, an alkylthio group having 1 to 10 carbon atoms, an arylthio group having 6 to 20 carbon atoms, an amino group, an arylcarbonyl group having 7 to 20 carbon atoms, a heteroarylcarbonyl group having 3 to 20 carbon atoms or a halogen atom, and when there is more than one $R^9$, respective $R^9$s may bind to one another via a single bond or a divalent linking group. n represents an integer of 0 to 2. When n is 2, respective $R^9$s may be the same as or different from each other.

Examples of the alkyl group represented by $R^8$ include an alkyl group having 1 to 5 carbon atoms. A methyl group, an ethyl group or an isopropyl group is preferred.

Examples of the alkoxy group represented by $R^8$ include an alkoxy group having 1 to 5 carbon atoms. A methoxy group, an ethoxy group or a propyloxy group is preferred.

Examples of the alkylthio group represented by $R^8$ include an alkylthio group having 1 to 5 carbon atoms. A methylthio group, an ethylthio group, a propylthio group or an isopropylthio group is preferred.

As $R^8$, a methoxy group, a methylthio group or an isopropylthio group is preferred.

Examples of the halogen atom represented by $R^9$ include fluorine, chlorine, bromine, iodine. Fluorine, chlorine and bromine are more preferred, and chlorine and bromine are still more preferred.

As $R^9$, an aryl group, an arylthio group and an amino group are preferred.

Further, as the specific oxime compound, a compound represented by the following Formula (4) or Formula (5) is preferred.

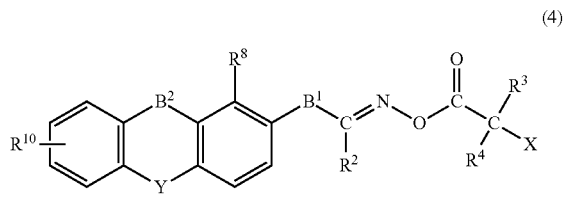

(4)

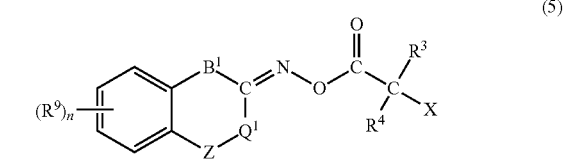

(5)

In Formula (4), $B^2$ represents a single bond, an alkylene group, an oxygen atom, a sulphur atom or a carbonyl group. Y represents an alkylene group, an oxygen atom, a sulphur atom or $NR^{13}$. $R^{13}$ represents an alkyl group or an aryl group. $R^{10}$ represents a hydrogen atom, a halogen atom, an arylcarbonyl group or a heteroarylcarbonyl group. $B^1$, X, $R^2$, $R^3$ and $R^4$ have the same definition as $B^1$, X, $R^2$, $R^3$ and $R^4$ in Formula (2). $R^8$ has the same definition as $R^8$ in Formula (3).

In Formula (5), Z represents an alkylene group, an oxygen atom or a sulphur atom. $Q^1$ represents a single bond or a divalent linking group. $B^1$, X, $R^3$ and $R^4$ have the same definition as those of $B^1$, X, $R^3$ and $R^4$ in Formula (2), $R^9$ and n have the same definition as $R^9$ and n in Formula (3), and the preferred range thereof is also the same. When n is 2, respective $R^9$s may be the same as or different from each other.

In Formula (4), examples of the alkylene group represented by $B^2$ include an alkylene group having 1 to 3 carbon atoms. A methylene group or an ethylene group is preferred.

As $B^2$, a single bond, a sulphur atom, an oxygen atom or a carbonyl group is preferred.

In Formula (4), examples of the alkylene group represented by Y include an alkylene group having 1 to 3 carbon atoms. A methylene group or an ethylene group is preferred.

Examples of the alkyl group represented by $R^{13}$ include an alkyl group having 1 to 8 carbon atoms, and examples of the aryl group represented by $R^{13}$ include an aryl group having 6 to 12 carbon atoms.

Examples of the arylcarbonyl group represented by $R^{10}$ include an arylcarbonyl group having 7 to 20 carbon atoms. A phenylcarbonyl group, an o-tolyl carbonyl group, or a p-bromophenylcarbonyl group is preferred;

Examples of the heteroarylcarbonyl group represented by $R^{10}$ include a heteroarylcarbonyl group having 3 to 10 carbon atoms containing an oxygen atom, a sulphur atom or a nitrogen atom. A furyl carbonyl group, a thiophenecarbonyl group or a pyridinecarbonyl group is preferred.

In Formula (5), examples of the alkylene group represented by Z include an alkylene group having 1 to 2 carbon atoms. A methylene group or an ethylene group is preferred.

As Z, an oxygen atom or a sulphur atom is preferred.

Examples of the divalent linking group represented by $Q^1$ include a methylene group, an ethylene group, a propylene group, —CH(CH$_3$)—, —CH(CH$_3$)CH$_2$—, —CH(Ph)-, —CH(Ph)-CH$_2$—, —CH(CH$_3$)CH$_2$CH$_2$— and —CH(Ph)-CH$_2$CH$_2$—.

Further, the specific oxime compound is particularly preferably a compound represented by the following Formula (6), the following Formula (7) or the following Formula (8). The above-mentioned Formula (4) is preferably a compound represented by the following Formula (7), and the above-mentioned Formula (5) is particularly preferably a compound represented by the following Formula (8).

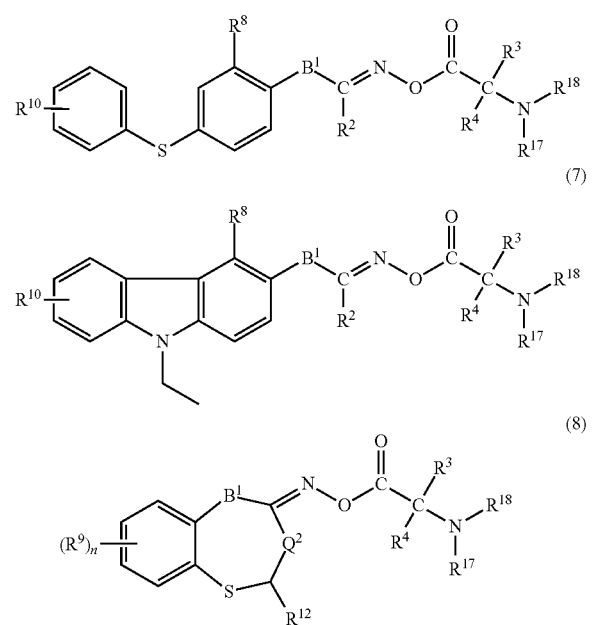

In Formulae (6) to (8), $R^{12}$ represents a hydrogen atom, an alkyl group or an aryl group. $Q^2$ represents —(CH$_2$)$_{n1}$—, and n1 represents an integer of 0 to 2. $R^3$, $R^4$, $R^{17}$ and $R^{18}$ have the same definition as $R^3$, $R^4$, $R^{17}$ and $R^{18}$ in Formula (1). $R^2$ and $B^1$ have the same definition as $R^2$ and $B^1$ in Formula (2), and the preferred range thereof is also the same. $R^8$, $R^9$ and n have the same definition as $R^8$, $R^9$ and n in Formula (3), and the preferred range thereof is also the same. $R^{10}$ has the same definition as $R^{10}$ in Formula (4), and the preferred range thereof is also the same. When n is 2, respective $R^9$s may be the same as or different from each other.

In Formula (8), examples of the alkyl group represented by $R^{12}$ include an alkyl group having 1 to 8 carbon atoms. A methyl group or an ethyl group is preferred.

Examples of the aryl group represented by $R^{12}$ include an aryl group having 6 to 12 carbon atoms. A phenyl group, a p-tolyl group or a p-methoxyphenyl group is preferred.

The molar extinction coefficient of the specific oxime compound at 365 nm is preferably from 50 to 500000, more preferably from 100 to 40000 and still more preferably from 500 to 30000 in ethyl acetate.

The molar extinction coefficient of the specific oxime compound in the present specification means a value measured by using an UV-visible spectrophotometer (CARRY-5 SPECTROPHOTOMETER manufactured by Varian, Inc.) and using an ethyl acetate solvent at the concentration of 0.01 g/L.

A compound having a partial structure represented by the general formula (1) can be synthesized in accordance with a general synthesis scheme (see the following FIGURE) which is a condensation reaction of an oxime compound and a carboxylic acid having a hetero substituent at α-position. Concretely, the compound can be obtained by dissolving an oxime compound into methylene chloride, adding thereto α-heterocarboxylic acid, dimethylaminopyridine (DMAP) and dicyclohexylcarbodiimide (DCC), and then stirring the mixture at 0° C.

The oxime compound is obtained by heating while stirring a carbonyl compound in a mixed solvent of N-methylpyrrolidone (NMP)/water with hydroxyamine hydrochloride and sodium acetate at 80° C. In the case of α-ketoxime, the compound is obtained by the action of isopentyl nitrite in ethanol (EtOH) in the presence of KOH at 0° C.

The carboxylic acid having a hetero substituent at α-position was synthesized with reference to an existing synthesis-related literature. The carboxylic acid is obtained by a nucleophilic substitution of ethyl 2-bromo-isobutyrate with a hetero compound and by an acid hydrolysis of the ester.

Examples of the synthesis-related literature include Journal of the American Chemical Society; 59, (1937), 2248 and Journal of Medicinal Chemistry: 44, (2001), 3582.

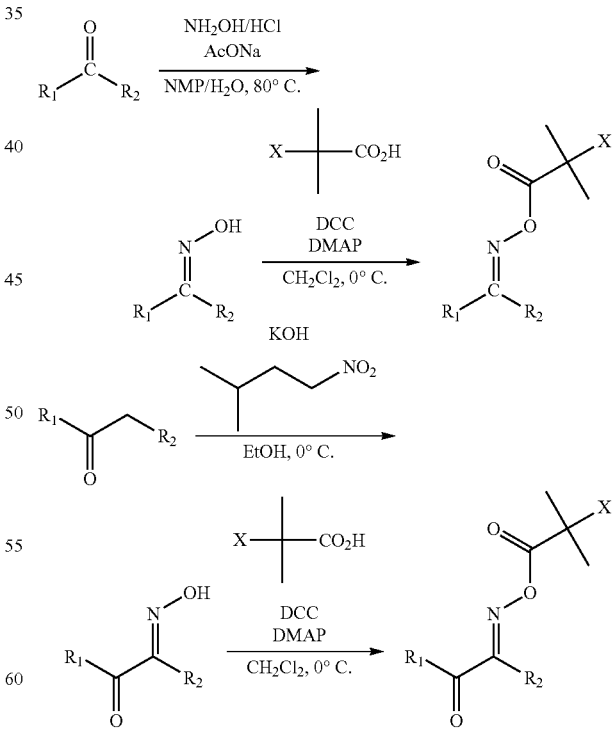

In the following, concrete examples of the specific oxime compounds of the present invention [exemplary compounds (A-1) to (A-135)] will be shown, but the present invention is not limited thereto.

(A-1) 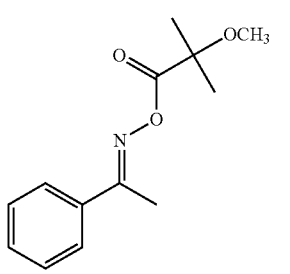
(A-2) 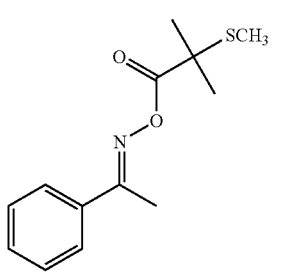
(A-3) 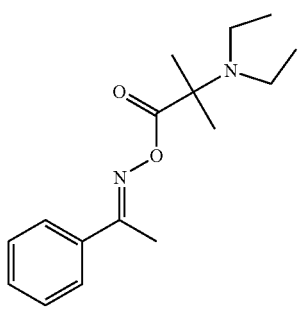
(A-4) 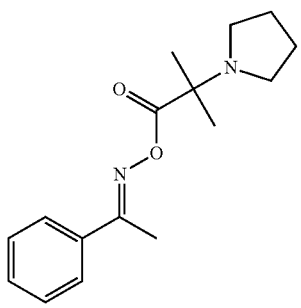
(A-5) 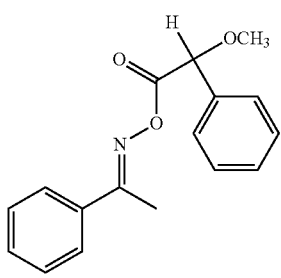
(A-6) 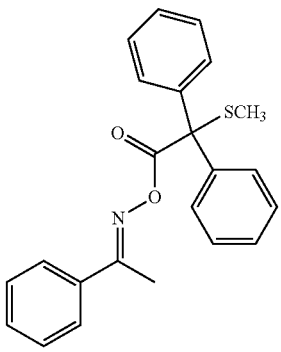
(A-7) 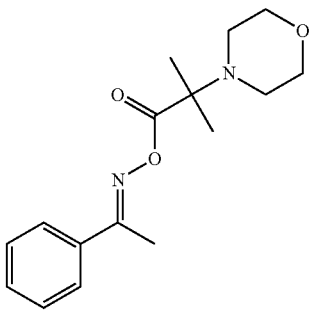
(A-8) 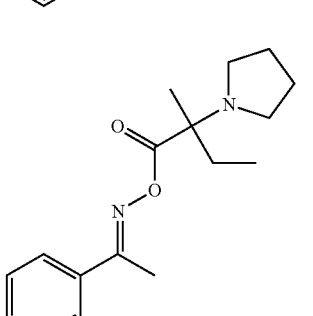
(A-9) 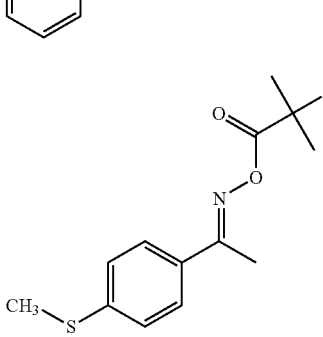
(A-10) 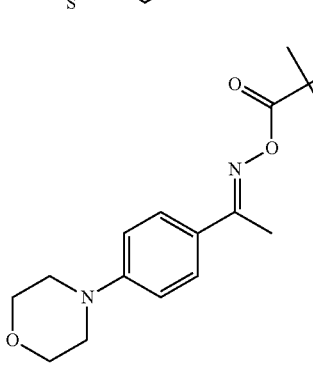

(A-11)
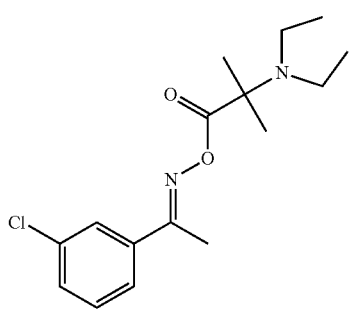
(A-12)
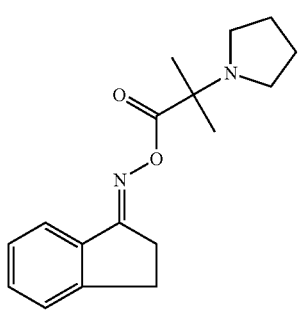
(A-13)
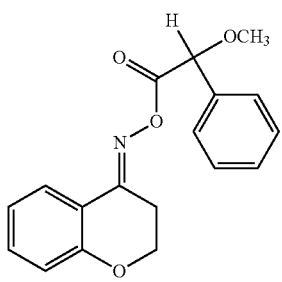
(A-14)
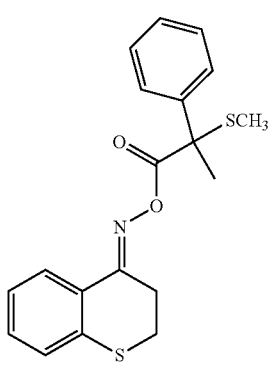
(A-15)
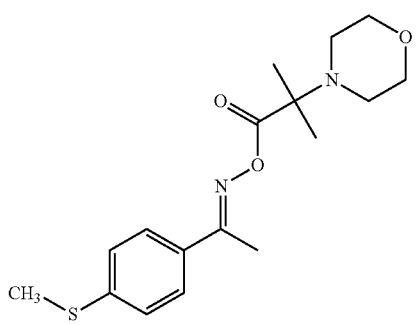
(A-16)
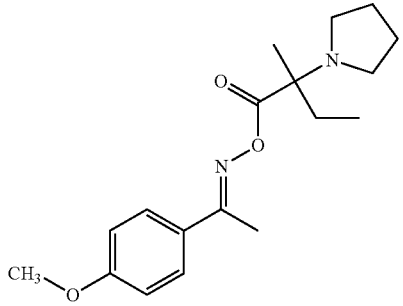
(A-17)
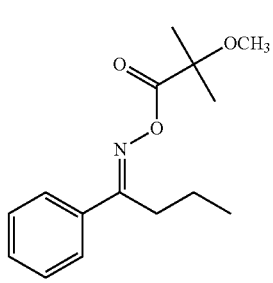
(A-18)
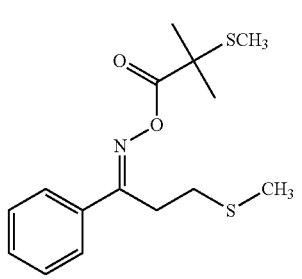
(A-19)
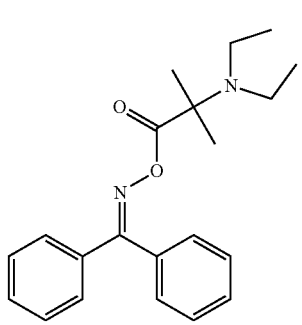
(A-20)
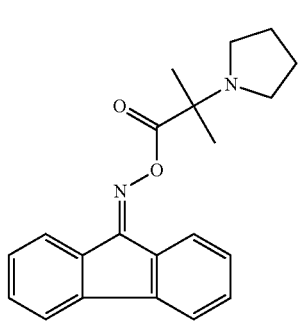

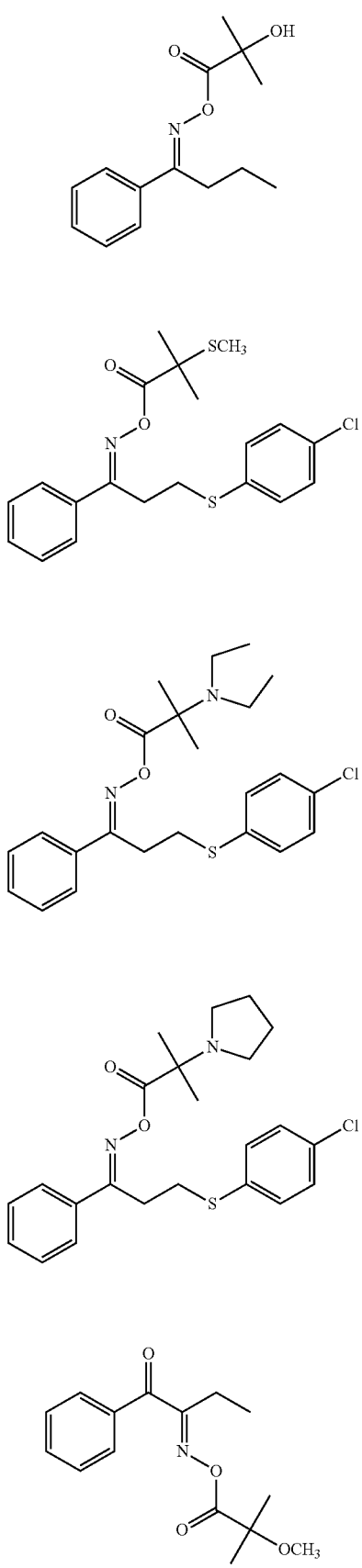

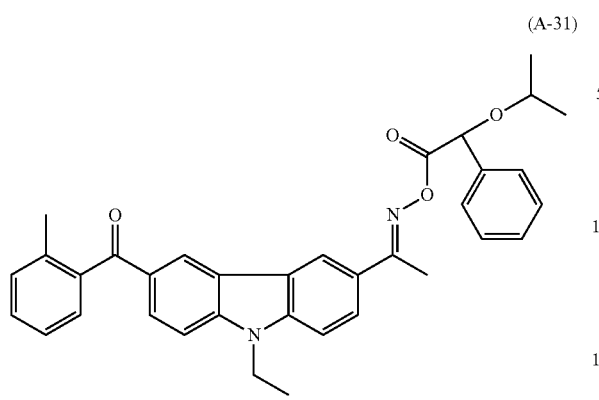
(A-31)
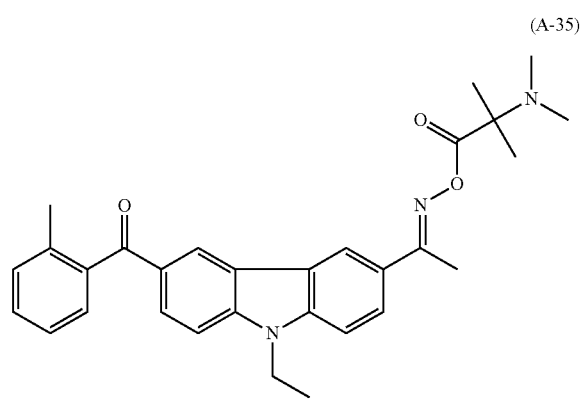
(A-35)
(A-32)
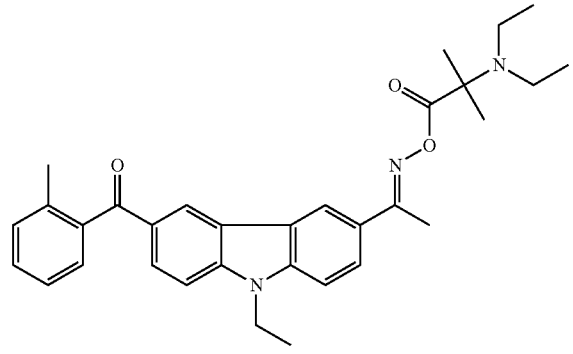
(A-36)
(A-33)
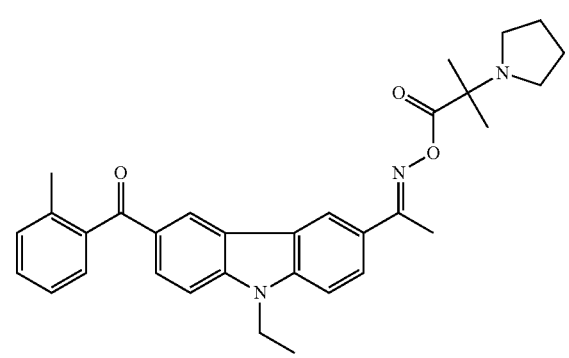
(A-37)
(A-34)
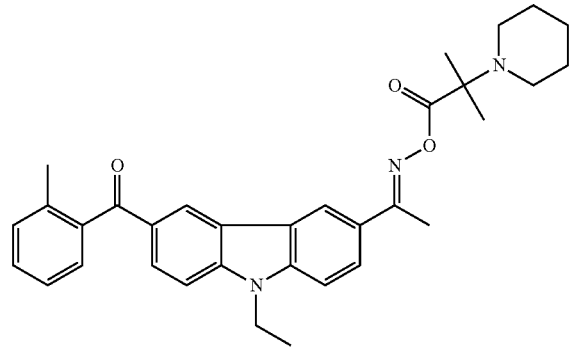
(A-38)

-continued
(A-39)
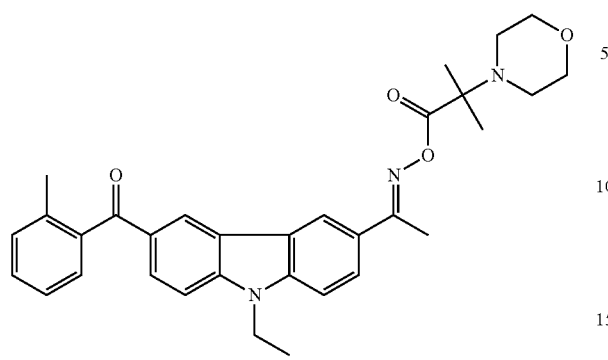
(A-40)
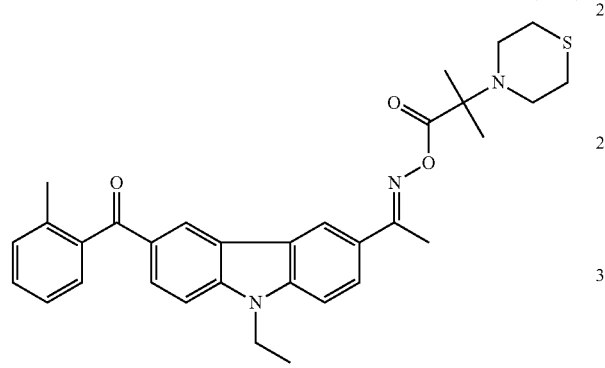
(A-41)
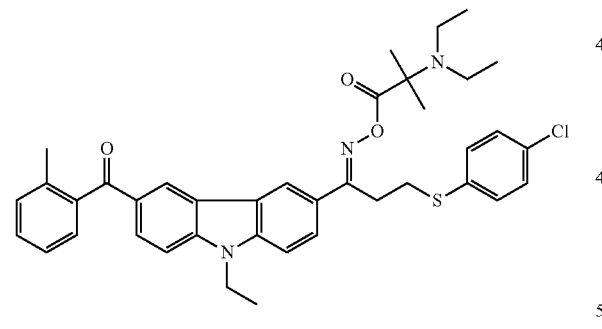
(A-42)
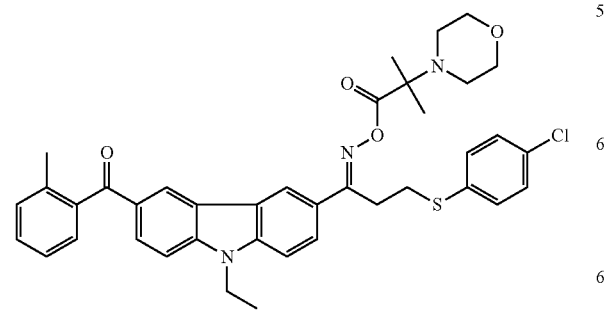
(A-44)
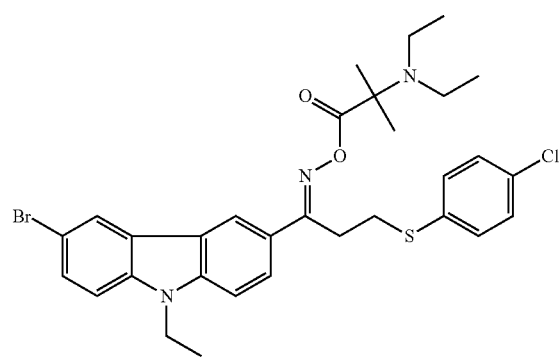
(A-45)
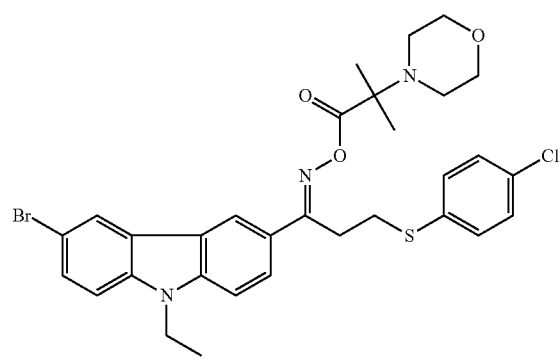
(A-46)
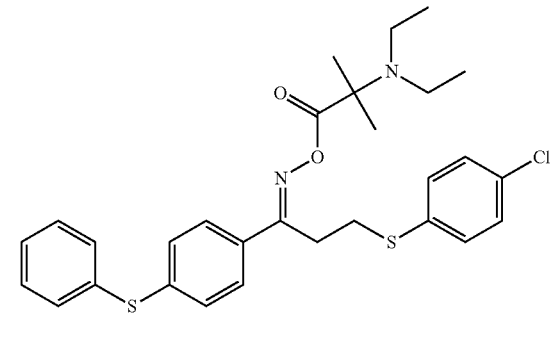
(A-47)
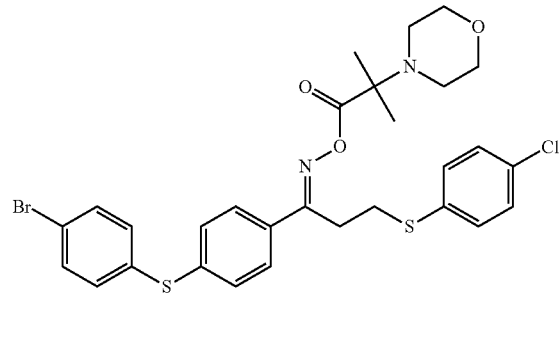

(A-48)
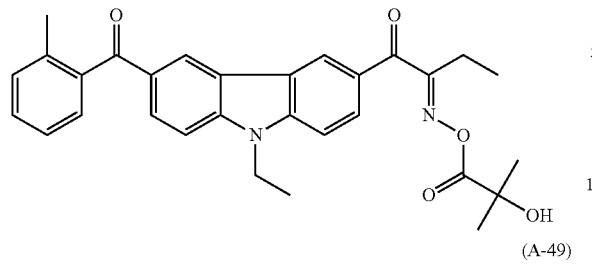
(A-49)
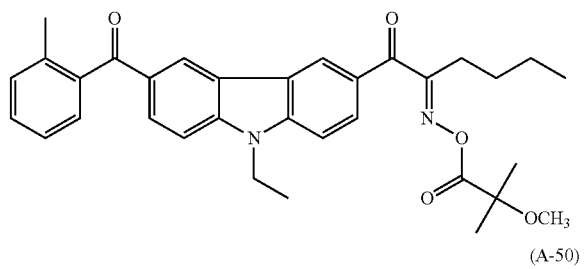
(A-50)
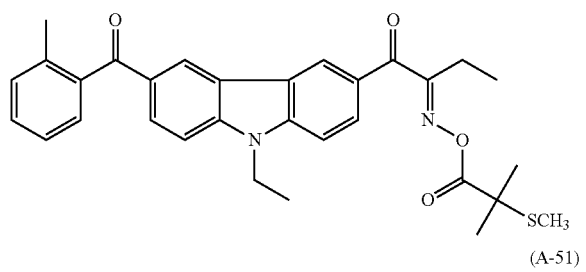
(A-51)
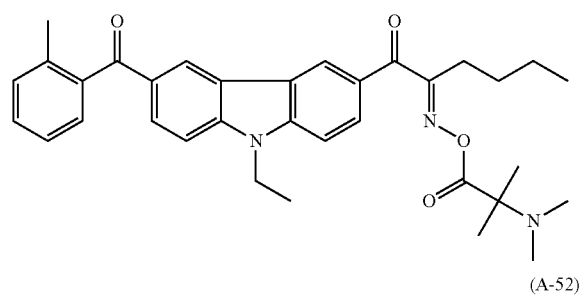
(A-52)
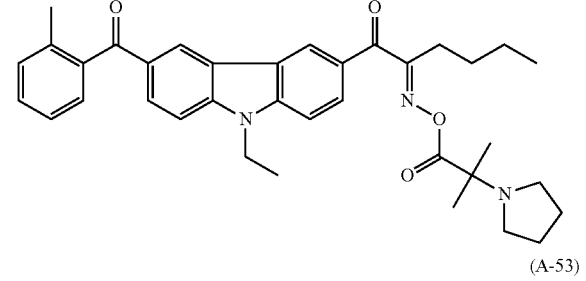
(A-53)
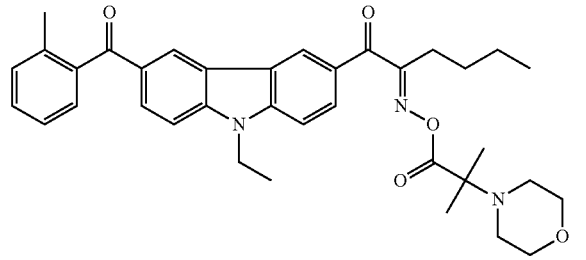
(A-54)
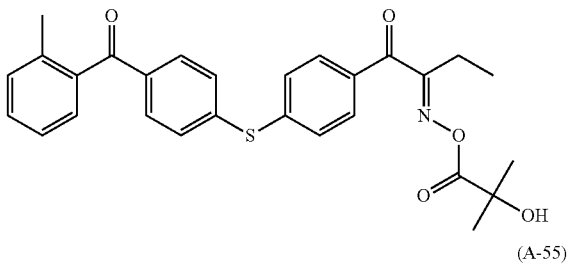
(A-55)
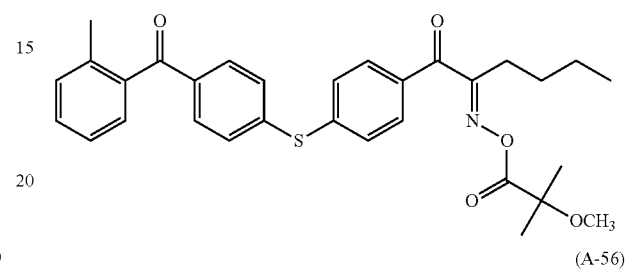
(A-56)
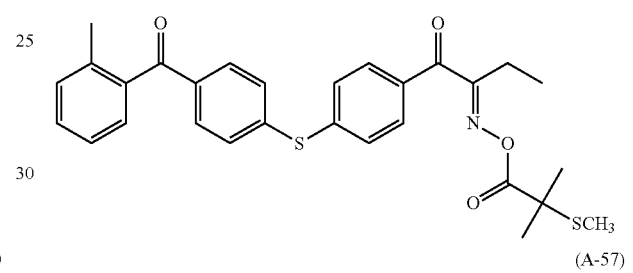
(A-57)
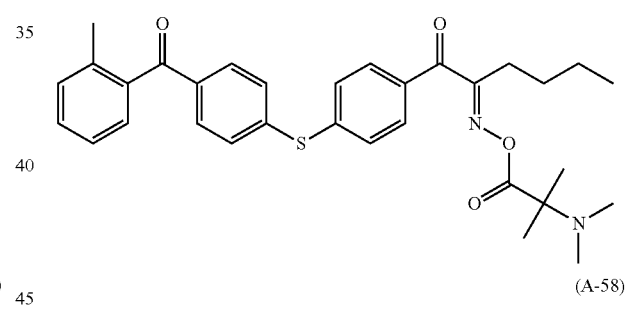
(A-58)
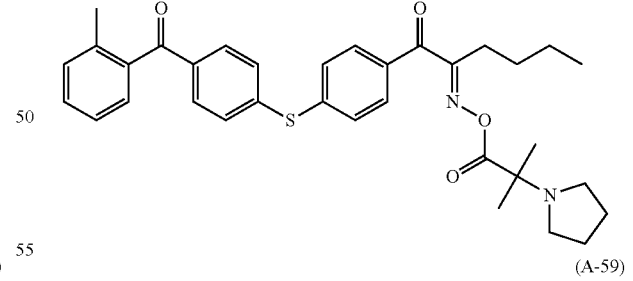
(A-59)
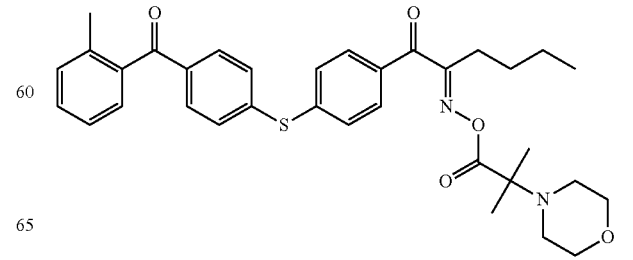

-continued (A-60)
(A-61)
(A-62)
(A-63)
(A-64)
(A-65)
(A-66)

-continued (A-67)
(A-68)
(A-69)
(A-70)
(A-71)
(A-72)

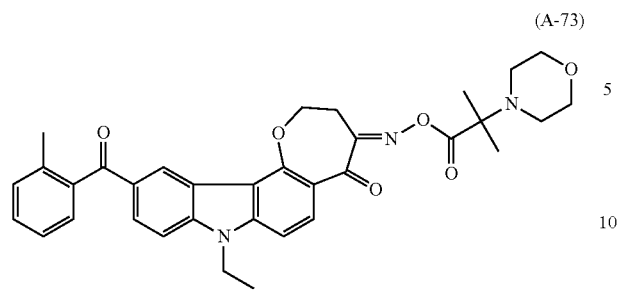
(A-73)
(A-74)
(A-75)
(A-76)
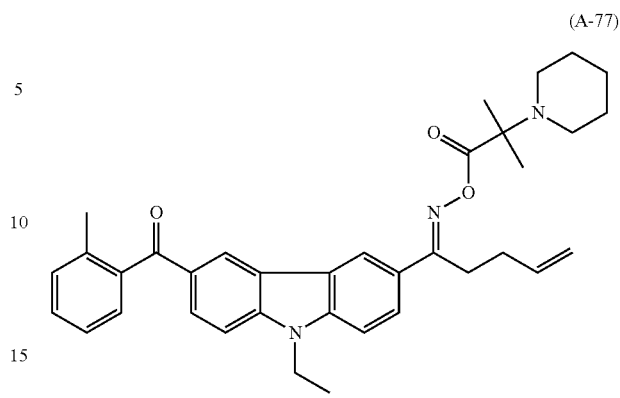
(A-77)
(A-78)
(A-79)
(A-80)

-continued
(A-81)
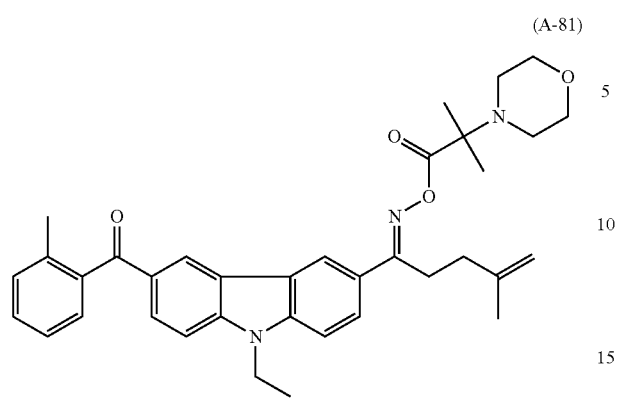
(A-82)
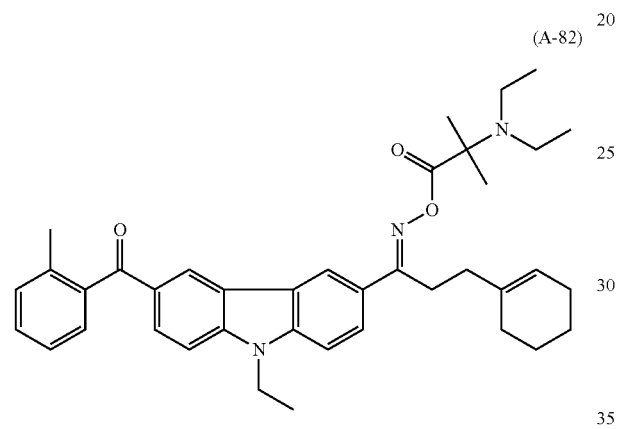
(A-83)
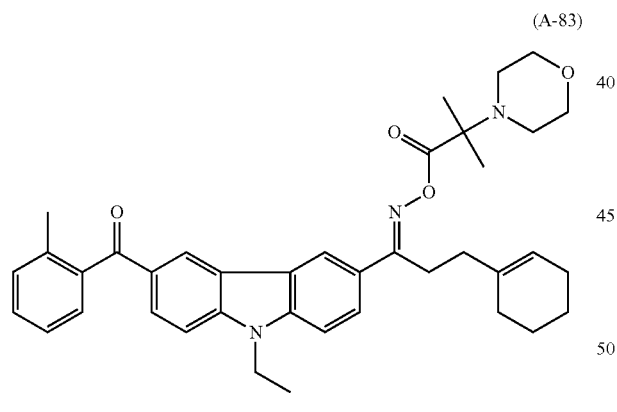
(A-84)
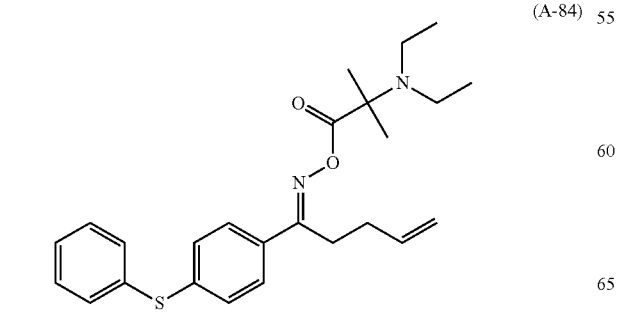
-continued
(A-85)
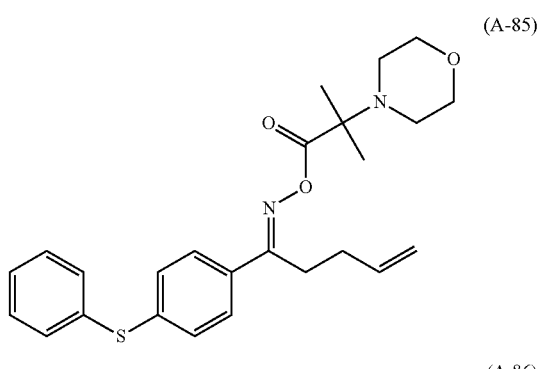
(A-86)
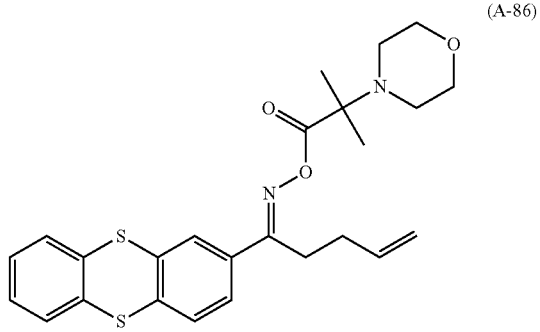
(A-87)
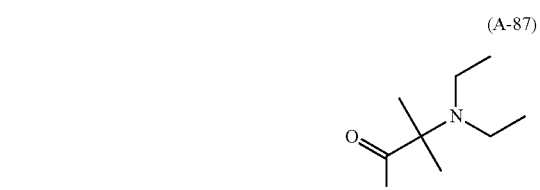
(A-88)
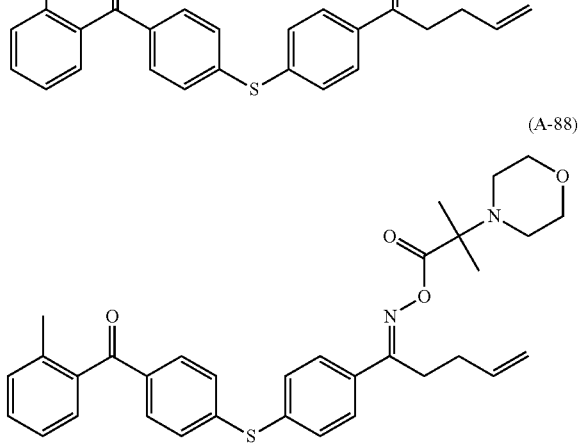
(A-89)
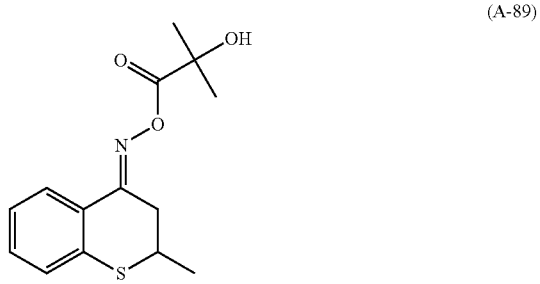

(A-90) 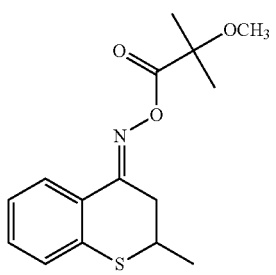
(A-91) 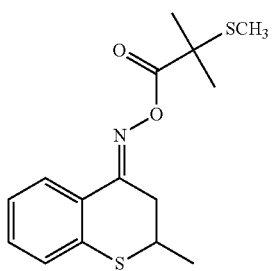
(A-92) 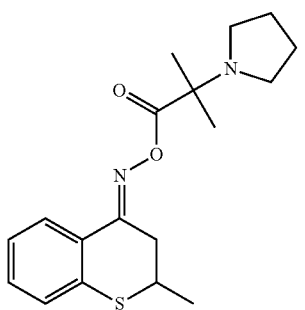
(A-93) 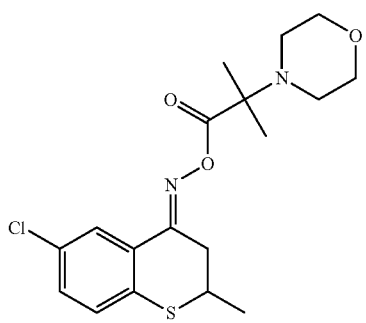
(A-94) 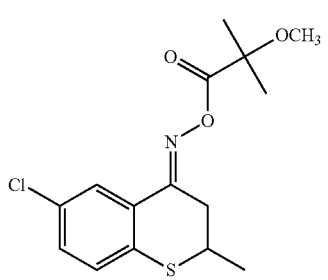
(A-95) 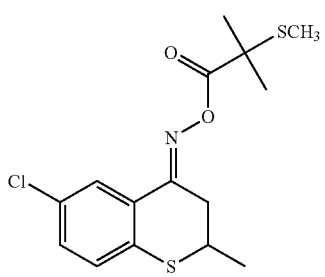
(A-96) 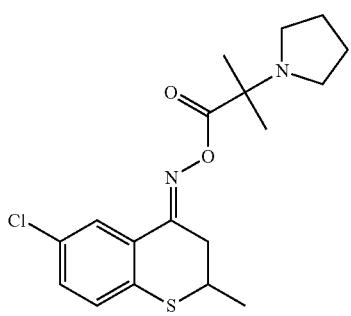
(A-97) 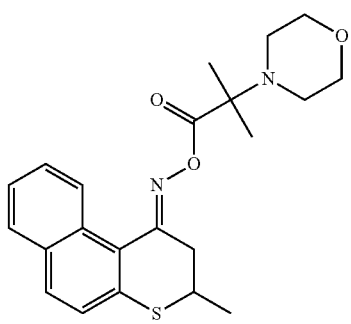
(A-98) 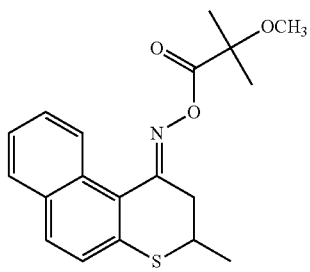
(A-99) 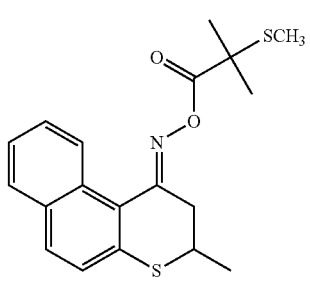

(A-100)
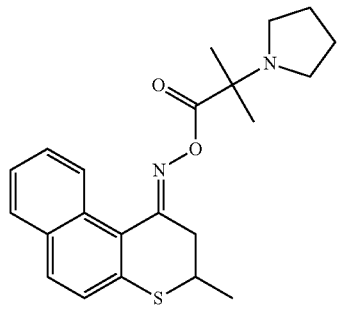
(A-101)
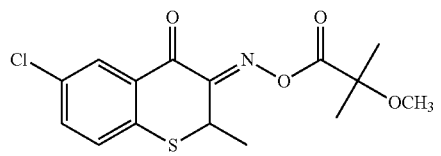
(A-102)
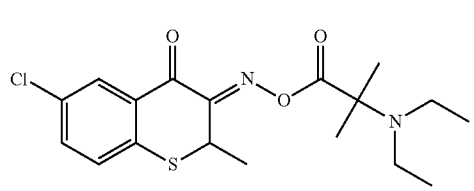
(A-103)
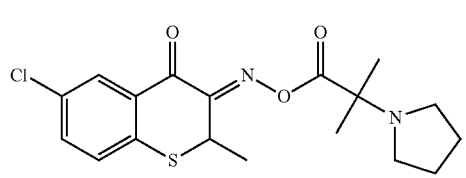
(A-104)
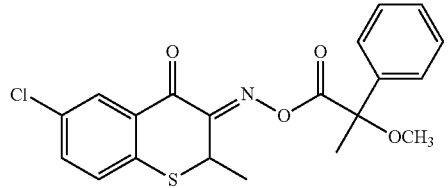
(A-105)
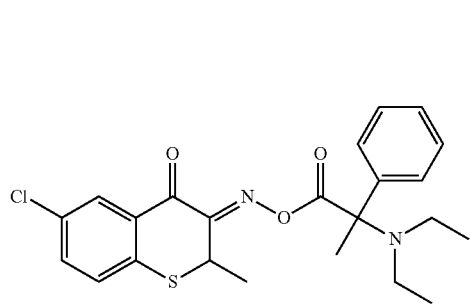
(A-106)
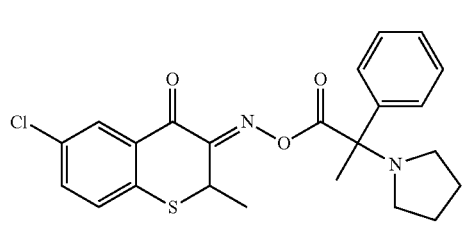
(A-107)
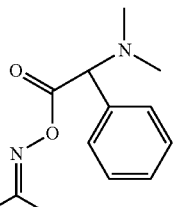
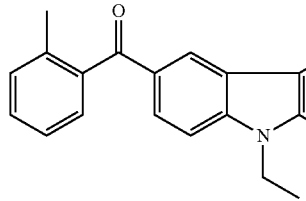
(A-108)
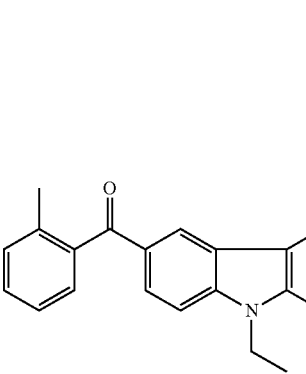
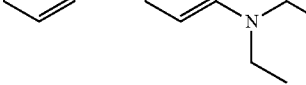
(A-109)
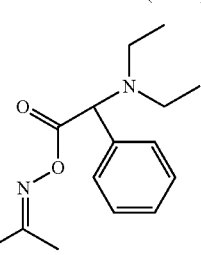
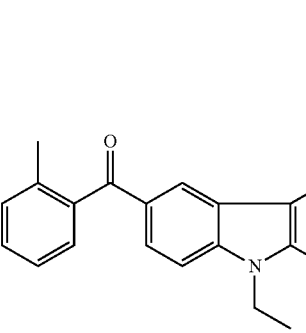
(A-110)
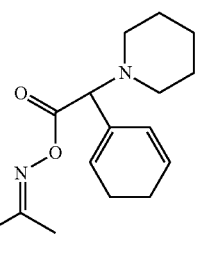
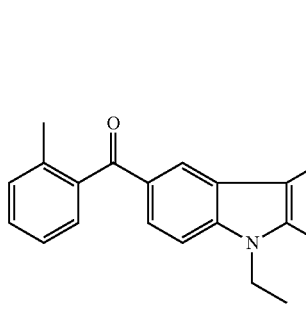

(A-111)
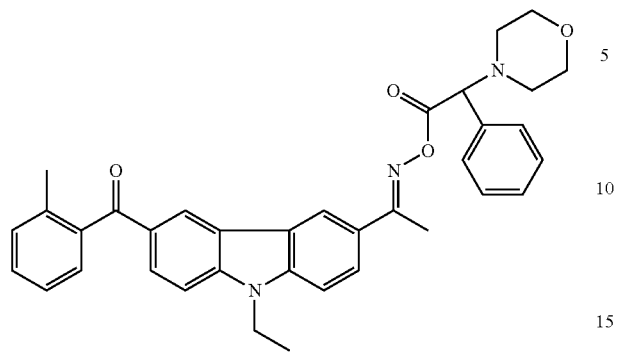
(A-115)
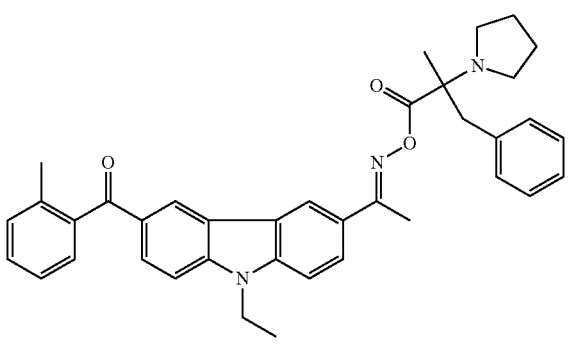
(A-112)
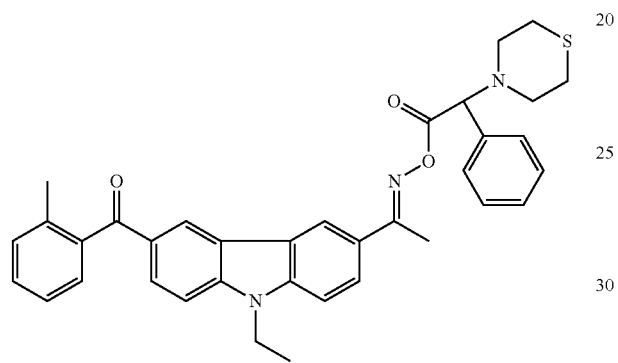
(A-116)
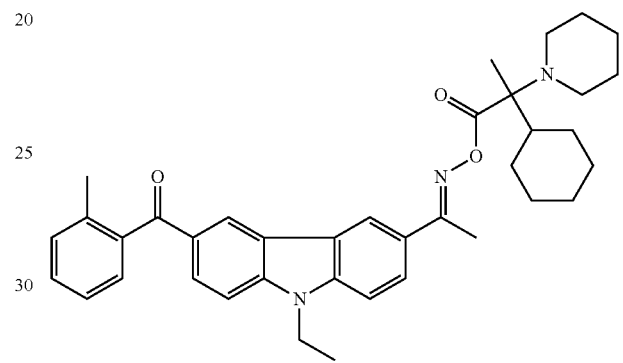
(A-113)
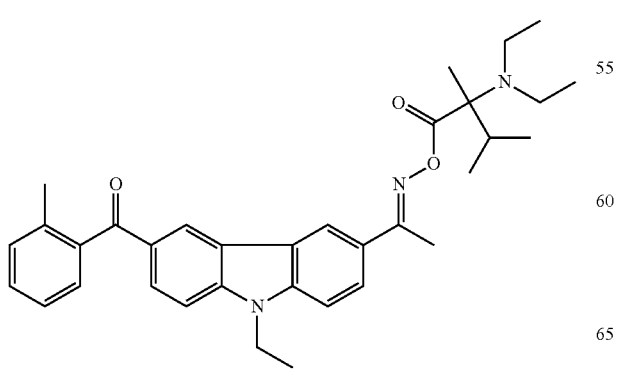
(A-119)
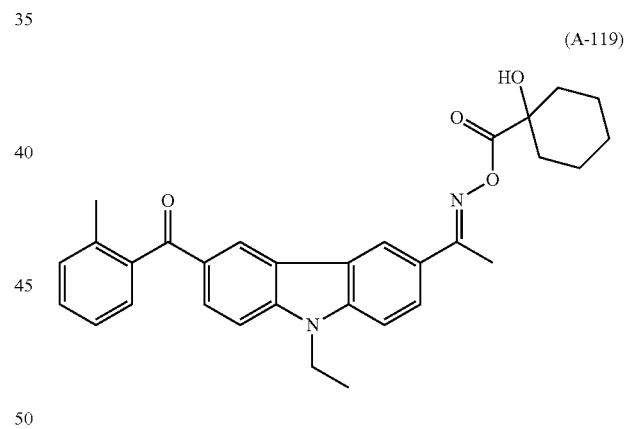
(A-114)
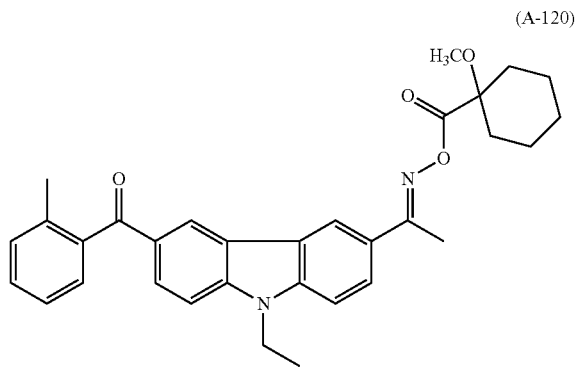
(A-120)

(A-121) 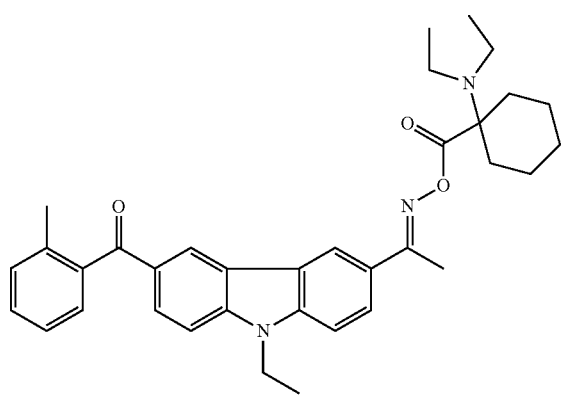
(A-122) 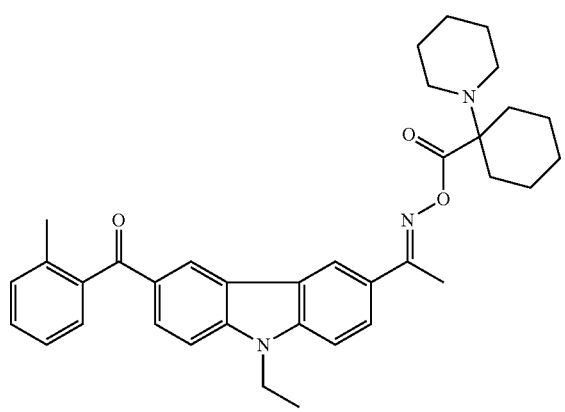
(A-123) 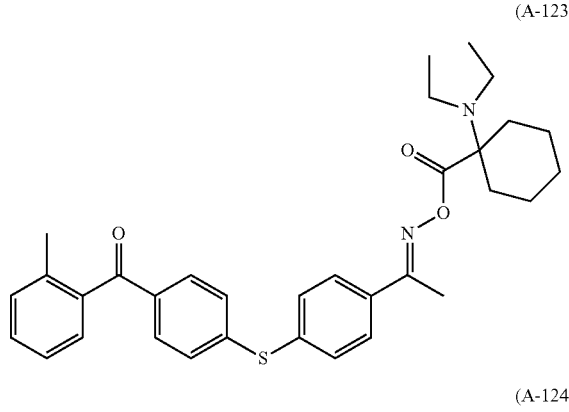
(A-124) 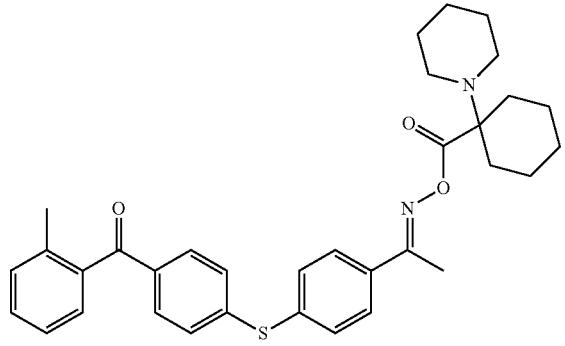
(A-125) 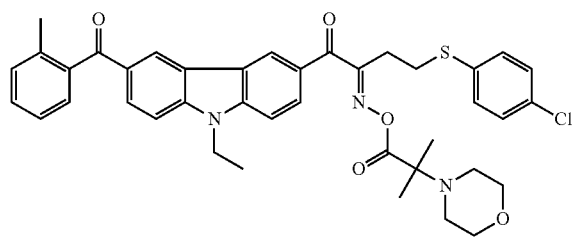
(A-126) 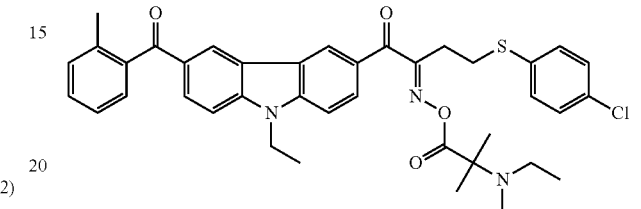
(A-127) 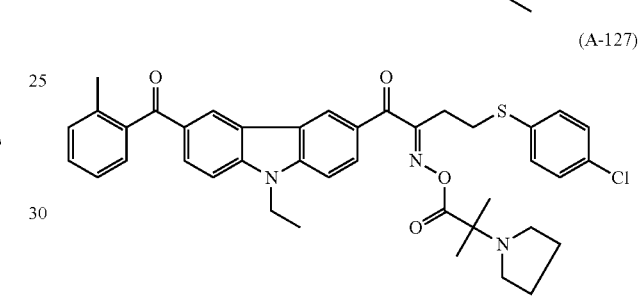
(A-128) 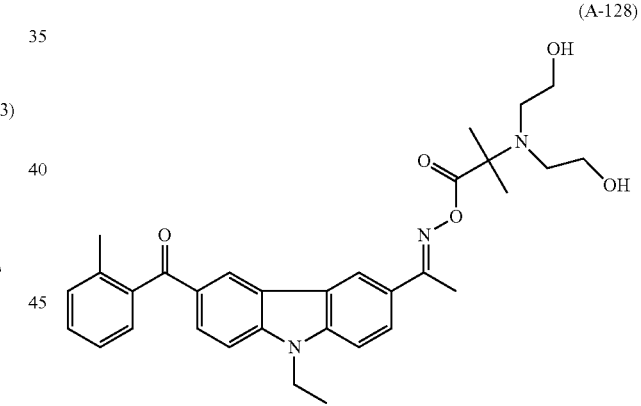
(A-129) 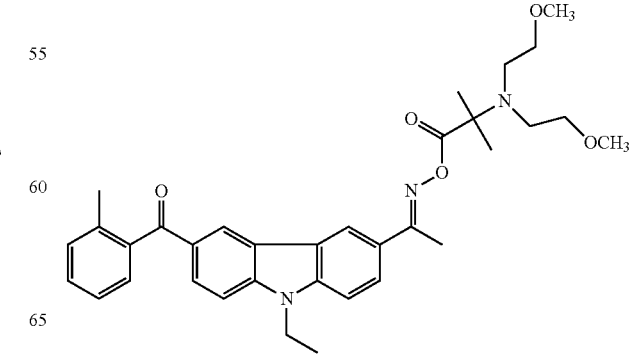

(A-130)

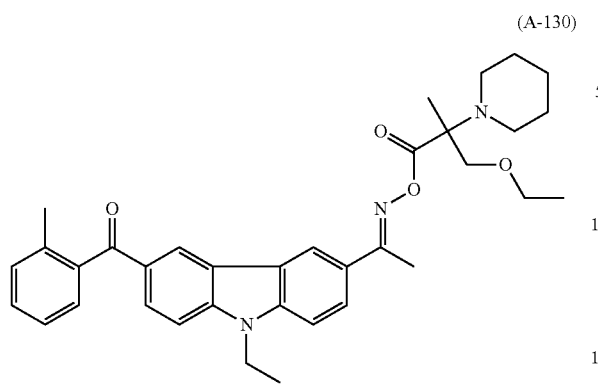

(A-131)

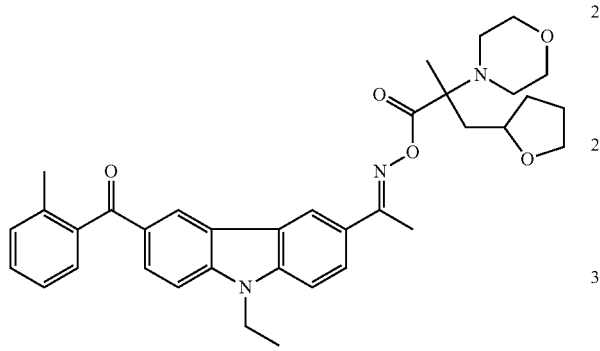

(A-132)

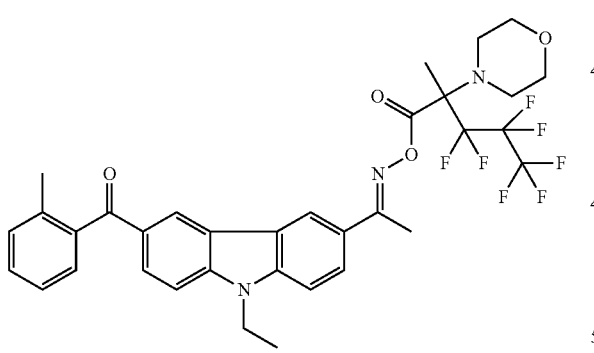

(A-133)

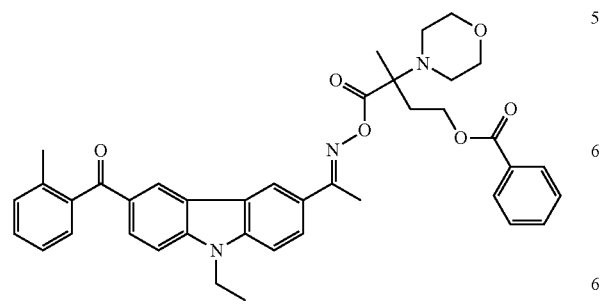

(A-134)

(A-135)

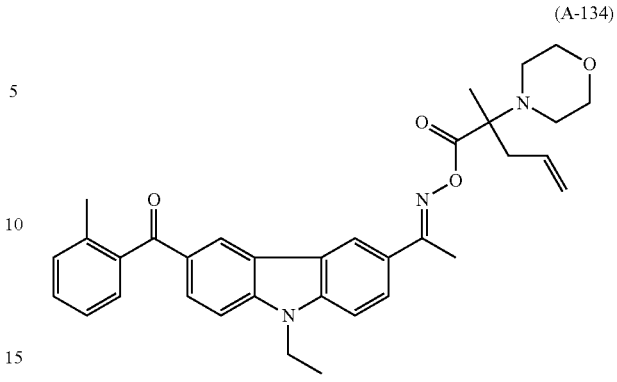

Among the above described exemplary compounds (A-1) to (A-135), the compounds (A-29) to (A-135) are more preferred from the viewpoint of the molar extinction coefficient at 365 nm.

The specific oxime compound in the invention addition, when added to the photopolymerizable composition of the invention as stated above, is also applicable to the curable materials for the uses as described below by utilizing the photopolymerization initiation function of the compound.

Namely, for example, as illustrated below, examples of various uses include: printing ink materials (for example, use for the screen process printing ink, use for offset or flexographic printing ink, and use for UV curable ink); white or color finishing materials for lumber or metal, powder coating materials (particularly, use for coating materials for paper, lumber, metal or plastic); marking materials for building or road; holographic recording materials, image recording materials, materials for a recording layer of a planographic printing plate precursor capable of being developed with an organic solvent or aqueous alkali, or photo-curable coating materials for manufacturing screen printing mask, each of which uses a photographic reproduction technique; dental filling compositions, adhesives, pressure-sensitive adhesives, laminate resin materials, etching resist materials for both the liquid and dry thin-film; solder resist materials; electroplating resist materials; permanent resist materials; photoformable dielectric materials for printed circuit boards or electronic circuits; various display materials; optical switch materials, optical grid (interference grid) forming materials, optical circuit-manufacturing materials, three-dimensional article-manufacturing materials using bulk curing (UV-curing with transparent forming die) or stereolithographic techniques, (for example, materials recited in U.S. Pat. No. 4,575,330); composite materials (for example, styrene polyester which can contain glass fibers and/or other fibers and other auxiliaries, if needed) and other thick layer composition manufacturing materials; resist materials for coating or sealing electronic components and integrated circuits; optical fiber forming materials, coating materials for manufacturing optical lenses (for example, contact lenses or Fresnel lenses); materials for manufacturing medical devices, care aids or implants, and gel manufacturing materials having thermotropic properties as described in German Patent No. 19,700,064 and European Patent No. 678,534.

The specific oxime compound can also be utilized as dose-detecting materials and photoresist materials for semiconductor manufacture, TFT manufacture, color filter manufacture, micromachine component manufacture and the like.

The photopolymerizable composition of the present invention is formed by including (A) the specific oxime compound and (B) a polymerizable compound, which will be described later. The function of (A) the specific oxime compound makes it possible to form a cured film, which has high sensitivity to light having wavelengths of 365 nm and 405 nm, excellent storage stability, and further capability of suppressing coloration caused by heat-aging. Although the details of the mechanism are not clear, it is thought that since (A) the specific oxime compound absorbs light owing to the molecular structure thereof, and the recombination of radicals at the time of cleavage is suppressed, the quantity of the generated radicals is large, thereby achieving higher sensitivity. Further, since the radical recombination is suppressed, it is thought that the reaction among each of the decomposition products of the specific oxime compound at the time of heat-aging is suppressed, thereby suppressing the coloration resulting from the reaction.

In the present invention, in order to evaluate the coloration due to heat-aging of the cured film formed from the polymerizable composition of the invention, the color difference $\Delta Eab^*$ can be used. Here, the color difference $\Delta Eab^*$ may be measured using MCPD-3000 manufactured by Otsuka Electronics Co., Ltd.

As the conditions in the evaluation, first, the polymerizable composition of the present invention is exposed to light at 385 nm with various exposure amounts in the range of from 10 mJ/cm$^2$ to 2,500 ml/cm$^2$ by using an ultra high pressure mercury lamp proximity type exposure machine (manufactured by Hitachi High-Tech Electronics Engineering Co., Ltd.), or an i-line stepper exposure machine FPA-3000i5+ (manufactured by Canon Inc.) to form a cured film. Further, if needed, after developing, the cured film is heated at 200° C. for one hour.

The color difference $\Delta Eab^*$ of the cured film before and after the heating is measured, so that the change of the coloration state of the cured film due to heat-aging can be evaluated.

The photopolymerizable composition of the present invention makes it possible to set the color difference $\Delta Eab^*$ before heating and after heating to 5 or less.

Hereinafter, the photopolymerizable composition of the invention is explained in detail by reference to a photopolymerizable composition (1) which can be suitably used for forming colored areas and the like in a color filter (if needed, which may be referred to as a photopolymerizable composition for color filter hereinafter), and a polymerizable composition (2) which can be suitably used for forming a photosensitive layer and the like of a planographic printing plate precursor by way of example, but the uses of the photopolymerizable compositions of the invention are not limited to them, as described above.

Photopolymerizable Composition (1): Photopolymerizable Composition for Color Filter Since the photopolymerizable composition for a color filter is used for the purpose of forming a colored area used for the color filter, the composition includes (A) a specific oxime compound, (B) a polymerizable compound, and if needed, (C) a colorant. Hereinafter, each component that forms the photopolymerizable composition for a color filter is described.

(1)-(A) Specific Oxime Compound (A) The specific oxime compound contained in the photopolymerizable composition (1) functions as a polymerization initiator in the composition. The detail of (A) the specific oxime compound is as described above.

The content of the specific oxime compound in the a polymerizable composition (1) is preferably from 0.5% by mass to 40% by mass, more preferably from 1% by mass to 35% by mass, and sill more preferably from 1.5% by mass to 30% by mass, relative to the total solid content of the composition.

The total solid content of the photopolymerizable composition herein means the total mass of the ingredients except that a solvent is removed from the photopolymerized composition.

When the content is in this range, the photopolymerizable composition layer has a high sensitivity upon exposure to light, and at the same time an appropriate hardness of the cured film is obtained, and a pattern having a favorable patternability when a pattern is formed and having a high strength is obtained.

The specific oxime compound may be used alone, or may be used in combination of two or more kinds thereof.

Other Photopolymerization Initiators

In the photopolymerizable composition (1), a known photopolymerization initiator other than the specific oxime compound may be used together with the specific oxime compound to the extent that the effect of the invention is not impaired. In this case, the known photopolymerization initiator is preferably used in the range of 50% by mass or less relative to the specific oxime compound.

The photopolymerization initiator, which can be used together, is a compound that decomposes with light, and initiates and promotes polymerization of the polymerizable compound, which will be described later, and it is preferable that the photopolymerization initiator have an absorption in the range of the wavelengths of from 300 nm to 500 nm. Specifically, examples of the photopolymerization initiator include organic halide compounds, oxydiazole compounds, carbonyl compounds, ketal compounds, benzoin compounds, acridine compounds, organic peroxide compounds, azo compounds, coumarin compounds, azide compounds, metallocene compounds, biimidazole compounds, organic boric acid compounds, disulfonic acid compounds, onium salt compounds, and acyl phosphine(oxide) compounds.

(1)-(B) Polymerizable Compound

A polymerizable compounds, which can be used for the photopolymerizable composition (1), is an addition-polymerizable compound having at least one ethylenic unsaturated double bond, and is selected from compounds having at least one ethylenic unsaturated double bond at a terminal thereof, and preferably two or more unsaturated double bonds at terminals thereof. Such compounds are widely known in the art, and can be used in the invention without particular limitation. These compounds have chemical forms such as monomers or prepolymers, namely, dimers, trimers, and oligomers, or the mixtures thereof, and the copolymers thereof, for example. Examples of monomers or the copolymers thereof include unsaturated carboxylic acid (for example, acrylic acid, methacrylic acid, itaconic acid, crotonic acid, isocrotonic acid, maleic acid, and the like), esters thereof and amides thereof. Further, esters of an unsaturated carboxylic acid and an aliphatic polyhydric alcohol compound and amides of an unsaturated carboxylic acid and an aliphatic polyvalent amine compound are preferably used. Further, addition reaction products of unsaturated carboxylic acid esters or unsaturated carboxylic acid amides, which have a nucleophilic substituent such as a hydroxyl group, an amino group or a mercapto group, with monofunctional or polyfunctional isocyanates or epoxys, and dehydration condensation products with monofunctional or polyfunctional carboxylic acids, are also preferably used. Moreover, the addition reaction products of unsaturated carboxylic acid esters or unsaturated carboxylic acid amides, which have an electrophilic substituent such as an isocyanate group or an epoxy group, with monofunctional or polyfunctional alcohols, amines or thiols; and substitution reaction products of unsaturated carboxyl acid esters or unsaturated carboxyl acid amides, which have a releasable substituent such as a halogen group or a tosyloxy group, with monofunctional or polyfunctional alcohols, amines or thiols; are also preferable. Furthermore, as another example, compounds, in which the unsaturated carboxylic acid is replaced with an unsaturated phosphonic acid, styrene, a vinyl ether or the like, can also be used.

Specific examples of the monomers of esters of aliphatic polyhydric alcohol compounds and unsaturated carboxylic acids include: acrylic esters such as ethylene glycol diacrylate, triethylene glycol diacrylate, 1,3-butanediol diacrylate, tetramethylene glycol diacrylate, propylene glycol diacrylate, neopentylglycol diacrylate, trimethylolpropane triacrylate, trimethylol propane-tri(acryloyloxypropyl)ether, trimethylolethane triacrylate, hexanediol diacrylate, 1,4-cyclohexanediol diacrylate, tetraethylene glycol diacrylate, pentaerythritol diacrylate, pentaerythritol triacrylate, pentaerythritol tetraacrylate, dipentaerythritol diacrylate, dipentaerythritol hexaacrylate, sorbitol triacrylate, sorbitol tetraacrylate, sorbitol pentaacrylate, sorbitol hexaacrylate, tri(acryloyloxyethyl)isocyanurate, polyester acrylate oligomer and isocyanuric acid EO-modified triacrylate;

methacrylates such as tetramethylene glycol dimethacrylate, triethylene glycol dimethacrylate, neopentylglycol dimethacrylate, trimethylolpropane trimethacrylate, trimethylolethane trimethacrylate, ethylene glycol dimethacrylate, 1,3-butanediol dimethacrylate, hexanediol dimethacrylate, pentaerythritol dimethacrylate, pentaerythritol trimethacrylate, pentaerythritol tetramethacrylate, dipentaerythritol dimethacrylate, dipentaerythritol hexamethacrylate, sorbitol trimethacrylate, sorbitol tetramethacrylate, bis[p-(3-methacryloxy-2-hydroxypropoxy)phenyl] dimethylmethane, and bis-[p-(methacryloxyethoxy)phenyl] dimethylmethane;

itaconates such as ethylene glycol diitaconate, propylene glycol diitaconate, 1,3-butanediol diitaconate, 1,4-butanediol diitaconate, tetramethylene glycol diitaconate, pentaerythritol diitaconate, and sorbitol tetraitaconate;

crotonates such as ethylene glycol dicrotonate, tetramethylene glycol dicrotonate, pentaerythritol dicrotonate, and sorbitol tetradicrotonate;

isocrotonates such as ethylene glycol diisocrotonate, pentaerythritol diisocrotonate, and sorbitol tetraisocrotonate; and maleates such as ethylene glycol dimaleate, triethylene glycol dimaleate, pentaerythritol dimaleate, and sorbitol tetramaleate.

Examples of other esters which can be preferably used include: aliphatic alcohol esters as described in Japanese Examined Patent Application Publication (JP-B) No. 51-47334 and JP-A No. 57-196231; esters having an aromatic skeleton as described in JP-A No. 59-5240, JP-A No. 59-5241 and JP-A No. 2-226149; and esters having an amino group as described in JP-A No. 1-165613. The ester monomers as described above can be used as mixtures.

Further, specific examples of monomers of amides of an aliphatic polyvalent amine compound and an unsaturated carboxylic acid include methylenebis-acrylamide, methylenebis-methacrylamide, 1,6-hexamethylenebis-acrylamide, 1,6-hexamethylenebis-methacrylamide, diethylene triamine trisacrylamide, xylylenebisacrylamide, and xylylenebismethacrylamide.

Preferable examples of other desirable amide monomers include monomers having a cyclohexylene structure as recited in JP-B No. 54-21726.

Moreover, urethane addition-polymerizable compounds produced by using the addition reaction of an isocyanate and a hydroxyl group are also suitable, and specific examples of such compounds include vinyl urethane compounds containing two or more polymerizable vinyl groups in a molecule, as recited in JP-B No. 48-41708, the vinyl urethane compounds being formed by adding a hydroxyl group-containing vinyl monomer represented by the following Formula (A) to a polyisocyanate compound having two or more isocyanate groups in a molecule.

$$CH_2=C(R^4)COOCH_2CH(R^5)OH \quad (A)$$

Wherein, in Formula (A), $R^4$ and $R^5$ each represent H or $CH_3$.

Further, urethane acrylates as recited in JP-A No. 51-37193, JP-B No. 2-32293, and JP-B No. 2-16765, and urethane compounds having an ethylene oxide skeleton as recited in JP-B No. 58-49860, JP-B No. 56-17654, JP-B No. 62-39417, and JP-B No. 62-39418 are also preferable. Furthermore, by using addition-polymerizable compounds having an amino structure or a sulfide structure in a molecule as recited in JP-A No. 63-277653, JP-A No. 63-260909 and JP-A No. 1-105238, a photopolymerizable composition having extremely high photosensitive speed can be obtained.

Other examples include polyfunctional acrylates or methacrylates such as polyester acrylates as recited in JP-A No. 48-64183, JP-B No. 49-43191 and JP-B No. 52-30490, and epoxyacrylates formed by reacting an epoxy resin with (meth)acrylic acid. Further, other examples include certain unsaturated compounds as recited in JP-B No. 46-43946, JP-B No. 1-40337, and JP-B No. 1-40336, and vinyl sulfonic acid compounds as recited in JP-A No. 2-25493. Moreover, in some cases, a structure containing a perfluoroalkyl group as recited in JP-A No. 61-22048 may preferably be used. In addition, photocurable monomers and oligomers as recited in Journal of the Adhesion Society of Japan, Vol. 20, No. 7, pp. 300-308 (1984) can also be used.

Details of the method of the uses of the addition-polymerizable compounds, such as the structure thereof, the single use or combined use, or the addition amount of the compound, can be arbitrarily determined in accordance with the aimed design of the performance of the photopolymerizable composition. For example, the addition-polymerizable compound is selected from the following point of view.

In view of the sensitivity, the structure having a high content of unsaturated groups per one molecule is desirable, and in many cases, a bifunctional or higher functional structure is desirable. Further, in order to make the strength of a cured film high, a trifunctional or higher functional structure is preferable. Furthermore, a method of using compounds having different functionalities and/or different polymerizable groups (for example, an acrylic ester, a methacrylic ester, a styrene compound, and a vinyl ether compound) in combination is also effective in controlling both the sensitivity and the strength.

Moreover, in view of both the compatibility and the dispersibility with other components (for example, a photopolymerization initiator, a colorant (a pigment or a dye) and the like, and binder polymer and the like) in the photopolymerizable composition, both the selection and the use method of addition polymerizable compounds are important factors, and, for example, in some cases, the compatibility may be enhanced by using a low purity compound or using in combination of two or more kinds of compounds. Further, for the purpose of increasing the adhesion to a hard surface of a support and the like, a compound having a specific structure may be selected.

The content of the polymerizable compound in the polymerizable composition (1) is preferably from 1 to 90% by mass, more preferably from 2 to 70% by mass, and still more preferably from 3 to 50% by mass, relative to the total solid content of the composition.

The polymerizable compound may be used singly or may be used in combination of two or more kinds.

(1)-(C) Colorant

The photopolymerizable composition (1) may include (C) the colorant. By containing a colorant, the colored photopolymerizable composition with a desired color can be obtained.

In addition, since the photopolymerizable composition (1) contains the specific oxime compound that is (A) the polymerization initiator that is used in the invention and has high sensitivity to a light source having wavelengths of 365 nm and 405 nm as a short wavelength light source, the photopolymerizable composition can be cured at high sensitivity even in the case where the colorant is contained therein at high concentration.

The colorant used in the photopolymerizable composition (1) is not particularly restricted to, but one kind of conventionally known various dyes or pigments can be used alone, or a mixture of two or more kinds thereof may be used, and the colorant is suitably selected in accordance with the intended use of the photopolymerizable composition. In the case where the photopolymerizable composition of the invention is used for manufacturing a color filter, any of the colorants (chromatic colorant) of the chromatic color system such as R, G, B or the like, which form color pixels of the color filter, and the colorant (black colorant) of the black system generally used for black matrix formation, can be used.

Since the photopolymerizable composition of the invention containing (A) the specific oxime compound can be cured at high sensitivity even when the light quantity for exposure is small, the photopolymerizable composition can be particularly preferably used for a black colorant-containing photopolymerizable composition, through which light is hardly transmitted.

Hereinafter, the colorant applicable to the polymerizable composition (1) is explained by reference to a colorant suitable for the use of a color filter as an example.

As the chromatic color pigment, various kinds of conventionally known inorganic pigments or organic pigments can be used. Further, considering that the pigment has preferably high transmittance regardless of inorganic pigments or organic pigments, pigment particles having a small particle size as fine as possible are preferably used, and in view of handling property, the average primary particle diameter of the pigment is preferably from 0.01 μm to 0.1 μm, and more preferably from 0.01 μm to 0.05 μm.

Examples of the inorganic pigments include metal compounds such as metal oxides or metal complexes, and specific examples thereof include metal oxides of iron, cobalt, aluminum, cadmium, lead, copper, titanium, magnesium, chromium, zinc, antimony, or the like and composite oxides of these metals.

Examples of the pigments which can be preferably used in the invention include the following pigments. However, the invention is not limited to these examples.

C.I. Pigment Yellow 1, 2, 3, 4, 5, 6, 10, 11, 12, 13, 14, 15, 16, 17, 18, 20, 24, 31, 32, 34, 35, 35:1, 36, 36:1, 37, 37:1, 40, 42, 43, 53, 55, 60, 61, 62, 63, 65, 73, 74, 77, 81, 83, 86, 93, 94, 95, 97, 98, 100, 101, 104, 106, 108, 109, 110, 113, 114, 115, 116, 117, 118, 119, 120, 123, 125, 126, 127, 128, 129, 137, 138, 139, 147, 148, 150, 151, 152, 153, 154, 155, 156, 161, 162, 164, 166, 167, 168, 169, 170, 171, 172, 173, 174, 175, 176, 177, 179, 180, 181, 182, 185, 187, 188, 193, 194, 199, 213, 214, or the like C.I. Pigment Orange 2, 5, 13, 16, 17:1, 31, 34, 36, 38, 43, 46, 48, 49, 51, 52, 55, 59, 60, 61, 62, 64, 71, 73

C.I. Pigment Red 1, 2, 3, 4, 5, 6, 7, 9, 10, 14, 17, 22, 23, 31, 38, 41, 48:1, 48:2, 48:3, 48:4, 49, 49:1, 49:2, 52:1, 52:2, 53:1, 57:1, 60:1, 63:1, 66, 67, 81:1, 81:2, 81:3, 83, 88, 90, 105, 112, 119, 122, 123, 144, 146, 149, 150, 155, 166, 168, 169, 170, 171, 172, 175, 176, 177, 178, 179, 184, 185, 187, 188, 190, 200, 202, 206, 207, 208, 209, 210, 216, 220, 224, 226, 242, 246, 254, 255, 264, 270, 272, 279

C.I. Pigment Green 7, 10, 36, 37, 58

C.I. Pigment Violet 1, 19, 23, 27, 32, 37, 42

C.I. Pigment Blue 1, 2, 15, 15:1, 15:2, 15:3, 15:4, 15:6, 16, 22, 60, 64, 66, 79, 80

C.I. Pigment Black 1

These organic pigments can be used alone, or in combination of various kinds of pigments for the purpose of increasing the color purity.

Further, as a pigment for a black matrix, carbon black, titanium black, iron oxide, and titanium oxide are used singly or mixtures thereof are used, and the combination of carbon black and titanium black is desirable. The mass ratio of carbon black and titanium black is preferably in the range of from 100:0 to 100:60, from the viewpoint of dispersion stability.

Titanium black dispersion is explained in detail below.

The titanium black dispersion refers to a dispersion in which titanium black is contained as a colorant.

By incorporating titanium black as a titanium black dispersion, which has been prepared beforehand, in the polymerizable dispersion, both dispersibility and dispersion stability of titanium black can be improved.

Hereafter, the titanium black is explained.

Titanium Black

The titanium black which can be used in the invention is black particles having a titanium atom, and is preferably low-order titanium oxide, titanium oxynitride or the like. The surface of the titanium black particles may be modified in accordance with the intended use such as improvement of dispersibility, suppression of cohesive property or the like. The surface may be covered with silicon oxide, titanium oxide, germanium oxide, aluminum oxide, magnesium oxide, or zirconium oxide, and, alternatively, may be subjected to a treatment with a water-repellent substance as described in JP-A No. 2007-302836.

The particle diameter of titanium black particles is not specifically restricted to, but from the viewpoints of the dispersibility and coloration, the particle diameter is preferably from 3 nm to 2,000 nm, more preferably from 10 nm to 500 nm, and still preferably from 20 nm to 200 nm.

The specific surface area of titanium black is not specifically restricted to, but, the specific surface area measured by a BET method is usually from about 5 m$^2$/g to 150 m$^2$/g, and preferably from about 20 m$^2$/g to 100 m$^2$/g, whereby the water repellency after such titanium black has been subjected to a surface treatment with a water repellent agent becomes predetermined capability.

Examples of commercial products of titanium black include, but are not limited to, titanium black 10S, 12S, 13R, 13M, 13 M-C, 13R, and 13 R-N (manufactured by Mitsubishi Materials Corporation) and TILACK D (manufactured by Ako Kasei Co., Ltd.).

In the photopolymerizable composition (1), when the colorant is a dye, a colored composition can be obtained in the state where the dye is uniformly dissolved in the composition.

As the colorants which can be used in the photopolymerizable composition (1), dyes previously known as those for color filters can be used without particular limitation. Examples of the dyes include pyrazoleazo dyes, anilinoazo dyes, triphenylmethane dyes, anthraquinone dyes, anthrapyridone dyes, benzylidene dyes, oxonole dyes, pyrazolotriazole dyes, pyridoneazo dyes, cyanine dyes, phenothiazine dyes, pyrrolopyrazol azomethine dyes, xanthene dyes, phthalocyanine dyes, benzopyrane dyes, and indigo dyes.

In the case in which development is performed using water or alkali, an acid dye and/or a derivative thereof may suitably be used from the viewpoint of completely removing a binder and/or a dye in the unexposed area by the development.

In addition, direct dyes, basic dyes, mordant dyes, acid mordant dyes, azoic dyes, disperse dyes, oil-soluble dyes, edible dyes, and/or the derivatives thereof can usefully be used.

Specific examples of the acid dye include, but are not limited to, the following dyes: Acid Alizarin Violet N: Acid Black 1, 2, 24, 48; Acid Blue 1, 7, 9, 15, 18, 23, 25, 27, 29, 40, 45, 62, 70, 74, 80, 83, 86, 87, 90, 92, 103, 112, 113, 120, 129, 138, 147, 158, 171, 182, 192, 243, 324:1; Acid Chrome Violet K; Acid Fuchsin; Acid Green 1, 3, 5, 9, 16, 25, 27, 50; Acid Orange 6, 7, 8, 10, 12, 50, 51, 52, 56, 63, 74, 95; Acid Red 1, 4, 8, 14, 17, 18, 26, 27, 29, 31, 34, 35, 37, 42, 44, 50, 51, 52, 57, 66, 73, 80, 87, 88, 91, 92, 94, 97, 103, 111, 114, 129, 133, 134, 138, 143, 145, 150, 151, 158, 176, 183, 198, 211, 215, 216, 217, 249, 252, 257, 260, 266, 274; Acid Violet 6B, 7, 9, 17, 19; Acid Yellow 1, 3, 7, 9, 11, 17, 23, 25, 29, 34, 36, 42, 54, 72, 73, 76, 79, 98, 99, 111, 112, 114, 116, 184, 243; Food Yellow 3; and derivatives of these dyes.

Further, azo-based, xanthene-based, and phthalocyanine-based acid dyes other than the above are also preferable, and, for example, the acid dyes such as C.I. Solvent Blue 44 and 38; C.I. Solvent Orange 45; Rhodamine B, Rhodamine 110 and the like, and derivatives of these dyes are also preferably used.

Among them, the colorant is preferably selected from triallyl methane dyes, anthraquinone dyes, azomethine dyes, benzylidene dyes, oxonole dyes, cyanine dyes, phenothiazine dyes, pyrrolopyrazol azomethine dyes, xanthene dyes, phthalocyanine dyes, benzopyrane dyes, indigo dyes, pyrazoleazo dyes, anilinoazo dyes, pyrazolotriazole dyes, pyridoneazo dyes, anthrapyridone dyes and pyrromethene dyes.

The colorants which can be used in the photopolymerizable composition (1) are preferably dyes or pigments. Especially are preferred pigments whose average particle diameter (r) satisfies the following range: 20 nm≤r≤300 nm, more preferably 125 nm≤r≤250 nm, and particularly preferably 30 nm≤r≤200 nm. By using a pigment having such an average particle diameter (r), pixels having a high contrast ratio and a high light transmittance can be obtained. The term "average particle diameter" herein means the average particle diameter of secondary particles, in which primary particles (single crystallite) of the pigment are aggregated.

Further, in the particle diameter distribution of secondary particles of pigment that can be used in the invention (hereinafter, simply refers to as "particle diameter distribution"), it is desirable that the secondary particles within the range of (average particle diameter ±100) nm are 70% by mass or more, and preferably 80% by mass or more, with respect to the total mass of the secondary particles.

The pigments having the above-described average particle diameter and particle diameter distribution may be prepared by pulverizing while mixing and dispersing a commercially available pigment with, as required, other pigments (having an average particle diameter usually exceeding 300 nm), preferably as a mixture of the pigments mixed with a dispersant and a solvent, by using, for example, a grinder such as a bead mill or a roll mill. The pigment obtained in this way usually takes the form of pigment dispersion.

The content of the colorant contained in the photopolymerizable composition (1) is preferably from 20% by mass to 95% by mass, more preferably from 25% by mass to 90% by mass, and still more preferably from 30% by mass to 80% by mass, with respect to the total solid content of the photopolymerizable composition.

By setting the content of the colorant within the above range, suitable chromaticity can be obtained when a color filter is manufactured by using the photopolymerizable composition (1). Further, since light curing can sufficiently proceed and the strength as a film can be maintained, it is possible to prevent the development latitude from becoming narrow in the case of alkali development.

That is, (A) the specific oxime compound, which is the polymerization initiator in the invention, has high light absorption efficiency, and therefore even when a colorant is contained in the photopolymerizable composition at high concentration, polymerization and curing can be caused with high sensitivity, whereby improvement effect on the sensitivity due to (A) the specific oxime compound is notably exerted, as compared with the case where other polymerization initiators are used.

(1)-(D) Pigment Dispersant

In a case in which the photopolymerizable composition (1) contains a pigment such as titanium black or an organic pigment as (C) a colorant, it is desirable to further add (D) a pigment dispersant to the photopolymerizable composition (1) from the viewpoint of improving the dispersibility of the pigment.

Examples of the pigment dispersant that can be used in the invention include a polymeric dispersant (for example, a polyamide amine and a salt thereof, a polycarboxylic acid and a salt thereof, a high molecular weight unsaturated acid ester, a modified polyurethane, a modified polyester, a modified poly(meth)acrylate, a (meth)acrylic copolymer, and naphthalenesulfonic acid-formalin condensate) and a polyoxyethylene alkylphosphate, a polyoxyethylene alkylamine, an alkanolamine, and pigment derivatives.

The polymeric dispersant can be further classified into a straight-chained polymer, a terminal modified polymer, a graft polymer, and a block polymer on the basis of the structure of the dispersant.

The polymeric dispersant adsorbs to the surface of a pigment, and functions so as to prevent re-aggregation. Accordingly, preferable examples of the structures include a terminal modified polymer, a graft polymer, and a block polymer, which have an anchor moiety to the pigment surface.

On the other hand, pigment derivatives have an effect of promoting the adsorption of the polymeric dispersant by modifying the pigment surface.

Specific examples of the dispersant that can be used in the invention include: "DISPERBYK-101 (polyamideamine phosphate), 107 (carboxylic ester), 110 (copolymer containing an acid group), 130 (polyamide), 161, 162, 163, 164, 165, 166, and 170 (high molecular copolymer)", "BYK-P104 and P105 (high molecular weight unsaturated polycarboxylic acid)" manufactured by BYK-Chemie GmbH; "EFKA 4047, 4050, 4010, and 4165 (polyurethanes)", and "EFKA4330, and 4340 (block copolymers), 4400, and 4402 (modified polyacrylate), 5010 (polyester amide), 5765 (high molecular weight polycarboxylic acid salt), 6220 (fatty acid polyester), 6745 (phthalocyanine derivative), 6750 (azo pigment derivative)" manufactured by EFKA Chemicals B.V.; "AJISPER PB821, and PB822" manufactured by Ajinomoto Fine Techno Co., Inc.; "FLOWLEN TG-710 (urethane oligomer)", "POLYFLOW No. 50E, No. 300 (acrylic copolymer)" manufactured by Kyoeisha Chemical Co., Ltd.; "DISPARLON KS-860, 873SN, 874, and #2150 (aliphatic polyvalent carboxylic acid), #7004 (polyether ester), DA-703-50, DA-705, and DA-725", manufactured by Kusumoto Chemicals Ltd.; "DEMOR RN, N (naphthalenesulfonic acid-formalin polycondensate), MS, C, and SN-B (aromatic sulfonic acid-formalin polycondensate)", "HOMOGENOL L-18 (polymeric polycarboxylic acid)", "EMULGEN 920, 930, 935, and 985 (polyoxyethylene nonylphenyl ether)", "ACETAMINE 86 (stearylamine acetate)" manufactured by Kao Corporation; "SOLSPERSE 5000 (phthalocyanine derivative), 22000 (azo pigment derivative), 13240 (polyester amine), 3000, 17000, and 27000 (polymer having a functional moiety at a terminal portion thereof), 24000, 28000, 32000, and 38500 (graft type polymer)", manufactured by The Lubrizol Corporation; and "NIKKOL T106 (polyoxyethylene sorbitan monooleate) and MYS-IEX (polyoxyethylene monostealate)" manufactured by Nikko Chemicals Co., Ltd. In addition, specific examples of the dispersant also include amphoteric surfactants such as HINOACTO T-8000E manufactured by Kawaken Fine Chemicals Co., Ltd.

These dispersants may be used alone, or may be used in combination of two or more kinds. In the invention, it is particularly preferable to use a pigment derivative and a polymeric dispersant in combination.

The content of (D) the dispersant in the polymerizable composition (1) is preferably from 1 part by mass to 80 parts by mass, more preferably from 5 parts by mass to 70 parts by mass, and still more preferably from 10 parts by mass to 60 parts by mass, relative to 100 parts by mass of a pigment as (C) the colorant.

Specifically, in the case where a polymeric dispersant is used, the use amount of the polymeric dispersant is preferably in the range of from 5 parts to 100 parts, and more preferably in the range of from 10 parts to 80 parts in terms of mass, relative to 100 parts by mass of the pigment.

Further, in the case where a polymeric dispersant is used, a pigment derivative is used together with the polymeric dispersant, the use amount of the pigment derivative is preferably in the range of from 1 part to 30 parts, more preferably in the range of from 3 parts to 20 parts, and still more preferably in the range of from 5 parts to 15 parts in terms of mass, relative to 100 parts by mass of the pigment.

In the case where the pigment as (C) a colorant is used in the photopolymerizable composition (1), and (D) a pigment dispersant is further used, the total sum of the contents of the colorant and the dispersant is preferably from 30% by mass to 90% by mass, more preferably from 40% by mass to 85% by mass, and still more preferably from 50% by mass to 80% by mass, relative to the total solid contents which forms the photopolymerizable composition.

If needed, the photopolymerizable composition (1) may further contain an arbitrary component, which will be explained in detail, unless the effect of the invention is impaired.

Hereafter, the arbitrary component, which may be contained in the photopolymerizable composition (1), is explained.

(1)—Sensitizer

A sensitizer may be contained in the photopolymerizable composition (1) in order to improve the radical generation efficiency of a radical initiator, and to make a photosensitive wavelength longer.

As the sensitizer, which can be used in the invention, a sensitizer that sensitizes the polymerization initiator by way of an electron transfer mechanism or energy transfer mechanism is preferred.

Examples of the sensitizer, which may be used in the photopolymerizable composition (1), include the compounds which are described below, and those have an absorption wavelength in a wavelength region of 300 nm to 450 nm.

Examples of the sensitizer include polynuclear aromatics (for example, phenanthrene, anthracene, pyrene, perylene, triphenylene, 9,10-dialkoxyanthracene), xanthenes (for example, fluorescein, eosine, erythrosine, Rhodamine B, rose bengal), thioxanthones (isopropylthioxanthone, diethylthioxanthone, chlorothioxanthone), cyanines (for example, thiacarbocyanine, oxacarbocyanine), merocyanines (for example, merocyanine, carbomerocyanine), phthalocyanines, thiazines (for example, thionine, methylene blue, toluidine blue), acridines (for example, acridine orange, chloroflavin, acriflavine), anthraquinones (for example, anthraquinone), squaryliums (for example, squarylium), acridine orange, coumarins (for example, 7-diethylamino-4-methylcoumarin), ketocoumarin, phenothiazines, phenazines, styryl benzenes, azo compounds, diphenyl methane, triphenyl methane, distyryl benzenes, carbazoles, porphyrin, Spiro compounds, quinacridone, indigo, styryl compounds, pyrylium compounds, pyrromethene compounds, pyrazolotriazole compounds, benzothiazole compounds, barbituric acid derivatives, thiobarbituric acid derivatives, aromatic ketone compounds such as acetophenone, benzophenone, thioxanthone, Michler's ketone, and heterocyclic compounds such as N-aryloxazilidinone or the like.

The content of the sensitizer in the photopolymerizable composition (1) is preferably from 0.1% by mass to 20% by mass, and more preferably from 0.5% by mass to 15% by mass in terms of solid content, from the viewpoint of the light absorption efficiency to the deep portion and the decomposition efficiency of an initiator.

The sensitizer may be used alone, or may be used in combination of two or more kinds.

(1)—Co-Sensitizer

It is preferable that a co-sensitizer be further contained in the photopolymerizable composition (1).

In the invention, the co-sensitizer has a function of further increasing the sensitivity of (A) the specific oxime compound or the above-described sensitizer to actinic radiation, or a function of suppressing the polymerization inhibition of (B) the polymerizable compound due to oxygen, or the like.

Examples of the co-sensitizing agent include amines such as the compounds described in M. R. Sander et al., Journal of Polymer Society, Vol. 10, p. 3173 (1972), JP-B No. 44-20189, JP-A Nos. 51-82102, 52-134692, 59-138205, 60-84305, 62-18537, and 64-33104, and Research Disclosure 33825.

Specific examples thereof include triethanolamine, ethyl p-dimethylaminobenzoate, p-formyldimethylaniline, and p-methylthiodimethylaniline.

Other examples of the co-sensitizing agent include thiols and sulfides such as the thiol compounds described in JP-A No. 53-702, JP-B No. 55-500806 and JP-A No. 05-142772 and the disulfide compounds described in JP-A No. 56-75643, and specific examples thereof include 2-mercaptobenzothiazole, 2-mercaptobenzoxazole, 2-mercaptobenzimidazole, 2-mercapto-4(3H)-quinazoline, and β-mercaptonaphthalene.

Other examples of the co-sensitizing agent also include amino acid compounds (such as N-phenyl glycine), the organometallic compounds described in JP-B No. 48-42965 (such as tributyl tin acetate), the hydrogen donors described in JP-B No. 55-34414, and the sulfur compounds (such as trithiane) described in JP-A No. 06-308727.

From the viewpoint of improvement in the curing rate due to the balance between the polymerization growing rate and the chain transfer, the content of the co-sensitizer is preferably in the range of from 0.1% by mass to 30% by mass, more preferably in the range of from 1% by mass to 25% by mass, and still more preferably in the range of from 0.5% by mass to 20% by mass, relative to the total mass of the solid content of the photopolymerizable composition (1).

Further, a thiol compound as a co-sensitizer is preferably contained in the photopolymerizable composition (1).

As a thiol compound which may be contained in the photopolymerizable composition (1), the compound represented by the following Formula (VI) or Formula (VII) is preferable.

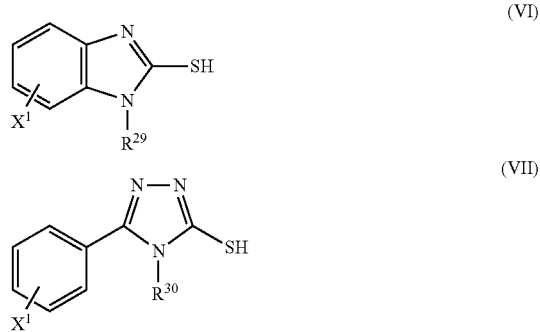

In Formula (VI), $R^{29}$ represents an aryl group, and $X^1$ represents a hydrogen atom, a halogen atom, an alkoxy group, an alkyl group, or an aryl group.

In Formula (VII), $R^{30}$ represents an alkyl group or an aryl group, and $X^1$ has the same definition as that of $X^1$ in Formula (VI).

In the case where the photopolymerizable composition (1) contains a thiol compound, the content of the thiol compound is preferably in the range of from 0.5% by mass to 30% by mass, more preferably in the range of from 1% by mass to 25% by mass, and still more preferably in the range of from 3% by mass to 20% by mass, relative to the total mass of the solid content of the photopolymerizable composition, from the viewpoint of improvement in the curing rate due to the balance between the polymerization growing rate and the chain transfer.

(1)—Binder Polymer

The photopolymerizable composition (1) may further contain a binder polymer, if needed, for the purposes of improving film forming property or the like. As the binder polymer, it is desirable to use a linear organic polymer. As such "linear organic polymer", known polymers can arbitrarily be used. Preferably, in order to enable water development or weak alkaline solution development, a linear organic polymer which is soluble or swellable in water or a weak alkaline solution is selected. The linear organic polymer is selected depending on the intended use of not only a film-forming agent, but also water developer, a weak alkaline solution developer or an organic solvent developer. For example, when a water-soluble organic polymer is used, water development becomes feasible. Example of such linear organic polymers include a radical polymer having a carboxylic acid group in a side chain thereof, for example, the polymers recited in JP-A No. 59-44615, JP-B No. 54-34327, JP-B No. 58-12577, JP-B No. 54-25957, JP-A No. 54-92723, JP-A No. 59-53836, and JP-A No. 59-71048, namely, resins that are formed by homopolymerizing or copolymerizing monomers having a carboxyl group; resins that are formed by homopolymerizing or copolymerizing monomers having an acid anhydride to form an acid anhydride unit and then by hydrolyzing, or half-esterifying of half-amidating the acid anhydride unit; and epoxy acrylates that are formed by modifying an epoxy resin with unsaturated monocarboxylic acid or an acid anhydride. Examples of monomers having a carboxyl group include acrylic acid, methacrylic acid, itaconic acid, crotonic acid, maleic acid, fumaric acid, and 4-carboxy styrene, and examples of monomers having an acid anhydride include maleic anhydride.

Similarly, there are acidic cellulose derivatives having a carboxylic acid group at a side chain thereof. In addition, a polymer formed by adding a cyclic acid anhydride to a polymer having a hydroxyl group, or the like is useful.

Similarly, there are cellulose derivatives having a carboxylic acid group at a side chain thereof may be used. In addition, a polymer formed by adding a cyclic acid anhydride to a polymer having a hydroxyl group, or the like is useful.

Among these various alkali soluble binders, polyhydroxystyrene resins, polysiloxane resins, acrylic resins, acrylamide resins and acryl/acrylamide copolymer resins are preferred from the viewpoint of the thermal resistance, and acrylic resins, acrylamide resins, acryl/acrylamide copolymer resins are preferred from the viewpoint of controlling developability.

As the acrylic resins, a copolymer composed of monomers selected from benzyl(meth)acrylates, (meth)acrylic acids, hydroxyethyl(meth)acrylates, (meth)acrylamides or the like, commercially available DIANAL NR series (manufactured by MITSUBISHI RAYON Co., Ltd.), VISCOAT R-264 and KS RESIST 106 (all manufactured by Osaka Organic Chemical Industry Ltd.), CYCLOMER P series, PRAXEL CF200 series (all manufactured by Daicel Chemical Industries, Ltd.), EBECRYL3800 (manufactured by Daicel UCB Co, Ltd.) or the like are preferred.

The weight average molecular weight of the binder polymer which can be used in the photopolymerizable composition (1) is preferably 5,000 or more, and more preferably in the range of from 10,000 to 300,000, and the number average molecular weight is preferably 1,000 or more, and more preferably in the range of from 2,000 to 250,000. The polydispersity (weight average molecular weight/number average molecular weight) is preferably 1 or more, and more preferably in the range of from 1.1 to 10.

These binder polymers may be any of a random polymer, a block polymer, a graft polymer and the like.

The content of the binder polymer is preferably from 1% by mass to 50% by mass, more preferably from 1% by mass to 30% by mass, and sill more preferably from 1% by mass to 20% by mass, with respect to the total solid content of the photopolymerizable composition (1).

(1)—Polymerization Inhibitor

In order to prevent unnecessary thermal polymerization of (B) the polymerizable compound during the manufacture or storage of the photopolymerizable composition (1), it is preferable to add a small amount of an inhibitor of thermal polymerization in the photopolymerizable composition (1).

The addition amount of the inhibitor of thermal polymerization is preferably from about 0.01% by mass to about 5% by mass with respect to the total solid content of the photopolymerizable composition (1).

(1)—Adhesion-Improving Agent

In order to enhance the adhesion of the formed cured film to a hard surface of a support or the like, an adhesion-improving agent may be added to the photopolymerizable composition (1). Examples of the adhesion-improving agent include a silane coupling agent, a titanium coupling agent, or the like.

Preferable examples of the silane coupling agent include γ-methacryloxypropyl trimethoxysilane, γ-methacryloxypropyl triethoxysilane, γ-acryloxypropyl trimethoxysilane, γ-acryloyloxypropyl triethoxysilane, γ-mercaptopropyl trimethoxysilane, γ-aminopropyl triethoxysilane, and phenyl trimethoxysilane, and γ-methacryloxypropyl trimethoxysilane is more preferable.

The addition amount of the adhesion-improving agent is preferably from 0.5% by mass to 30% by mass, and more preferably from 0.7% by mass to 20% by mass, with respect to the total solid content of the photopolymerizable composition (1).

(1)—Solvent

Various organic solvents may be used for the photopolymerizable composition (1).

Examples of the organic solvents used herein include acetone, methyl ethyl ketone, cyclohexane, ethyl acetate, ethylene dichloride, tetrahydrofuran, toluene, ethylene glycol monomethyl ether, ethylene glycol monoethyl ether, ethylene glycol dimethyl ether, propylene glycol monomethyl ether, propylene glycol monoethyl ether, acetylacetone, cyclohexanone, diacetone alcohol, ethylene glycol monomethyl ether acetate, ethylene glycol ethyl ether acetate, ethylene glycol monoisopropyl ether, ethylene glycol monobutyl ether acetate, 3-methoxypropanol, methoxymethoxy ethanol, diethylene glycol monomethyl ether, diethylene glycol monoethyl ether, diethylene glycol dimethyl ether, diethylene glycol diethyl ether, propylene glycol monomethylether acetate, propylene glycol monoethyl ether acetate, 3-methoxy propylacetate, N,N-dimethyl formamide, dimethyl sulfoxide, γ-butyrolactone, methyl lactate, and ethyl lactate.

These solvents may be used alone, or may be used in mixture.

The concentration of the solid content relative to the organic solvent in the photopolymerizable composition of the invention is preferably from 2% by mass to 60% by mass.

(1)—Surfactant

From the viewpoint of improving the coating properties, a variety of surfactants may be added to the photopolymerizable composition (1). Examples of usable surfactants include a variety of surfactants such as fluorosurfactants, nonionic surfactants, cationic surfactants, anionic surfactants and silicone surfactants.

In particular, since the liquid properties (in particular, fluidity) in the case where the composition is prepared as a coating liquid are improved by containing the fluorosurfactant, uniformity of the coating thickness or liquid-saving properties can be further improved.

More specifically, when a film is formed by using a coating liquid to which the photopolymerizable composition (1) containing the fluorosurfactant is applied, the surface tension between a surface to be coated and the coating liquid is lowered and wettability with respect to the surface to be coated is improved, whereby the coating properties with respect to the surface to be coated can be improved. As a result, even when a thin film having a thickness of several micrometers is formed with a small amount of liquid, a film having a uniform thickness with suppressed thickness unevenness can be more suitably formed, which is advantageous.

The content of fluorine in the fluorosurfactant is preferably from 3% by mass to 40% by mass, more preferably from 5% by mass to 30% by mass, and particularly preferably from 7% by mass to 25% by mass. A fluorosurfactant whose fluorine content is within this range is advantageous in terms of uniform thickness of the coated film and liquid-saving properties, and the solubility of the surfactant in the photopolymerizable composition (1) is also favorable.

Examples of the fluorosurfactant include MEGAFAC F171, F172, F173, F176, F177, F141, F142, F143, F144, R30, F437, F475, F479, F482, F554, F780 and F781 (manufactured by DIC Corporation); FLUORAD FC430, FC431 and FC171 (manufactured by Sumitomo 3M Co., Ltd.); and SURFLON S-382, SC-101, SC-103, SC-104, SC-105, SC1068, SC-381, SC-383, S393 and KH-40 (manufactured by Asahi Glass Co., Ltd.), SOLSPERSE 20000 (manufactured by Lubrizol Japan Limited).

Specific examples of the nonionic surfactant include glycerol, trimethylolpropane, trimethylolethane, and ethoxylate and propoxylate thereof (for example, glycerolpropoxylate, glycerinethoxylate or the like), polyoxyethylene lauryl ether, polyoxyethylene stearyl ether, polyoxyethylene oleyl ether, polyoxyethylene octylphenyl ether, polyoxyethylene nonylphenyl ether, polyethylene glycol dilaurate, polyethylene glycol distearate, and sorbitan fatty acid ester (PLURONIC L10, L31, L61, L62, 10R5, 17R2 and 25R2, and TETRONIC 304, 701, 704, 901, 904 and 150R1, manufactured by BASF Corporation).

Specific examples of the cationic surfactant include phthalocyanine derivatives (trade name: EFKA-745, manufactured by Morishita Chemical Industry Co., Ltd.), organosiloxane polymer KP341 (manufactured by Shin-Etsu Chemical Co., Ltd.), (meth)acrylic acid (co)polymer POLYFLOW No. 75, No. 90, No. 95 (manufactured by Kyoeisha Chemical Co., Ltd.), W001 (manufactured by Yusho Co., Ltd.).

Specific examples of the anionic surfactant include W004, W005, W017 (manufactured by Yusho Co., Ltd.).

Examples of the silicone surfactant include TORAY SILICONE DC3PA, TORAY SILICONE SH7PA, TORAY SILICONE DC11PA, TORAY SILICONE SH21PA, TORAY SILICONE SH28PA, TORAY SILICONE SH29PA, TORAY SILICONE SH30PA, and TORAY SILICONE SH8400 (manufactured by Dow Corning Toray Co., Ltd.); TSF-4440, TSF-4300, TSF-4445, TSF-4460, and TSF-4452 (manufactured by Momentive Performance Materials Inc.); KP341, KF6001 and KF6002 (manufactured by Shin-Etsu Chemical Co., Ltd.); and BYK307, BYK323 and BYK330 (manufactured by BYK-Chemie).

The surfactants may be used alone or in combination of two or more kinds thereof.

The amount of the surfactant added is preferably from 0.001% by mass to 2.0% by mass and more preferably from 0.005% by mass to 1.0% by mass, with respect to the total mass of the photopolymerizable composition (1).

(1)—Other Additives

Further, in order to improve the physical properties of the cured film, known additives such as an inorganic filler, a plasticizer, a sensitizing agent or the like may be added to the photopolymerizable composition (1).

Examples of the plasticizer include dioctylphthalate, didodecylphthalate, triethylene glycol dicaprylate, dimethylglycol phthalate, tricresyl phosphate, dioctyladipate, dibutyl sebacate, and triacetyl glycerin, and when a binder is used, the plasticizer can be added in an amount of 10% by mass or less relative to the total mass of a polymerizable compound and a binder polymer.

Photopolymerizable Composition (2)—Photopolymerizable Composition for Photosensitive Planographic Printing Plate Precursor Since the photopolymerizable composition of the invention can form a tough coat film in an exposed area as a result of curing with high sensitivity by pattern exposure, the photopolymerizable composition is useful for forming a photosensitive layer of a planographic printing plate precursor.

Hereinafter, preferable embodiments in a case in which the photopolymerizable composition of the invention is applied to the photosensitive layer of the planographic printing plate precursor are described.

(2)-(A) Specific Oxime Compound

The specific oxime compound contained in the photopolymerizable composition (2) can function as a polymerization initiator in the composition. (A) The specific oxime compound in this aspect is the same as (A) the specific oxime compound stated above.

The content of (A) the specific oxime compound in the photopolymerizable composition (2) is preferably from 0.5% by mass to 40% by mass, more preferably from 1% by mass to 35% by mass, and still more preferably from 1.5% by mass to 30% by mass, with respect to the total solid content of the composition.

The specific oxime compound may be used alone, or may be used in combination of two or more kinds thereof.

Other Polymerization Initiators

In the photopolymerizable composition (2), known polymerization initiators other than the specific oxime compound may be used to the extent that the effect of the invention is not impaired.

Examples of other polymerization initiators include (a) aromatic ketones, (b) an aromatic onium salt compound, (c) an organic peroxide, (d) a thio compound, (e) a hexaaryl biimidazole compound, (f) a ketoxime ester compound, (g) a borate compound, (h) an azinium compound, (i) a metallocene compound, (j) an active ester compound, and (k) a compound having a carbon-halogen bond. More specifically, examples of the polymerization initiators include polymerization initiators as recited in paragraphs [0081] to of JP-A No. 2006-78749.

(2)-(B) Polymerizable Compound

Preferable examples of (B) the polymerizable compound contained in the photopolymerizable composition (2) include the same addition-polymerizable compounds as those described in the photopolymerizable composition (1).

Details of methods for using the addition-polymerizable compound such as the structure, the single use or combined use, or the addition amount of these addition-polymerizable compounds can arbitrarily be determined in accordance with the performance design of the target photosensitive material. For example, the addition-polymerizable compound can be selected from the following points of view.

In view of sensitization speed, the structure having a higher content of unsaturated groups per one molecule is desirable, and in many cases, a bifunctional or higher functional structure is desirable. Further, in order to strengthen an image area, namely a cured film, a trifunctional or higher functional compound is preferable, and furthermore, a method of controlling both the photosensitivity and the strength by using polymerizable compounds having different number of functional groups or different polymerizable groups (for example, an acrylic ester, a methacrylic ester, a styrene compound, and a vinyl ether compound) in combination, is also effective. Compounds having a higher molecular weight or compounds having higher hydrophobicity provide excellent photosensitivity and film strength, whereas in some cases, these compounds may not be desirable in view of developing speed and precipitation in a developer.

Further, regarding the compatibility with other components (for example, a binder polymer, an initiator, a colorant, and the like) in the photosensitive layer, and the dispersibility, the selection and the method for use of the addition-polymerization compound are an important factor; and for example, the compatibility may be improved by the use of a low purity compound, or two or more kinds of addition-polymerization compounds. In some cases, a specific structure can be selected for the purpose of enhancing adhesion to a support, an overcoat layer, or the like. In view of sensitivity, it is advantageous to make the compounding ratio of the addition-polymerizable compound in the photopolymerizable composition layer higher, but, in the case where the compounding ratio is too high, an unfavorable phase separation may arise, or problems in the manufacturing process resulting from the tackiness of the photopolymerizable composition layer (for example, failure in manufacturing process resulting from transfer or tackiness of component (s) in the photopolymerizable composition), or problems in precipitation from a developer, may arise.

From these points of view, the content of the addition-polymerizable compound is preferably from 5% by mass to 80% by mass, and more preferably from 25% by mass to 75% by mass, relative to the total solid content of the photopolymerizable composition (2).

Further, the addition-polymerizable compounds may be used alone, or may be used in combination of two or more kinds. In addition, as to the method of use of the addition-polymerizable compound, suitable structure, compounding ratio and addition amount can be appropriately selected from the viewpoint of the degree of polymerization inhibition due to oxygen, resolution, fogging property, change in refractive index, surface tackiness and the like. In some cases, the addition-polymerizable compound may be applied to a layer structure such as an undercoat, an overcoat, or by a coating method.

(2)—Binder Polymer

The polymerizable composition (2) preferably contains a binder polymer. The binder polymer is contained from the viewpoint of improving film property, and various binder polymers can be used as long as the binder polymer functions to improve the film property.

As the binder polymer, it is preferable to use a linear organic high molecular weight polymer. Such a "linear organic high molecular polymer" is not specifically limited to, and any linear organic high molecular weight polymer may be used. Preferably, a linear organic high molecular weight polymer is selected from those which enables water development or weak-alkaline-water development, or which is water swellable or weak-alkaline-water swellable.

The linear organic high molecular weight polymer is used not only for a film-forming agent of the photopolymerizable composition, but is selected and used in accordance with the formulation of water developer, weak-alkaline-water developer or organic-solvent developer. For example, when a water soluble organic high molecular weight polymer is used, water development is feasible. Examples of such a linear organic high molecular weight polymer include addition polymers having a carboxylic group at the side chain as recited in JP-A No. 59-44615, JP-B No. 54-34327, JP-B No. 58-12577, JP-B No. 54-25957, JP-A No. 54-92723, JP-A No. 59-53836, and JP-A No. 59-71048, namely, a methacrylic acid copolymer, an acrylic acid copolymer, an itaconic acid copolymer, a crotonic acid copolymer, a maleic acid copolymer, and a partially esterified maleic acid copolymer. Similarly, examples also include acidic cellulose derivatives having a carboxylic acid group at the side chain. In addition, a polymer, in which a cyclic anhydride is added to an addition polymer having a hydroxyl group, is useful.

Among these, copolymers of [benzyl(meth)acrylate/(meth)acrylic acid/optionally other addition-polymerizable vinyl monomer] and copolymers of [allyl(meth)acrylate/(meth)acrylic acid/optionally other addition-polymerizable vinyl monomer] are particularly suitable because they provide excellent balance between the film strength, the sensitivity and the developability.

The binder polymer may be mixed in the photopolymerizable composition (2) in an arbitrary quantity. From the viewpoint of the image strength and the like, the content of the binder polymer is preferably in the range of from 30% by mass to 85% by mass relative to the total solid content that forms a photosensitive layer. Further, it is preferable that the addition-polymerizable compound and the binder polymer be in the range of from 1/9 to 7/3 in terms of mass ratio.

In a preferable exemplary embodiment, the binder polymer which is substantially insoluble in water but is soluble in alkali is used. In this way, an organic solvent, which is environmentally unfavorable as a developing solution, is not used, or can be limited to an extremely small amount. In such a usage, the acid number (acid content per gram of polymer is expressed in terms of chemical equivalent number) and the molecular weight of the binder polymer are suitably selected from the viewpoint of the image strength and the developability. The acid number is preferably in the range of from 0.4 meq/g to 3.0 meq/g, and the molecular weight is preferably in the range of from 3,000 to 500,000. The acid number is more preferably in the range of from 0.6 meq/g to 2.0 meq/g, and the molecular weight is more preferably in the range of from 10,000 to 300,000.

(2)—Sensitizer

The photopolymerizable composition (2) desirably contains a sensitizer together with a polymerization initiator such as (A) the specific oxime compound. Examples of the sensitizer that can be used in the invention include a spectral sensitizing dye and a dye or pigment which absorbs light from a light source to interact with a polymerization initiator.

Examples of preferred spectral sensitizing dyes or pigments include polycyclic aromatic compounds (such as pyrene, perylene and triphenylene), xanthenes (such as fluorescein, eosin, erythrosine, rhodamine B, and rose bengal), cyanines (such as thiacarbocyanine and oxacarbocyanine), merocyanines (such as merocyanine and carbomerocyanine), thiazines (such as thionine, methylene blue and toluidine blue), acridines (such as acridine orange, chloroflavin, and acriflavin), phthalocyanines (such as phthalocyanine and metal phthalocyanine), porphyrins (such as tetraphenylporphyrin and center metal-substituted porphyrin), chlorophylls (such as chlorophyll, chlorophyllin and center metal-substituted chlorophyll), metal complexes, anthraquinones (such as anthraquinone), and squaryliums (such as squarylium).

More preferable examples of spectral sensitizing dye or dye stuff include those recited in paragraphs [0144] to [0202] of JP-A No. 2006-78749 or the like.

Further, examples of sensitizers which may be used for the photopolymerizable composition (2) also include those described above regarding the photopolymerizable composition (1).

The sensitizer may be used alone, or may be used in combination of two or more kinds thereof. The molar ratio of the total polymerization initiators and the sensitizing dye in the photopolymerizable composition (2) is from 100:0 to 1:99, more preferably from 90:10 to 10:90, and most preferably from 80:20 to 20:80.

(2)—Co-Sensitizer

Known compounds, which achieve further improvement in sensitivity, suppress the polymerization inhibition due to oxygen, or the like, may be added as co-sensitizers to the photopolymerizable composition (2).

Examples of the co-sensitizers include the co-sensitizers described above regarding the photopolymerizable composition (1). In addition to these, examples of co-sensitizers include phosphorous compounds (diethylphosphite and the like) as recited in JP-A No. 6-250387.

In the case where a co-sensitizer is used, the co-sensitizer is suitably used in an amount of from 0.01 part by mass to 50 parts by mass relative to 1 part by mass of the total amount of the polymerization initiator contained in the photopolymerizable composition (2).

(2)—Polymerization Inhibitor

In order to prevent compounds having a polymerizable ethylenic unsaturated double bond from unnecessary thermal polymerization during the manufacture or the storage of the composition, it is desirable to add a small amount of a thermal polymerization inhibitor to a photopolymerizable composition (2).

The addition amount of the thermal polymerization inhibitor is preferably from about 0.01% by mass to about 5% by mass with respect to the mass of the entire composition. If needed, in order to prevent the polymerization inhibition due to oxygen, a higher fatty acid derivative, such as behenic acid or behenic acid amide, or the like may be added, so that the higher fatty acid derivative or the like is localized on the surface of the coated film in the process of drying after coating. The addition amount of the higher fatty acid derivative is preferably from about 0.5% by mass to about 10% by mass with respect to the entire composition.

(2)-(C) Colorant

A dye or a pigment may be added to the photopolymerizable composition (2) for the purpose of coloring a photosensitive layer. In this way, plate examination property of a printing plate, such as visibility after plate-making or the suitability for an image density measuring apparatus, may be improved. Since most dyes cause reduction in sensitivity of a photopolymerization-type photosensitive layer, the use of a pigment is particularly desirable as a colorant. Specific examples of the colorant include pigments such as a phthalocyanine pigment, an azo pigment, carbon black, or titanium oxide, and dyes such as Ethyl Violet, Crystal Violet, an azo dye, an anthraquinone dye, or a cyanine dye. The addition amount of the dye or the pigment is preferably from about 0.5% by mass to about 5% by mass with respect to the entire composition.

(2)—Other Additives

Further, in order to improve the physical properties of the cured film, inorganic fillers or other known additives such as a plasticizer, a sensitizer that can increase inking property on the surface of a photosensitive layer may be added.

Examples of the plasticizer include dioctylphthalate, didodecylphthalate, triethylene glycol dicaprylate, dimethylglycol phthalate, tricresyl phosphate, dioctyladipate, dibutyl sebacate, and triacetyl glycerin. In the case where a binder is used, the plasticizer can be added in an amount of 10% by mass or less relative to the total mass of a compound having an ethylenic unsaturated double bond and the binder.

Further, a UV initiator, a thermal crosslinking agent, or the like may be added for enhancing the effect of heating and exposure after development for the purpose of improving film strength (printing durability).

Such a photopolymerizable composition (2) is applied on a support to form a photosensitive layer, thereby obtaining a planographic printing plate precursor of the invention. The planographic printing plate precursor of the invention will be described later.

Color filter and production method thereof.

Next, a color filter of the invention and the production method of the color filter are explained.

The color filter of the invention is characterized by including: a process of applying a photopolymerizable composition (the above-described photopolymerizable composition (1)) for color filter of the invention on a support to form a photopolymerizable composition layer (hereinafter, this layer may be simply referred to as a "photopolymerizable composition layer forming process", as occasion demands); a process of subjecting the polymerizable composition layer to pattern exposure (hereinafter, this process may be simply referred to as an "exposure process", as occasion demands); and a process of forming a colored pattern by developing the photopolymerizable composition layer after the exposure (hereinafter, this process may be simply referred to as a "developing process", as occasion demands).

Hereinafter, the color filter of the invention is described in detail by way of the production method thereof.

Specifically, the photopolymerizable composition (1) of the invention is coated directly on a support (substrate) or via another layer to form a polymerizable composition layer, and then the photopolymerizable composition layer is exposed to light through a predetermined mask pattern to cure only the exposed areas of the coated film, and then the exposed layer is developed with a developer to form a patterned film including respective color pixels (three colors or four colors), whereby a color filter of the invention can be produced.

Hereinafter, each process in the production method of the color filter of the invention is explained.

Photopolymerizable Composition Layer Forming Process

In the photopolymerizable composition layer forming process, the photopolymerizable composition of the invention is coated on a support to form a layer composed of the photopolymerizable composition.

Examples of the support which can be used in this process include alkali-free glass, soda glass, PYREX (registered trademark) glass, quartz glass and any of the glass to which a transparent electroconductive film is adhered, all of which are used for a liquid crystal display device or the like, and a photoelectric conversion element substrate used for an solid-state image sensing device such as a silicon board or the like or a complementary metal oxide semiconductor (CMOS). In some cases, black stripes are formed for separating pixels from one another on these substrates.

If needed, an undercoat layer may be formed on the supports, for improving adhesion to an upper layer above the support, for preventing the diffusion of substances, or for flattening the surface of the substrate.

As the coating method of the photopolymerizable composition for color filter of the invention on a support, various coating methods such as a slit coating, an inkjet method, a spin coating, a cast coating, a roll coating, or a screen printing method are applicable.

The thickness of the coated film of the photopolymerizable composition for color filter is preferably from 0.1 µm to 10 µm, more preferably from 0.2 µm to 5 µm, and still more preferably from 0.2 µm to 3 µm.

Further, when a color filter for solid-state image sensing device is produced, the thickness of the coated film of the photopolymerizable composition for color filter is preferably from 0.35 µm to 1.5 µm, and more preferably from 0.40 µm to 1.0 µm, from the viewpoint of resolution and developability.

The photopolymerizable composition (1) coated on a support is usually dried under the conditions of about 70° C. to 110° C. for about 2 minutes to about 4 minutes, whereby a photopolymerizable composition layer is formed.

Exposure Process

In the exposure process, the photopolymerizable composition layer formed in the photopolymerizable composition layer forming process is subjected to a pattern exposure. The pattern exposure is generally performed through a mask so that only the exposed area of the coated film is cured, but, in some cases, the pattern exposure may be performed by means of scanning exposure.

The exposure is preferably performed by irradiation with radiation rays, and as the radiation rays used in the exposure, in particular, ultraviolet rays such as g-line, h-line, i-line or the like are preferably used, and a high-pressure mercury vapor lamp is more preferably used. The irradiation intensity is preferably from 5 mJ/cm$^2$ to 1,500 mJ/cm$^2$, more preferably from 10 mJ/cm$^2$ to 1,000 mJ/cm$^2$, and most preferably from 10 mJ/cm$^2$ to 800 mJ/cm$^2$.

Development Process

Subsequent to the exposure process, an alkali development (development process) is performed, whereby an unexposed portion of the polymerizable composition layer in the exposure process is dissolved with an aqueous alkaline solution. As a result, only the photo-cured portion (colored pattern portion) remains.

As the developer, an organic alkaline developer which does not damage the underlaid circuit or the like is desirable. Usually, the developing temperature is from 20° C. to 30° C., and developing time is from 20 seconds to 90 seconds.

As the alkali used for the developer, for example, an alkaline aqueous solution formed in a manner such that an organic alkaline compound such as aqueous ammonia, ethylamine, diethylamine, dimethyl ethanolamine, tetramethyl ammonium hydroxide, tetraethyl ammonium hydroxide, choline, pyrrole, piperidine, or 1,8-diazabicyclo[5,4,0]-7-undecene is diluted with pure water to a concentration of from 0.001% by mass to 10% by mass, and preferably from 0.01% by mass to 1% by mass, is used.

An inorganic developing solution is also usable, and examples thereof include sodium hydroxide, potassium hydroxide, sodium carbonate, sodium hydrogen carbonate, sodium silicate and sodium metasilicate.

In a case in which such a developing solution composed of alkaline solution is used, generally washing (rinse) with pure water is performed after development.

When a developer including such an alkaline aqueous solution is used, generally, washing (rinse) with pure water is preformed after development.

In addition, the production method of the color filter of the invention may include a curing process that cures the formed colored pattern by heating and/or exposure, if necessary, after performing the photopolymerizable composition layer forming process, the exposure process, and the development process as described above.

The photopolymerizable composition layer forming process, the exposure process, and the developing process (and further a curing process, if necessary) as described above, are repeatedly performed in accordance with the number of desired hues, whereby a color filter having the desired hues can be produced.

Solid-State Image Sensing Device

The solid-state image sensing device of the invention includes at least the color filter of the invention.

Since the photopolymerizable composition for color filter of the invention is used in the color filter of the invention, the color filter exhibits favorable exposure sensitivity, the formed colored pattern exhibits high adhesion to a support substrate, and the cured composition is excellent in development resistance. Accordingly, a high-resolution pattern which provides a desired cross-sectional profile can be formed. Therefore, the color filter is suitably used for a liquid crystal display device and a solid-state image sensing device such as CCD, or the like, and in particular, is suitable for CCD and CMOS each of which has a high resolution exceeding 1,000,000 pixels. That is, it is preferable that the color filter of the invention be used for the solid-state image sensing device.

The color filter of the invention, for example, can be used as a color filter arranged between a light receiving portion of each pixel which constitutes a CCD and a microlens for light condensing.

Liquid Crystal Display

Since the color filter of the present invention has a colored pixel which has a favorable patternability and an excellent adhesion to a support, and retains a pattern shape even during post-heating after development and is avoided from coloring by heating, the color filter is suitable for a liquid crystal display and an organic EL display, and particularly preferable as a color filter for a liquid crystal display.

A liquid crystal display provided with such a color filter can display a high quality image.

The definition of displays or the explanation of each of the display are described, for example, in "Electric Display Device", Akio Sasaki, Kogyo Chosakai Publishing Co., Ltd., 1990, "Display Device", Sumiaki Ibuki, Sangyo Tosho K.K., 1989 or the like. The liquid crystal display is described, for example, in "Next Generation Liquid Crystal Display Technology", Tatsuo Uchida ed., Kogyo Chosakai Publishing Co., Ltd., 1994. Liquid crystal displays to which the present invention is applicable are not particularly limited. For example, the present invention is applicable to various types of liquid crystal displays which are described in the above-mentioned "Next generation liquid crystal display technology".

The color filter of the present invention is effective for, among others, a color TFT liquid crystal display. The color TFT liquid crystal display is described in "Color TFT liquid crystal display (KYORITSU SHUPPAN CO., LTD, 1996)". Further, the present invention is also applicable to a liquid crystal display having a wide viewing angle, for example, using an in-plane switching driving method such as IPS, or a pixel division method such as MVA, and further applicable to STN, TN, VA, OCS, FFS, R-OCB 1 or the like.

The color filter of the present invention can also be provided to a COA (Color-filter On Array) type liquid crystal display having high brightness and a high definition. Required performances with respect to an interlayer dielectric film, that is, a low-dielectric constant and a resistance to a remover, as well as the above-mentioned normal required performances with respect to a color filter layer are necessary for a COA type liquid crystal display. Due to selection of a pixel hue or a film thickness in addition to an ultra violet laser exposure technique, since a permeability of the ultraviolet laser used as an exposure light is high and the color filter of the present invention has both a favorable patternability and an excellent adhesion to a support, particularly a resistance to a remover of a colored layer provided directly or indirectly on a TFT substrate is improved, and therefore, the color filter is useful for a COA type liquid crystal display. In order to fulfill the required performance of a low dielectric constant, a resin film may be provided on the color filter layer.

Further, in order that between an ITO electrode disposed on the colored layer can make a continuity with a terminal of a drive substrate below the colored layer, it is necessary to form a conducting channel such as a rectangular through hole or a U-shaped cavity, each of which has a side length of about 1 to 15 μm, on a colored layer to be formed in a COA system. The size of the conducting channel (that is, side length) is particularly preferably not more than 5 μm, and by using the present invention, the conducting channel having the size of not more than 5 μm can be formed.

These image display types are described, for example, in "EL, PDP, LCD Display—Latest Trend of Technology and Market—(Toray Research Center, Investigation Research Division, 2001)" on page 43 or the like.

The liquid crystal display of the present invention is composed of a variety of members such as an electrode substrate, a polarizing film, a phase difference film, a backlight, a spacer and a viewing angle compensation film, in addition to the color filter of the present invention. The color filter of the present invention is applicable to a liquid crystal display composed of these known members.

These members are described, for example, in "'94, Market on Liquid Crystal Display Peripheral Materials and Chemicals", Kentaro Shima, CMC Publishing Co., Ltd., 1994 and "2003, Present Condition and Future Perspective on Liquid Crystal Related Market (the second volume)", Ryokichi Omote, FUJI CHIMERA RESEARCH INSTITUTE, Inc., 2003.

The backlight is described in SID meeting Digest 1380 (2005) (A. Konno et. al), Monthly Display, December, 2005, pp. 18-24, (Yasuhiro Shima), and pp. 25-30 (Takaaki Yagi).

In the case where the color filter of the present invention is used for a liquid crystal display, a high contrast can be attained when the display is combined with a conventionally known three-wavelength type cold-cathode tube. Further, by using red, green and blue LED light sources (RGB-LED) as backlight, a liquid crystal display having a high brightness, a high color purity and a favorable color reproducibility can be provided.

Planographic Printing Plate Precursor

Next, a planographic printing plate precursor of the invention is explained.

The planographic printing plate precursor of the invention includes a support and a photosensitive layer including the above-described photopolymerizable composition (2) provided on the support.

For making a printing plate using the planographic printing plate precursor of the invention, the photopolymerizable composition (2) in the invention is directly applied to a support for a planographic printing plate or via another layer therebetween, to obtain a photopolymerizable composition layer, whereby a planographic printing plate precursor is obtained. Then, the photosensitive layer of the planographic printing plate precursor is subjected to pattern exposure to cure only the exposed area thereof, and the unexposed area is developed with a developer. As a result, the remaining photosensitive layer forms an ink receiving layer for printing, and the area, in which the photosensitive layer has been removed whereby a hydrophilic support is exposed, serves as an area for receiving dampening water, thereby obtaining a planographic printing plate.

The planographic printing plate precursor of the invention may have other layers such as a protective layer, an intermediate layer or the like, if needed. Since the photosensitive layer contains the photopolymerizable composition of the invention, the planographic printing plate precursor of the invention has high sensitivity, excellent temporal stability and excellent printing durability. Hereinafter, each element of the planographic printing plate precursor of the invention is explained.

Photosensitive Layer

The photosensitive layer is a layer containing the photopolymerizable composition of the invention. Specifically, the photopolymerizable composition (2), which is one of the suitable aspects of the photopolymerizable compositions of the invention, is used as a composition for forming a photosensitive layer (hereinafter, this may be referred to as a "composition for photosensitive layer", as occasion demands), and a coating liquid including the composition is coated on a support and dried, whereby the photosensitive layer can be formed.

When the composition for the photosensitive layer is coated on a support, each component to be included in the composition is dissolved in various solvents and used. Examples of the solvents herein used include acetone, methylethyl ketone, cyclohexane, ethyl acetate, ethylene dichloride, tetrahydrofurane, toluene, ethyleneglycol monomethylether, ethyleneglycol monoethylether, ethyleneglycol dimethylether, propyleneglycol monomethylether, propyleneglycol monoethylether, acetyl acetone, cyclohexanone, diacetone alcohol, ethyleneglycol monomethylether acetate, ethyleneglycol ethylether acetate, ethyleneglycol monoisopropylether, ethyleneglycol monobutylether acetate, 3-methoxypropanol, methoxymethoxy ethanol, diethyleneglycol monomethylether, diethyleneglycol monoethylether, diethyleneglycol dimethylether, diethyleneglycol diethylether, propyleneglycol monomethylether acetate, 3-methoxypropylacetate, N,N-dimethylformamide, dimethylsulfoxide, γ-butyrolactone, methyl lactate, and ethyl lactate. These solvents may be used singly or in combination thereof.

The appropriate concentration of solid content in the coating liquid is from 2 to 50% by mass.

The coating amount of the photosensitive layer on a support may have an affect mainly on both sensitivity and developability of the photosensitive layer and both toughness and printing durability of the exposed film. Accordingly, it is desirable to select the coating amount depending on the intended use. When the coating amount is too small, the printing durability becomes insufficient. On the other hand, when the coating amount is too large, the sensitivity reduces, the exposure becomes time consuming, and it takes a longer time to perform a development process. Accordingly, both cases are not preferable.

In the photosensitive layer for the planographic printing plate precursors for scanning exposure, which is a main purpose of the invention, the coating amount of the photosensitive layer in terms of mass unit after drying is preferably in the range of from 0.1 g/m$^2$ to 10 g/m$^2$, and more preferably in the range of from 0.5 g/m$^2$ to 5 g/m$^2$.

Support

As the support used for a planographic printing plate precursor of the present invention, known supports may be used. Among them, an aluminium plate subjected to a roughening process and an anodic oxidation process by known methods is preferred.

A process of enlarging or a process of sealing micropores of the anodic oxide film described in JP-A No. 2001-253181 or JP-A No. 2001-322365, or a process of surface hydrophilization by alkali metal silicates as described in U.S. Pat. No. 2,714,066, U.S. Pat. No. 3,181,461, U.S. Pat. No. 3,280,734 and U.S. Pat. No. 3,902,734, polyvinylphosphonic acids as described in U.S. Pat. No. 3,276,868, U.S. Pat. No. 4,153,461 and U.S. Pat. No. 4,689,272, or the like can be appropriately selected and applied to the above-mentioned aluminium plate as needed.

The center line average roughness of the support is preferably from 0.10 to 1.2 μm.

Protective Layer

Preferably the planographic printing plate precursor of the invention further has a protective layer on the photosensitive layer.

Protective layer-related inventions have been made in the past. For example, details of such inventions are described in U.S. Pat. No. 3,458,311 and JP-A No. 55-49729.

As a material that can be used for the protective layer, for example, it is desirable that a water-soluble polymeric compound having relatively high crystallinity be used. Specifically, water-soluble polymers such as polyvinyl alcohol, polyvinyl pyrrolidone, acidic celluloses, gelatin, gum Arabic, or polyacrylic acid are known. Among them, use of a polyvinyl alcohol as a principal component makes it possible to achieve the most favorable results in terms of basic characteristics such as oxygen blocking property or removability in development.

As long as the polyvinyl alcohol used for the protective layer has an unsubstituted vinyl alcohol unit having the necessary oxygen insulation property and water solubility, a part of the polyvinyl alcohol may be substituted with ester, ether, or acetal. Similarly, the polyvinyl alcohol may include partially another copolymerizable component. Specific examples of the polyvinyl alcohol include a polyvinyl alcohol having the rate of hydrolysis in the range of from 71% by mole to 100% by mole and having a mass average molecular weight in the range of from 300 to 2,400.

The components (choice of PVAs, use of additives and the like), the coating amount and the like of the protective layer may be selected in consideration of oxygen insulation property, removability by development, fogging, adhesion property, or scratch resistance. In general, the higher the rate of hydrolysis of the PVA to be used (the higher the content of unsubstituted vinyl alcohol units in the protective layer) or the larger the thickness of the film, the more the oxygen insulation property increases, which is advantageous in terms of sensitivity. However, when the oxygen insulation property is increased excessively, problems may arise such that unnecessary polymerization reaction occurs during manufacture or storage and unnecessary fogging or thickening of image lines occurs in the time of image-wise exposure. The adhesion to the image portion and the scratch resistance are also very important for the handleability of the printing plate. Methods for coating the protective layer are described in detail in, for example, U.S. Pat. No. 3,458,311 and JP-A No. 55-49729.

Further, other functions may be also imparted to the protective layer. For example, when a colorant (water-soluble dye or the like), which exhibits good transmittance of light having a wavelength of 350 nm to 450 nm used for exposure, and which efficiently absorbs light of 500 nm or longer, is added, safelight property can be further improved without reducing sensitivity.

Other Layers

In addition, it is possible to arrange an additional layer for improving the adhesion between the photosensitive layer and the support, or for improving the removability of an unexposed photosensitive layer in development.

For example, the adhesion between the support and the photosensitive layer may be improved by adding a compound, which has relatively strong interaction with a substrate, such as a compound having a diazonium structure, a phosphonic compound or the like to the photosensitive layer, or by disposing an undercoat layer containing such compound between the substrate and the photosensitive layer, whereby the printing durability may be enhanced.

On the other hand, the developability of a non-image area can be improved by adding a hydrophilic polymer such as a polyacrylic acid or a polysulfonic acid to the photosensitive layer, or by disposing an undercoat layer containing such compound, and scumming resistance can be improved.

Plate-Making

Usually, after the planographic printing plate precursor is subjected to an image-exposure to cure the photosensitive layer in the exposed area, an unexposed area of the photosensitive layer is removed with a developer to form an image, and thus, plate-making is performed. In this way, a planographic printing plate can be obtained.

As the exposing method applicable to the planographic printing plate precursor of the invention, known methods may be used without limitation. In the invention, since (A) the specific oxime compound is used as a photopolymerization initiator, the wavelengths of an exposure light source are desirably from 350 nm to 450 nm, and specially, an InGaN semiconductor laser is suitable.

The exposure mechanism may be any mechanism such as an internal drum system, an external drum system, a flat-bed system, or the like. Further, use of a component of the photosensitive layer having high water-solubility makes it possible to be soluble in a neutral water or a weak alkaline water; and a planographic printing plate having such a constitution can be applied to a so-called on-machine development method without using a wet development such that the planographic printing plate is exposed and developed on a printing machine after the printing plate is mounted on the machine.

As available laser light sources of 350 to 450 nm, the following lasers can be used.

Examples of gas lasers include Ar ion lasers (364 nm, 351 nm, from 10 mW to 1 W), Kr ion lasers (356 nm, 351 nm, from 10 mW to 1 W) and He—Cd lasers (441 nm, 325 nm, from 1 to 100 mW). Examples of solid-state lasers include a combination of Nd:YAG (YVO$_4$) and SHG crystal (twice) (355 nm, 5 mW to 1 W) and a combination of Cr:LiSAF and SHG crystal (430 nm, 10 mW). Examples of semiconductor lasers include KNbO$_3$ ring resonators (430 nm, 30 mW), a combination of a waveguide type wavelength converting device and an AlGaAs or InGaAs semiconductor (from 380 to 450 nm, 5 mW to 100 mW), a combination of a waveguide type wavelength converting device and an AlGaInP or AlGaAs semiconductor (300 to 350 nm, 5 to 100 mW), and AlGaInN lasers (from 350 to 450 nm, from 5 mW to 30 mW). Examples of other lasers include pulsed lasers such as N$_2$ lasers (337 nm, from 0.1 mJ to 10 mJ pulse) and XeF lasers (351 nm, from 10 mJ to 250 mJ pulse).

In particular, an AlGaInN semiconductor laser (commercially available InGaN semiconductor laser of from 400 nm to 410 nm, 5 mW to 30 mW) is suitable in view of wavelength characteristics and cost.

Regarding a planographic printing plate exposure machine with a scanning exposure system, an exposure mechanism such as an internal drum system, an external drum system, or a flat-bed system may be used, and the above-described light sources other than pulsed lasers can be used.

Furthermore, other exposure light sources such as mercury vapor lamps including ultra-high pressure mercury vapor lamps, high pressure mercury vapor lamps, medium pressure mercury vapor lamps and low pressure mercury vapor lamps, chemical lamps, carbon arc lamps, xenon lamps, metal halide lamps, visible laser lamps, ultraviolet laser lamps, fluorescent lamps, tungsten lamps, or sunlight may also be used.

Examples of developer suitable for the planographic printing plate precursor of the invention include a developer as recited in JP-B. No. 57-7427. As the developer, aqueous solutions including an inorganic alkali agent such as sodium silicate, potassium silicate, sodium hydroxide, potassium hydroxide, lithium hydroxide, sodium tertiary phosphate, sodium secondary phosphate, ammonium tertiary phosphate, ammonium secondary phosphate, sodium metasilicate, sodium bicarbonate or aqueous ammonia, or an organic alkali agent such as monoethanolamine or diethanolamine are suitable. Such an alkali agent is added so as to be a concentration of from 0.1% by mass to 10% by mass, and preferably from 0.5% by mass to 5% by mass of the alkaline solution.

Further, such an alkaline aqueous solution may include a small amount of a surfactant or an organic solvent such as benzyl alcohol, 2-phenoxyethanol or 2-butoxyethanol, if needed. Examples of these additives include those recited in U.S. Pat. No. 3,375,171 and U.S. Pat. No. 3,615,480.

Furthermore, the developers as recited in JP-A. No. 50-26601, JP-A No. 58-54341, JP-13 No. 56-39464, and JP-B No. 56-42860 are also preferable.

In addition, in the plate-making process of the planographic printing plate precursor, the entire surface of planographic printing plate precursor may be heated before exposure, during exposure, or in anytime between exposure and development, if needed. The image forming reaction in the photosensitive layer is promoted by the heating, whereby advantages such as improvement of sensitivity or printing durability, and stabilization of sensitivity can be attained. Furthermore, for the purpose of improving the image strength or printing durability, it is also effective to perform a post-heating of the entire surface of an image after development, or to perform an exposure of the entire surface of the image after development. In general, the heating before development is preferably performed under a moderate condition of 150° C. or less. When the heating is performed at 150° C. or less, the problem of fogging in a non-image area does not arise. The heating after development is performed under harsh conditions. That is, the temperature is usually in the range of from 200° C. to 500° C. Sufficient image strengthening action can be obtained at 200° C. or higher, and problems such as deterioration of the support or thermal decomposition of an image area are not caused at 500° C. or less.

EXAMPLES

Hereinafter, the invention will be explained by way of examples in more detail, but without departing from the spirit and scope of the invention, the invention is not limited to the following Examples. In addition, the term "part" is mass basis, and "%" is "% by mass", unless otherwise specified.

First, the details of the specific oxime compounds (Specific Compound 1 to Specific Compound 11) used in Examples and the comparative compounds (Comparative Compound 1 to Comparative Compound 4) used in Comparative Examples are shown.

In the following, synthetic methods of Specific Compound 1 to Specific Compound 11 are shown.

| Compound Number | Structure |
|---|---|
| Specific Compound 1 | 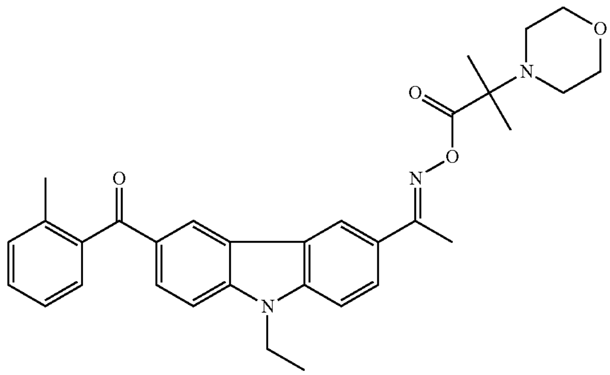 [SMILES: CCn1c2ccc(C(=O)c3ccccc3C)cc2c2cc(/C(C)=N/OC(=O)C(C)(C)N3CCOCC3)ccc21] |
| Specific Compound 2 | 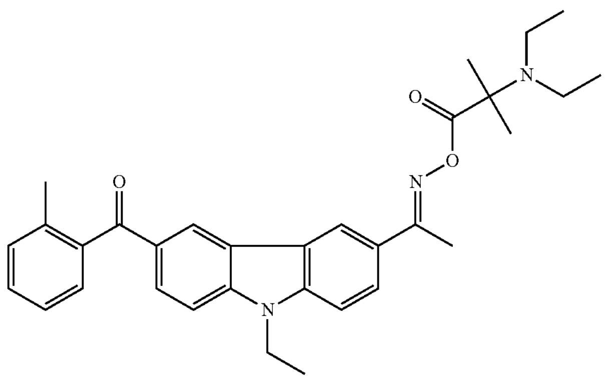 [SMILES: CCN(CC)C(C)(C)C(=O)O/N=C(\C)c1ccc2c(c1)c1cc(C(=O)c3ccccc3C)ccc1n2CC] |
| Specific Compound 3 | 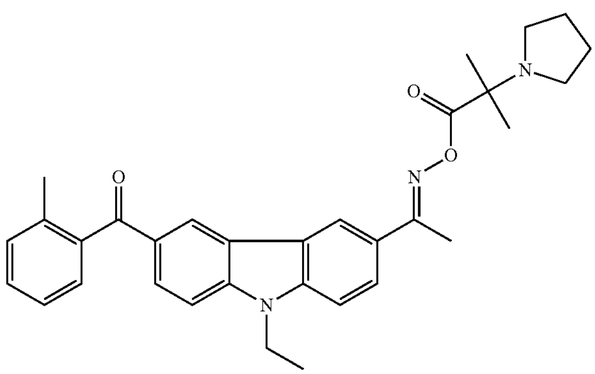 [SMILES: CCn1c2ccc(C(=O)c3ccccc3C)cc2c2cc(/C(C)=N/OC(=O)C(C)(C)N3CCCC3)ccc21] |
| Specific Compound 4 | 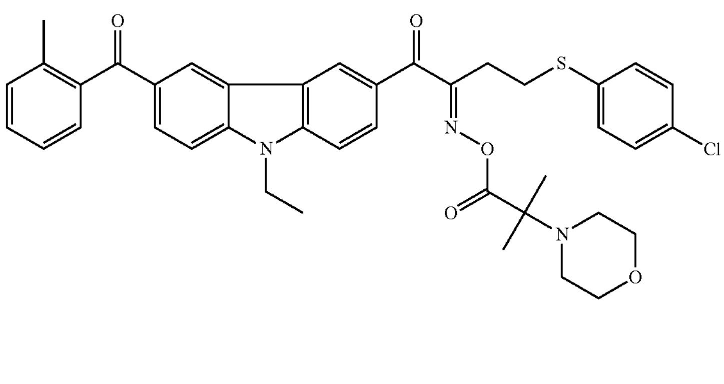 [SMILES: CCn1c2ccc(C(=O)/C(CCSc3ccc(Cl)cc3)=N/OC(=O)C(C)(C)N3CCOCC3)cc2c2cc(C(=O)c3ccccc3C)ccc21] |

-continued
| Compound Number | Structure |
|---|---|
| Specific Compound 5 | 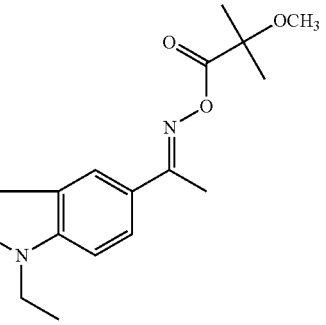 |
| Specific Compound 6 | 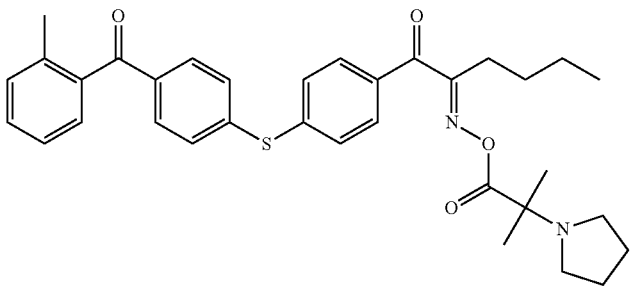 [SMILES: CCCC/C(=N\OC(=O)C(C)(C)N1CCCC1)C(=O)c1ccc(Sc2ccc(C(=O)c3ccccc3C)cc2)cc1] |
| Specific Compound 7 | 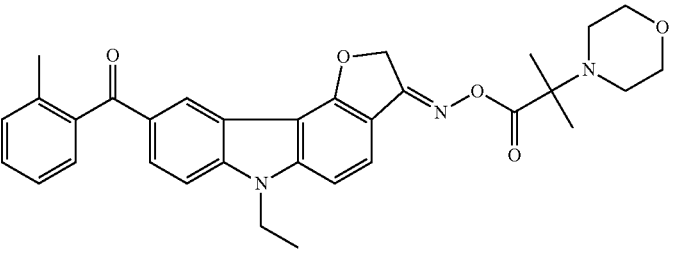 [SMILES: CCn1c2ccc(C(=O)c3ccccc3C)cc2c2c3c(ccc21)/C(=N/OC(=O)C(C)(C)N1CCOCC1)CO3] |
| Specific Compound 8 | 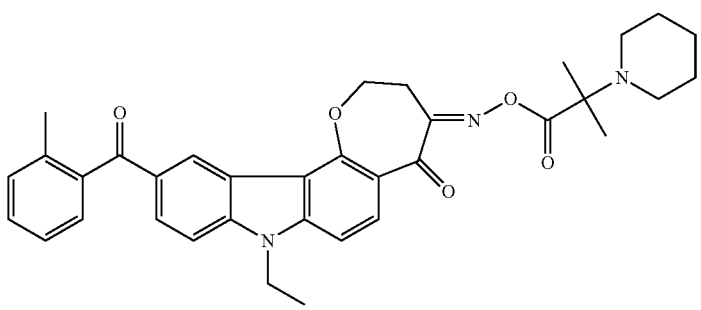 [SMILES: CCn1c2ccc(C(=O)c3ccccc3C)cc2c2c3c(ccc21)C(=O)/C(=N/OC(=O)C(C)(C)N1CCCCC1)CCO3] |
| Specific Compound 9 | 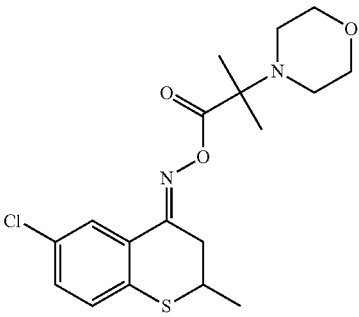 [SMILES: CC1C/C(=N\OC(=O)C(C)(C)N2CCOCC2)c2cc(Cl)ccc2S1] |

| Compound Number | Structure |
|---|---|
| Specific Compound 10 | 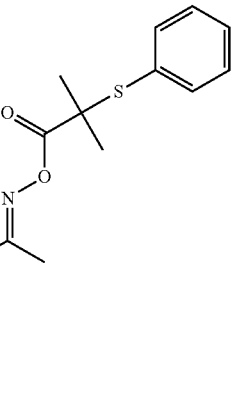 |
| Specific Compound 11 | 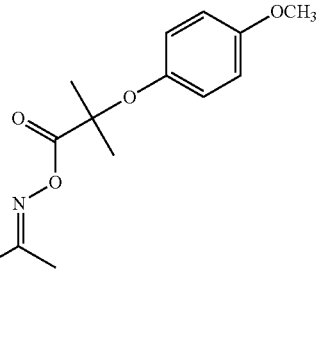 |
| Comparative Compound 1 | IRGACURE OXE 01 (manufactured by Chiba Speciality Chemicals) |
| Comparative Compound 2 | IRGACURE OXE 02 (manufactured by Chiba Speciality Chemicals) |
| Comparative Compound 3 | 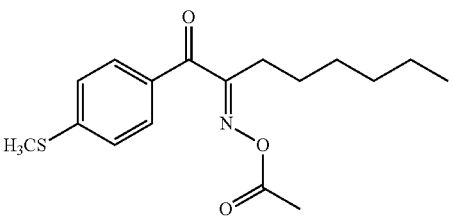 |
| Comparative Compound 4 | 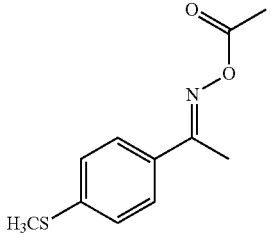 |

(Synthesis of α Hetero Compound)

Synthesis of α-Morpholino Isobutyric Acid Hydrochloride

Ethyl 2-bromopropionate (0.125 moles) was diluted with 75 ml of toluene, and morpholine (0.3 moles) was added thereto, followed by stirring for 10 hours at room temperature. White solid was removed by filtration, and then the filtrate was distilled to obtain 2-morpholinopropionic acid ethyl ester (0.105 moles).

Diisopropyl amine (0.12 moles) was added to a flask and diluted with 40 mL of toluene. The resultant was cooled to −78° C. under nitrogen, and then a hexane solution of n-butyl lithium (0.11 moles) was added thereto, followed by stirring at −78° C. for 1 hour. To this, 2-morpholinopropionic acid ethyl ester (0.105 moles) was added and the resultant was further stirred for 1 hour, and iodomethane (0.21 moles) was added thereto and after the temperature was restored to room temperature, the mixture was stirred for 1 hour. The reaction mixture was quenched with ice water, extracted with ethyl acetate and washed with a saturated sodium chloride aqueous solution, and then the organic layer was dried over magnesium sulphate. The solvent was evaporated, and the residue was purified by column chromatography (hexane/ethyl acetate=4/1) to obtain α-morpholino isobutyric acid ethyl ester (0.55 moles).

This was refluxed with 5N aqueous hydrochloric acid for 2 hours, and the aqueous hydrochloric acid was removed. To the obtained residue, acetone was added and the generated white solid was recovered by filtration to obtain α-morpholino isobutyric acid hydrochloride (0.40 moles).

($^1$H-NMR 300 MHz deuterated chloroform/deuterated pyridine): 1.76 (s, 6H), 3.42 (m, 4H), 4.13 (m, 2H)

Synthesis of α-Pyrrolidino Isobutyric Acid Hydrochloride

To ethyl 2-bromoisobutyrate (0.1 moles), 100 ml of toluene was added, and the mixture was cooled to 0° C. To this, pyrrolidine (0.4 moles) was dropped over 10 minutes. The temperature was restored to room temperature, and then the reaction liquid was further stirred at for 3 hours. A pyrrolidino hydrobromide layer was removed by liquid separation, and a solvent in the toluene layer was distilled away. Further, distillation under reduced pressure was conducted to obtain ethyl α-pyrrolidino isobutyrate (0.082 moles).

This was refluxed with 5N aqueous hydrochloric acid for 2 hours, and the aqueous hydrochloric acid was distilled away. To the obtained residue, acetone was added and the generated white solid was recovered by filtration to obtain α-pyrrolidino isobutyric acid hydrochloride (0.04 moles).

($^1$H-NMR 300 MHz deuterated chloroform/deuterated pyridine): 1.81 (s, 6H), 2.14 (m, 4H), 3.75 (m, 4H)

Synthesis of α-Diethylamino Isobutyric Acid Hydrochloride

To ethyl 2-bromopropionate (0.15 moles), diethylamine (0.4 moles) was added, followed by stirring for 10 hours at room temperature. White solid was removed by filtration, and then the filtrate was distilled to obtain 2-diethylaminopropionic acid ethyl ester (0.120 moles).

Diisopropyl amine (0.15 moles) was added to a flask and diluted with 50 mL of toluene. The resultant was cooled to −78° C. under nitrogen, and then a hexane solution of n-butyl lithium (0.13 moles) was added thereto, followed by stirring at −78° C. for 1 hour. Further, the mixture was heated to 0° C. and stirred for 1 hour. To this, 2-diethylaminopropionic acid ethyl ester (0.11 moles) was added and the resultant was further stirred for 1 hour, and iodomethane (0.23 moles) was added thereto, and then the temperature was restored to room temperature and the mixture was stirred for 1 hour. The reaction mixture was quenched with ice water, extracted with ethyl acetate and washed with a saturated sodium chloride aqueous solution, and then the organic layer was dried over magnesium sulphate. The solvent was distilled away, and then the residue was purified by column chromatography (hexane/ethyl acetate=4/1) to obtain α-diethylamino isobutyric acid ethyl ester (0.50 moles).

This was refluxed with a 5N aqueous hydrochloric acid for 2 hours, and the aqueous hydrochloric acid was distilled away. The obtained residue was dried by heating under vacuum (1 mmHg, 50° C.) for 6 hours to obtain α-diethylamino isobutyric acid hydrochloride (0.5 moles). ($^1$H-NMR 300 MHz deuterated chloroform/deuterated pyridine): 1.61 (t, J=7.5 Hz, 6H), 1.92 (s, 6H), 3.42 (m, 4H)

Synthesis Example 1

Synthesis of Specific Compound 1 which is a Specific Oxime Compound

1-[6-(2-methylbenzoyl)-9-ethyl-9H-carbazole-3-yl]ethanoneoxime (12 m moles) and α-morpholino isobutyric acid hydrochloride (12 m moles) were suspended in 20 ml of methylene chloride. This was cooled to 0° C., and then, 4-dimethylaminopyridine (24 m moles) and dicyclohexylcarbodiimide (13 m moles) were added thereto, and the resultant was stirred at 0° C. for 1 hour. The mixture was extracted with chloroform and then, washed with a saturated sodium chloride aqueous solution. The organic layer was dried over magnesium sulphate and the solvent in the organic layer was distilled away. The obtained residue was purified by silica gel column chromatography (hexane/ethyl acetate=4/1) to obtain 7.6 m moles of the intended specific compound 1.

The structure of the obtained specific compound 1 was identified by NMR.

($^1$H-NMR 300 MHz deuterated chloroform): 1.47 (s, 6H), 1.49 (t, 3H, J=7.2 Hz), 2.35 (s, 3H), 2.52 (s, 3H), 2.74 (t, 4H, J=4.5 Hz), 3.75 (t, 4H, J=4.5 Hz), 4.42 (q, 2H, J=7.2 Hz), 7.26 to 7.47 (m, 6H), 7.98 (d, 1H, J=8.4 Hz), 8.11 (d, 1H, J=8.4 Hz), 8.45 (s, 1H), 8.52 (s, 1H)

The molar extinction coefficient of the specific compound 1 at 365 nm in accordance with the measuring method described above was 1580 in ethyl acetate.

Synthesis Example 2

Synthesis of Specific Compound 2 which is a Specific Oxime Compound

The specific compound 2 was synthesized in the same manner as in the Synthesis Example 1 except that α-diethylamino isobutyric acid hydrochloride was used in place of α-pyrrolidino isobutyric acid hydrochloride.

The structure of the obtained specific compound 2 was identified by NMR.

($^1$H-NMR 300 MHz deuterated chloroform): 1.45 (s, 6H), 1.49 (t, 3H, J=7.2 Hz), 1.55 (t, 6H, J=7.2 Hz), 2.35 (s, 3H), 2.54 (s, 3H), 2.90 (m, 4H), 4.42 (q, 2H, J=7.2 Hz), 7.26 to 7.47 (m, 6H), 7.98 (d, 1H, J=8.4 Hz), 8.11 (d, 1H, J=8.4 Hz), 8.45 (s, 1H), 8.52 (s, 1H)

The molar extinction coefficient of the specific compound 2 at 365 nm in accordance with the same measuring method as described above was 1600 in ethyl acetate.

Synthesis Example 3

Synthesis of Specific Compound 3 which is a Specific Oxime Compound

The specific compound 3 was synthesized in the same manner as in the Synthesis Example 1 except that α-pyrrolidino isobutyric acid hydrochloride was used in place of α-pyrrolidino isobutyric acid hydrochloride.

The structure of the obtained specific compound 3 was identified by NMR.

($^1$H-NMR 300 MHz deuterated chloroform): 1.49 (t, 3H, J=7.2 Hz), 1.55 (s, 6H) 1.82 (m, 4H) 2.35 (s, 3H), 2.51 (s, 3H), 2.93 (m, 4H), 4.42 (q, 2H, J=7.2 Hz), 7.26 to 7.47 (m, 6H), 7.98 (d, 1H, J=8.4 Hz), 8.11 (d, 1H, J=8.4 Hz), 8.45 (s, 1H), 8.52 (s, 1H)

The molar extinction coefficient of the specific compound 3 at 365 nm in accordance with the same measuring method as described above was 1520 in ethyl acetate.

Synthesis Example 4

Synthesis of Compound 4 which is a Specific Oxime Compound

1-[6-(2-methylbenzoyl)-9-ethyl-9H-carbazole-3-yl]buthanone-4-(4-chlorophenylthio)-2-oxime (16 m moles)

and α-morpholino isobutyric acid hydrochloride (15 m moles) were suspended in 40 ml of methylene chloride. This was cooled to 0° C., and then, 4-dimethylaminopyridine (30 m moles) and dicyclohexyl carbodiimide (15 m moles) were added thereto, and the resultant was stirred at 0° C. for 1 hour. The mixture was extracted with chloroform and then, washed with a saturated sodium chloride aqueous solution. The organic layer was dried over magnesium sulphate and the solvent in the organic layer was distilled away. The obtained residue was purified by silica gel column chromatography (hexane/ethyl acetate=4/1) to obtain 5.3 m mole of the intended specific compound 4.

The structure of the obtained specific compound 4 was identified by NMR.

($^1$H-NMR 300 MHz deuterated chloroform): 1.40 (s, 6H), 1.49 (t, 3H, J=7.2 Hz), 2.37 (s, 3H), 2.65 (t, 4H, J=4.5 Hz), 3.21 (m, 4H) 3.72 (t, 4H, J=4.5 Hz), 4.42 (q, 2H, J=7.2 Hz), 7.26 to 7.47 (m, 6H), 8.08 (d, 1H, J=8.4 Hz), 8.35 (d, 1H, J=8.4 Hz), 8.58 (s, 1H), 8.89 (s, 1H)

The molar extinction coefficient of the specific compound 4 at 365 nm in accordance with the same measuring method as described above was 15600 in ethyl acetate.

Specific compounds 5 to 11 which are the above-described specific oxime compounds were synthesized in the same manners as those in the Synthesis Examples 1 to 4.

The structures of the comparative compound 1 and comparative compound 2 are as follows.

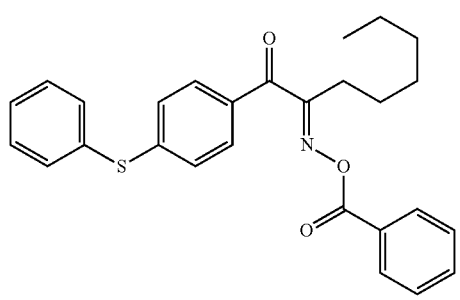

IRGACURE OXE 01

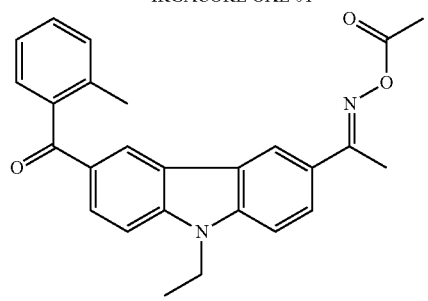

IRGACURE OXE 02

Example 1-1

Preparation of Photopolymerizable Composition 1 and Evaluation Thereof

The photopolymerizable composition 1 was prepared as described below, and the sensitivity thereof was evaluated.

A photopolymerizable composition which contained 0.08 mmol of Specific Compound 1 as a specific oxime compound, 1 g of pentaerythritol tetraacrylate as a radical polymerizable compound, 1 g of polymethyl methacrylate (manufactured by Aldrich Corporation; weight average molecular weight: ca. 996,000) as a binder resin, and 16 g of cyclohexanone as a solvent, was prepared.

The obtained polymerizable composition 1 was used as a coating liquid, and was applied on a glass plate by using a spin coater, and the coated liquid was dried at 40° C. for 10 minutes to form a coated film having a thickness of 1.5 μm. A 21√2 step tablet (gray scale film manufacture by Dainippon Screen Mfg. Co., Ltd.) was placed on the coated film, and after the film was exposed to light from a 500 mW high pressure mercury lamp (manufactured by Ushio, Inc.) for 30 seconds through a heat ray cut filter, the film was soaked in toluene for 60 seconds to perform a development process.

The sensitivity was evaluated based on the number of steps corresponding to the step tablet, at which the film was completely cured and insolubilized. As a result, it was found that the step number of sensitivity was 7.

In addition, the step number of sensitivity indicates that the sensitivity is higher as the number of step is greater.

Example 1-2 to Example 1-11, and Comparative Example 1-1 to Comparative Example 1-4

The photopolymerizable composition 2 to the photopolymerizable composition 15 were each prepared in the same manner as in Example 1-1, except that Specific Compound 1 (0.08 mmol) used as the specific oxime compound used in Example 1-1 was replaced with each compound (0.08 m mole) shown in the list above (Specific Compound 2 to Specific Compound 11 and Comparative Compound 1 to Comparative Compound 4). The step number of sensitivity thereof was evaluated in the same manner as in Example 1-1.

The evaluation results of Examples 1-1 to 1-11 and Comparative Example 1-1 to Comparative Example 1-4 are shown in the following Table 1.

TABLE 1

| | Photopolymerizable Composition | Specific Compound or Comparative Compound | Sensitivity Step Under Nitrogen Atmosphere | Sensitivity Step Under Air Atmosphere |
|---|---|---|---|---|
| Example 1-1 | 1 | Specific Compound 1 | 7 | 7 |
| Example 1-2 | 2 | Specific Compound 2 | 8 | 8 |
| Example 1-3 | 3 | Specific Compound 3 | 7 | 7 |
| Example 1-4 | 4 | Specific Compound 4 | 8 | 8 |
| Example 1-5 | 5 | Specific Compound 5 | 7 | 6 |
| Example 1-6 | 6 | Specific Compound 6 | 8 | 8 |
| Example 1-7 | 7 | Specific Compound 7 | 9 | 9 |
| Example 1-8 | 8 | Specific Compound 8 | 9 | 9 |
| Example 1-9 | 9 | Specific Compound 9 | 9 | 9 |
| Example 1-10 | 10 | Specific Compound 10 | 8 | 8 |
| Example 1-11 | 11 | Specific Compound 11 | 7 | 6 |
| Comparative Example 1-1 | 12 | Comparative Compound 1 | 5 | 3 |
| Comparative Example 1-2 | 13 | Comparative Compound 2 | 5 | 2 |

TABLE 1-continued

| | Photopoly-merizable Composition | Specific Compound or Comparative Compound | Sensitivity Step | |
|---|---|---|---|---|
| | | | Under Nitrogen Atmosphere | Under Air Atmosphere |
| Comparative Example 1-3 | 14 | Comparative Compound 3 | 4 | 2 |
| Comparative Example 1-4 | 15 | Comparative Compound 4 | 4 | 2 |

From the Table 1, the followings are shown. In each of Examples 1-1 to 1-11 of the present invention, the number of step of sensitivity is higher and the composition is cured with a higher sensitivity both under nitrogen atmosphere and under air atmosphere, when compared to those of the Comparative Examples 1-1 to 1-4. It is general that in the radical polymerization under air atmosphere, the sensitivity is lowered by undergoing the inhibition of polymerization due to the presence of oxygen. It is found that in each of Comparative Examples 1-1 to 1-4, reduction in the number of step of sensitivity and the encounter with inhibition of polymerization of the composition are larger under oxygen-containing air atmosphere than those under nitrogen atmosphere. On the other hand, it is found that, in each of Examples 1-1 to 1-11 of the present invention, the number of step of sensitivity under nitrogen atmosphere is rarely different from the number under air atmosphere, and these compositions hardly undergo oxygen inhibition even under air atmosphere. Among these Examples, in Examples 1-1 to 1-4 and 1-6 to 1-9 where α-aminoalkyl radial or α-thioalkyl radical is thought to be generated, these compositions show stronger resistance to oxygen than those in Examples 5, 10 and 11.

Example 2-1

(1) Manufacture of Colored Photopolymerizable Composition A-1

As a photopolymerizable composition for forming a color filter, a negative-working colored photopolymerizable composition A-1 containing a colorant (pigment) was prepared, and by using this, a color filter was produced.

(1-1) Preparation of Pigment Dispersion (P1)

A mixed solution composed of 40 parts of a mixture of C.I. Pigment Green 36 and C. I. Pigment Yellow 219 at the mass ratio of 30 to 70 as a pigment, 10 parts (about 4.51 parts in terms of solid content) of BYK2001 (solid concentration: 45.1%, manufactured by BYK-Chemie GmbH) as a dispersant, and 150 parts of ethyl 3-ethoxypropionate as a solvent, was mixed and dispersed using a beads mill for 15 hours, thereby obtaining a pigment dispersion (P1).

As a result of measurement of the average particle diameter of the pigment in accordance with a dynamic light scattering method, the average particle diameter of the pigment in the obtained pigment dispersion (P1) was 200 nm.

(1-2) Preparation of Colored Photopolymerizable Composition A-1 (Coating Liquid)

The components of the following composition A-1 were mixed and dissolved to prepare a colored photopolymerizable composition A-1.

<Composition A-1>

| Pigment dispersion (P1) | 600 parts |
|---|---|
| Alkali soluble resin (benzyl methacrylate/methacrylic acid/hydroxyethyl methacrylate copolymer; molar ratio: 80/10/10; Mw: 10,000) | 200 parts |
| Polymerizable compound: dipentaerythritol hexaacrylate | 60 parts |
| Specific oxime compound: Specific Compound 1 | 60 parts |
| Solvent: propylene glycol monomethylether acetate | 1,000 parts |
| Surfactant (TETRONIC 150R1 (trade name): manufactured by BASF SE. | 1 part |
| γ-Methacryloxypropyl triethoxysilane | 5 parts |

(2) Production of Color Filter (2-1) Formation of Colored Photopolymerizable Composition Layer The thus-obtained colored photopolymerizable composition A-1 containing the pigment was coated by slit-coating under the following conditions on a glass substrate of 550 mm×650 mm. Thereafter, the substrate coated with the composition was subjected to a vacuum drying and prebaking (at 80° C. for 80 seconds), thereby forming a photopolymerizable composition-coated film (colored photopolymerizable composition layer).

Slit-Coating Conditions

Clearance of the opening portion at the leading end of coating head: 50 μm;

Coating speed: 100 mm/second;

Clearance between the substrate and the coating head: 150 μm;

Thickness of coating (dry thickness): 2 μm; and

Temperature during coating: 23° C.

(2-2) Exposure and Development

Thereafter, the colored photopolymerizable composition layer was subjected to pattern exposure using a 2.5 kW ultra-high-pressure mercury lamp. The entire surface of the colored photopolymerizable composition layer after exposure was developed with a 10% aqueous solution of an inorganic developer (CD (trade name), manufactured by FUJIFILM Electronic Materials Co., Ltd.) for 60 seconds.

(2-3) Heat-Processing

Thereafter, pure water was sprayed in a shower-like flow onto the colored photopolymerizable composition layer to remove the developer, and subsequently, the colored photopolymerizable composition layer was heated in an oven at 220° C. for one hour (post-baking), thereby obtaining a color filter including the glass substrate having a colored pattern thereon.

(3) Performance Evaluation

The storage stability and exposure sensitivity of the colored photopolymerizable composition; the developability when a colored pattern was formed on the glass plate by using the colored photopolymerizable composition; the coloration due to heat-aging of the obtained colored pattern; the adhesion to the substrate; the pattern cross-sectional profile and the post-heating pattern cross-sectional profile were evaluated. The evaluation results are collectively shown in Tables 2.

(3-1) Storage Stability of Colored Photopolymerizable Composition

After storage of the colored photopolymerizable composition for one month at room temperature, the degree of deposition of foreign matters was visually inspected and evaluated in accordance with the following evaluation criteria:
Evaluation Criteria
A: No deposition is recognized;
B: Deposition is slightly recognized; and
C: Deposition is recognized.
(3-2) Exposure Sensitivity of Colored Photopolymerizable Composition The colored photopolymerizable composition was coated by spin-coating on a glass substrate, and was dried to form a coated layer having a layer thickness of 1.0 μm. The spin coating conditions were set to 300 rpm for 5 seconds, followed by 800 rpm for 20 seconds, and the drying conditions were set to 100° C. for 80 seconds. The obtained coated film was exposed to light through a test photomask having a line width of 2.0 μm with various exposure amounts in the range of from 10 mJ/cm$^2$ to 1,600 mJ/cm$^2$ by using a proximity type exposure machine equipped with an ultra-high-pressure mercury lamp (manufactured by Hitachi High-Tech Electronics Engineering Co., Ltd.). Next, the exposed coated film was developed using a 60% CD-2000 (a product of FUJIFILM Electronic Materials Co., Ltd.) developer under the condition of 25° C. for 60 seconds. Subsequently, the coated film was rinsed with running water for 20 seconds, and was spray dried, thereby finishing the patterning.

Evaluation of the exposure sensitivity was performed. The exposure sensitivity was defined by the minimum exposure amount necessary to achieve 95% or more of the film thickness after development in the area irradiated with light in the exposure process, with respect to 100% of the film thickness before the exposure. This definition indicates that the sensitivity is higher as the value of exposure sensitivity is smaller.

(3-3) Developability, Pattern Cross-Sectional Profile, and Adhesion to Substrate Evaluation of the developability, the adhesion to a substrate, the change in color at the time of forced heating with age, and the pattern cross-sectional profile was performed by observing the surface of the substrate and the cross-sectional profile after performing the post-baking in "2-3. heat-processing" by using an optical microscope photograph and an SEM photograph in the usual manner. The details of the valuation method are as follows.

Developability

The developability was evaluated by observing the presence of residues in the area where light was not irradiated (unexposed portion) in the exposure process. The evaluation criteria are as follows.
Evaluation Criteria
A: No residues in the unexposed area are recognized at all;
B: Residues in the unexposed area are slightly recognized, but were not at a level of being problematic in practical use; and
C: Residues are remarkably recognized in the unexposed area.

Adhesion to Substrate

The adhesion to substrate was evaluated by observing whether or not defects in pattern were caused. The evaluation criteria are as follows.
Evaluation Criteria
A: Defects in pattern are not recognized at all;
B: Defects in pattern are hardly recognized, but deficit in pattern were recognized in part;
and C: A large number of defects in pattern are recognized significantly.

Evaluation of Coloration Caused by Forced Heat-Aging

The photopolymerizable composition layer (colored pattern) after exposure and development was heated using a hot plate at 200° C. for one hour. The color difference ΔEab* before and after heating by using MCPD-3000 manufactured by Otsuka Electronics Co., Ltd was evaluated in accordance with the following evaluation criteria;
Evaluation Criteria
A: ΔEab*≤5
B: 5<ΔEab*<8
C: ΔEab*≥8

Pattern Cross-Sectional Profile

The cross-sectional profile of the formed pattern was observed using a scanning electron microscopy (S-4300, manufactured by Hitachi Corporation), and evaluated. As the cross-sectional profile of the pattern, a forward tapered profile is most desirable, and a rectangular profile is secondarily desirable, but a reverse tapered profile is not desirable.

Post-Heating Pattern Cross-Sectional Profile

The cross-sectional profile of the pattern that was formed after the post-baking performed in the "2-3. heat-processing" was observed and evaluated in the same manner as the above. As the cross-sectional profile of the pattern, a forward tapered profile is most desirable, and a rectangular profile is secondarily desirable, but a reverse tapered profile is not desirable.

Examples 2-2 to 2-17, and Comparative Examples 2-1 to 2-3

Colored photopolymerizable compositions A-2 to A-17 and A'-1 to A'-3 were respectively produced in the same manner as in Example 2-1, except that 60 parts by mass of Specific Compound 1 (specific oxime compound) included in the composition A-1, which was used in the preparation of the colored photopolymerizable composition A-1 in Example 2-1, was replaced with the compounds and the amounts as shown in the following Tables 2 and furthermore, the sensitizers and co-sensitizers, of which kinds and amounts are shown in Table 2, were added in Examples 2-10 to 2-17, and color filters were prepared. Furthermore, the evaluation was performed in the same manner as in Example 2-1. The results are shown in Table 3.

TABLE 2

| | Colored polymerizable composition | Polymerization initiator | | | Sensitizer | | Co-sensitizer | |
|---|---|---|---|---|---|---|---|---|
| | | Specific compound | Comparative compound | Content (parts) | Kind | Content (parts) | Kind | Content (parts) |
| Example 2-1 | A-1 | 1 | — | 60 | — | — | — | — |
| Example 2-2 | A-2 | 2 | — | 60 | — | — | — | — |
| Example 2-3 | A-3 | 3 | — | 60 | — | — | — | — |
| Example 2-4 | A-4 | 4 | — | 60 | — | — | — | — |

TABLE 2-continued

|  | Colored polymerizable composition | Polymerization initiator | | | Sensitizer | | Co-sensitizer | |
| --- | --- | --- | --- | --- | --- | --- | --- | --- |
|  |  | Specific compound | Comparative compound | Content (parts) | Kind | Content (parts) | Kind | Content (parts) |
| Example 2-5 | A-5 | 5 | — | 60 | — | — | — | — |
| Example 2-6 | A-6 | 6 | — | 60 | — | — | — | — |
| Example 2-7 | A-7 | 7 | — | 60 | — | — | — | — |
| Example 2-8 | A-8 | 8 | — | 60 | — | — | — | — |
| Example 2-9 | A-9 | 9 | — | 60 | — | — | — | — |
| Example 2-10 | A-10 | 2 | — | 50 | A-1 | 10 | — | — |
| Example 2-11 | A-11 | 2 | — | 50 | A-2 | 10 | — | — |
| Example 2-12 | A-12 | 2 | — | 50 | A-3 | 10 | — | — |
| Example 2-13 | A-13 | 2 | — | 50 | — | — | F1 | 10 |
| Example 2-14 | A-14 | 2 | — | 40 | A-1 | 10 | F1 | 10 |
| Example 2-15 | A-15 | 2 | — | 40 | A-2 | 10 | F2 | 10 |
| Example 2-16 | A-16 | 2 | — | 40 | A-2 | 10 | F3 | 10 |
| Example 2-17 | A-17 | 2 | — | 40 | — | — | F3 LD-5 | 10 10 |
| Comp. example 2-1 | A'-1 | — | 1 | 60 | — | — | — | — |
| Comp. Example 2-2 | A'-2 | — | 2 | 60 | — | — | — | — |
| Comp. Example 2-3 | A'-3 | — | 3 | 60 | — | — | — | — |

TABLE 3

|  | Storage stability | Exposure sensitivity (mJ/cm$^2$) | Developability | Change in color in forced heat-aging | Adhesion to substrate | Pattern cross-sectional profile | Post-heating pattern cross-sectional profile |
| --- | --- | --- | --- | --- | --- | --- | --- |
| Example 2-1 | A | 120 | A | A | A | Forward tapered | Forward tapered |
| Example 2-2 | A | 110 | A | A | A | Forward tapered | Forward tapered |
| Example 2-3 | A | 90 | A | A | A | Forward tapered | Forward tapered |
| Example 2-4 | A | 90 | A | A | A | Forward tapered | Forward tapered |
| Example 2-5 | A | 170 | A | A | A | Forward tapered | Forward tapered |
| Example 2-6 | A | 120 | A | A | A | Forward tapered | Forward tapered |
| Example 2-7 | A | 50 | A | A | A | Forward tapered | Forward tapered |
| Example 2-8 | A | 80 | A | A | A | Forward tapered | Forward tapered |
| Example 2-9 | A | 60 | A | A | A | Forward tapered | Forward tapered |
| Example 2-10 | A | 90 | A | A | A | Forward tapered | Forward tapered |
| Example 2-11 | A | 80 | A | A | A | Forward tapered | Forward tapered |
| Example 2-12 | A | 90 | A | A | A | Forward tapered | Forward tapered |
| Example 2-13 | A | 80 | A | A | A | Forward tapered | Forward tapered |
| Example 2-14 | A | 80 | A | A | A | Forward tapered | Forward tapered |

TABLE 3-continued

| | Storage stability | Exposure sensitivity (mJ/cm$^2$) | Developability | Change in color in forced heat-aging | Adhesion to substrate | Pattern cross-sectional profile | Post-heating pattern cross-sectional profile |
|---|---|---|---|---|---|---|---|
| Example 2-15 | A | 80 | A | A | A | Forward tapered | Forward tapered |
| Example 2-16 | A | 70 | A | A | A | Forward tapered | Forward tapered |
| Example 2-17 | A | 70 | A | A | A | Forward tapered | Forward tapered |
| Comp. example 2-1 | A | 500 | B | B | C | Reverse tapered | Rectangular |
| Comp. Example 2-2 | A | 300 | B | C | B | Reverse tapered | Rectangular |
| Comp. Example 2-3 | A | 700 | C | B | B | Reverse tapered | Rectangular |

In Tables 2, 4, 6, 8, 10, 11 and 14, the numerical values 1 to 9 of the "specific compound" column in the "polymerization initiator" column indicate Specific Compounds 1 to Specific Compound 9, respectively, and the numerical values 1 to 3 of the "comparative compound" column indicate Comparative Compound 1 to Comparative Compound 3, respectively.

The sensitizers A1 to A3 and the co-sensitizers F1 to F3 and LD-5 shown in Tables 2, 4, 6, 8, 10, 11 and 14 are the following compounds.

A1: 4,4-bisdiethyl aminobenzophenone
A2: diethyl thioxanthone

A3:

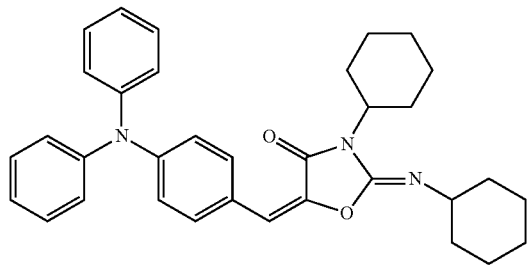

F1: 2-mercaptobenzimidazole
F2: 2-mercaptobenzothiazole
F3: N-phenyl-2-mercaptobenzimidazole
LD-5: 2,2'-bis(o-chlorophenyl)-4,4',5,5'-tetraphenylbiimidazole From the results of Table 3, it is understood that the colored photopolymerizable composition of each Example, which contains the specific oxime compound (Specific Compound 1 to Specific Compound 9), is excellent in the storage stability (stability with the passage of time). Further, it is understood that each of these colored photopolymerizable compositions has high exposure sensitivity and excellent developability when used for forming a colored pattern of a color filter, and each of them does not cause coloration due to the heat-aging of the obtained colored pattern, and each of them is excellent in any of the adhesion to the substrate, the pattern cross-sectional profile, and the post-heating pattern cross-sectional profile.

Example 3-1

(1) Preparation of Resist Liquid A

The components of the following composition were mixed and dissolved to prepare a resist liquid A.

—Composition of Resist Liquid—

| | |
|---|---|
| Propylene glycol monomethylether acetate (PGMEA) | 19.20 parts |
| Ethyl lactate | 36.67 parts |
| Resin (40% PGMEA solution of benzyl methacrylate/methacrylic acid/2-hydroxyethyl methacrylate copolymer (molar ratio = 60/22/18)) | 30.51 parts |
| Dipentaerythritol hexaacrylate (polymerizable compound) | 12.20 parts |
| Polymerization inhibitor (p-methoxy phenol) | 0.0061 parts |
| Fluorine-containing surfactant (F-475; manufactured by DIC Corporation) | 0.83 parts |
| Photopolymerization initiator (TAZ-107 (trihalomethyl triazine photopolymerization initiator), manufactured by Midori Kagaku Co., Ltd.) | 0.586 parts |

(2) Manufacture of Silicon Wafer Board with Undercoat Layer

A 6-inch silicon wafer was subjected to a heat processing at 200° C. for 30 minutes in an oven. Subsequently, the resist liquid A was coated on the silicon wafer so as to attain a dry thickness of 2 μm, and further was heat-dried at 220° C. for one hour in an oven to form an undercoat layer, thereby obtaining a silicon wafer board with the undercoat layer.

(3) Preparation of Colored Photopolymerizable Composition B-1

The compounds of the following composition B-1 were mixed, and the colored photopolymerizable composition B-1 containing a colorant (dye) was prepared.
<Composition B-1>

| | |
|---|---|
| Cyclohexanone | 80 parts |
| Colorant: C.I. Acid Blue 108 | 7.5 parts |
| Colorant: C.I. Solvent Yellow 162 | 2.5 parts |
| Radical polymerizable monomer (polymerizable compound) (a mixture of pentaerythritol triacrylate and dipentaerythritol hexaacrylate with the mass ratio of 3:7) | 7.0 parts |
| Specific Compound 1 (specific oxime compound) | 2.5 parts |
| Glycerol propoxylate (number average molecular weight Mn: 1,500) | 0.5 parts |

(4) Evaluation of Storage Stability of Colored Photopolymerizable Composition B-1 (Coating Liquid)

After storing the colored photopolymerizable composition B-1 for one month at room temperature, the degree of deposition of foreign matters was evaluated by visually inspecting in accordance with the following judgment criteria. The results are shown in the following Table 5.
—Judgment Criteria—
A: Deposition is not recognized;
B: Deposition is slightly recognized; and
C: Deposition is recognized.

(5) Production and Evaluation of Color Filter Formed Using Colored Photopolymerizable Composition B-1

The colored photopolymerizable composition B-1 prepared in the above section (3) was coated on the undercoat layer of the silicon wafer board having the undercoat layer, which was obtained in the above section (2), to form a coated film of the colored photopolymerizable composition. The coated film was subjected to a heat processing (prebaking) using a hot plate at 100° C. for 120 seconds so that the dry thickness of the coated film became 0.9 µm.

Subsequently, the coated film was irradiated with light of a wavelength of 365 nm at an exposure amount of 10 to 1,600 mJ/cm² through an island pattern mask having a 2 µm-square pattern by using an i-line stepper exposure machine FPA-3000i5+ (manufactured by Canon Inc.).

Thereafter, the silicon wafer board having the light-irradiated coated film thereon was placed on the horizontally rotary table of a spin shower development machine (DW-30 type; manufactured by Chemitronics Co., Ltd.), and was paddle developed using CD-2000 (manufactured by FujiFilm Electronic Materials Co., Ltd.) at 23° C. for 60 seconds, thereby forming a colored pattern on the silicon wafer board.

The silicon wafer board with the colored pattern formed thereon was fixed onto the horizontally rotary table with a vacuum chuck method. While rotating the silicon wafer board by a rotary machine at the number of revolutions of 50 rpm, pure water in a shower-like flow was sprayed from a spray nozzle from above the rotation center to perform a rinse processing, and thereafter, spray drying was performed.

In this way, a color filter having a colored pattern formed on the board was obtained.

Evaluation of the exposure sensitivity was performed. The exposure sensitivity was defined by the minimum exposure amount necessary to achieve 95% or more of the film thickness after development in the area irradiated with light in the exposure process, with respect to 100% of the film thickness before the exposure. This definition indicates that the sensitivity is higher as the value of exposure sensitivity is smaller.

In this case, the size of the colored pattern was measured by using a critical dimension-measurement SEM "S-9260A" (manufactured by Hitachi High-Technologies Corporation). This shows that the curability is sufficient and the sensitivity is high as the pattern size become close to 2 µm.

The results are shown in the following Tables 3.

(7) Evaluation of Developability, Coloration Due to Heat-Aging, Adhesion to Substrate, Pattern Cross-Sectional Profile, and Post-Heating Pattern Cross-Sectional Profile The evaluation of developability, coloration due to heat-aging, adhesion to substrate, pattern cross-sectional profile, and post-heating pattern cross-sectional profile was performed based on the evaluation methods and evaluation criteria performed in Example 2-1.

The results are shown in the following Table 4.

Examples 3-2 to 3-17, and Comparative Example 3-1 to 3-3

Colored photopolymerizable compositions B-2 to B-17 and B'-1 to B'-3 were respectively produced in the same manner as in Example 3-1, except that 2.5 parts of Specific Compound 1 (specific oxime compound) included in the composition B-1, which was used in the preparation of the colored photopolymerizable composition B-1 in Example 3-1, was replaced with the compounds and the amounts as shown in the following Table 4, respectively, and, furthermore, the sensitizers and co-sensitizers, of which kinds and amounts are shown in Table 4, were added in Examples 3-10 to 3-17, and color filters were prepared. Furthermore, the evaluation similar to that of Example 3-1 was performed. The results are shown in Table 5.

TABLE 4

| | Colored polymerizable composition | Polymerization initiator | | | Sensitizer | | Co-sensitizer | |
|---|---|---|---|---|---|---|---|---|
| | | Specific compound | Comparative compound | Content (parts) | Kind | Content (parts) | Kind | Content (parts) |
| Example 3-1 | B-1 | 1 | — | 2.5 | — | — | — | — |
| Example 3-2 | B-2 | 2 | — | 2.5 | — | — | — | — |
| Example 3-3 | B-3 | 3 | — | 2.5 | — | — | — | — |
| Example 3-4 | B-4 | 4 | — | 2.5 | — | — | — | — |
| Example 3-5 | B-5 | 5 | — | 2.5 | — | — | — | — |
| Example 3-6 | B-6 | 6 | — | 2.5 | — | — | — | — |
| Example 3-7 | B-7 | 7 | — | 2.5 | — | — | — | — |
| Example 3-8 | B-8 | 8 | — | 2.5 | — | — | — | — |
| Example 3-9 | B-9 | 9 | — | 2.5 | — | — | — | — |
| Example 3-10 | B-10 | 2 | — | 2.0 | A1 | 0.5 | — | — |
| Example 3-11 | B-11 | 4 | — | 2.0 | A2 | 0.5 | — | — |
| Example 3-12 | B-12 | 4 | — | 2.0 | A3 | 0.5 | — | — |
| Example 3-13 | B-13 | 4 | — | 2.0 | — | — | F1 | 0.5 |
| Example 3-14 | B-14 | 4 | — | 1.5 | A2 | 0.5 | F1 | 0.5 |
| Example 3-15 | B-15 | 4 | — | 1.5 | A2 | 0.5 | F2 | 0.5 |
| Example 3-16 | B-16 | 4 | — | 1.5 | A2 | 0.5 | F3 | 0.5 |
| Example 3-17 | B-17 | 4 | — | 1.5 | | | F3 LD-5 | 0.5 0.5 |
| Comp. example 3-1 | B'-1 | — | 1 | 2.5 | — | — | — | — |
| Comp. Example 3-2 | B'-2 | — | 2 | 2.5 | — | — | — | — |
| Comp. Example 3-3 | B'-3 | — | 3 | 2.5 | — | — | — | — |

TABLE 5

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-1 | A | 1100 | 1.96 | A | A | A | Rectangular | Rectangular |
| Example 3-2 | A | 1200 | 1.97 | A | A | A | Rectangular | Rectangular |
| Example 3-3 | A | 1000 | 1.97 | A | A | A | Rectangular | Rectangular |
| Example 3-4 | A | 900 | 1.97 | A | A | A | Rectangular | Rectangular |
| Example 3-5 | A | 1500 | 1.97 | A | A | A | Rectangular | Rectangular |
| Example 3-6 | A | 1400 | 1.97 | A | A | A | Rectangular | Rectangular |
| Example 3-7 | A | 800 | 1.94 | A | A | A | Rectangular | Rectangular |

TABLE 5-continued

|  | Storage stability | Exposure sensitivity (mJ/cm²) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-8 | A | 900 | 1.97 | A | A | A | Rectangular | Rectangular |
| Example 3-9 | A | 900 | 1.97 | A | A | A | Rectangular | Rectangular |
| Example 3-10 | A | 850 | 1.97 | A | A | A | Rectangular | Rectangular |
| Example 3-11 | A | 850 | 1.97 | A | A | A | Rectangular | Rectangular |
| Example 3-12 | A | 800 | 1.98 | A | A | A | Rectangular | Rectangular |
| Example 3-13 | A | 850 | 1.98 | A | A | A | Rectangular | Rectangular |
| Example 3-14 | A | 800 | 1.98 | A | A | A | Rectangular | Rectangular |
| Example 3-15 | A | 800 | 1.98 | A | A | A | Rectangular | Rectangular |
| Example 3-16 | A | 750 | 1.98 | A | A | A | Rectangular | Rectangular |
| Example 3-17 | A | 750 | 1.98 | A | A | A | Rectangular | Rectangular |
| Comp. example 3-1 | A | 3000 | 1.92 | B | B | C | Reverse tapered | Forward tapered |
| Comp. Example 3-2 | A | 2200 | 1.92 | B | C | B | Reverse tapered | Forward tapered |
| Comp. Example 3-3 | A | 5000 | 1.92 | C | C | B | Reverse tapered | Forward tapered |

Example 3-18

In the preparation of the above-mentioned pigment dispersion (P1), a pigment dispersion of C. I. Pigment Red 254 and a pigment dispersion of C. I. Pigment Yellow 139 were obtained in the same manner as in the preparation of P1, except that the sum of C. I. Pigment Green 36 and C. I. Pigment Yellow 219 each of which is a pigment, is replaced respectively with C. I. Pigment Red 254 and C. I. Pigment Yellow 139.

The compounds of the following composition C-1 were mixed, and the colored photopolymerizable composition C-1 containing a colorant (pigment) was prepared.

<Composition C-1>

| | |
|---|---|
| Ethyl 3-ethoxypropionate (solvent) | 17.9 parts |
| Colorant (dispersion of C.I. Pigment Red 254) (solid content: 15% by mass; pigment content in solid content: 60%) | 26.7 parts |
| Colorant (dispersion of C.I. Pigment Yellow 139 (solid content: 15 mass %, pigment content in solid content 60%) | 17.8 parts |
| Radical polymerizable monomer (polymerizable compound) (mixture of 3:7 of pentaerythritol triacrylate and dipentaerythritol hexaacrylate) | 3.5 parts |
| Specific Compound 1 (specific oxime compound) | 0.5 parts |
| Benzyl methacrylate/methacrylic acid copolymer (molar ratio = 70/30) | 2.0 parts |

Examples 3-19 to 3-34, and Comparative Example 3-4 to 3-6

Colored photopolymerizable compositions C-2 to C-17 and C'-1 to C'-3 were produced respectively in the same manner as in Example 3-18, except that 0.5 parts of Specific Compound 1 (specific oxime compound) included in the composition C-1, which was used in the preparation of the colored photopolymerizable composition C-1 in Example 3-18, was replaced with the compounds and the amounts as shown in the following Table 6, respectively, and, furthermore, the sensitizers and co-sensitizers, of which kinds and amounts are shown in Table 6, were added in Example 3-27 to 3-34.

Each of the obtained colored photopolymerizable compositions was evaluated in a manner similar to those in Example 3-1. The results are shown in Table 7.

TABLE 6

| | Colored polymerizable composition | Polymerization initiator Specific compound | Polymerization initiator Comparative compound | Polymerization initiator Content (parts) | Sensitizer Kind | Sensitizer Content (parts) | Co-sensitizer Kind | Co-sensitizer Content (parts) |
|---|---|---|---|---|---|---|---|---|
| Example 3-18 | C-1 | 1 | — | 0.5 | — | — | — | — |
| Example 3-19 | C-2 | 2 | — | 0.5 | — | — | — | — |
| Example 3-20 | C-3 | 3 | — | 0.5 | — | — | — | — |
| Example 3-21 | C-4 | 4 | — | 0.5 | — | — | — | — |
| Example 3-22 | C-5 | 5 | — | 0.5 | — | — | — | — |
| Example 3-23 | C-6 | 6 | — | 0.5 | — | — | — | — |
| Example 3-24 | C-7 | 7 | — | 0.5 | — | — | — | — |
| Example 3-25 | C-8 | 8 | — | 0.5 | — | — | — | — |
| Example 3-26 | C-9 | 9 | — | 0.5 | — | — | — | — |
| Example 3-27 | C-10 | 7 | — | 0.4 | A1 | 0.1 | — | — |
| Example 3-28 | C-11 | 7 | — | 0.4 | A2 | 0.1 | — | — |
| Example 3-29 | C-12 | 7 | — | 0.4 | A3 | 0.1 | — | — |
| Example 3-30 | C-13 | 7 | — | 0.4 | — | — | F1 | 0.1 |
| Example 3-31 | C-14 | 7 | — | 0.3 | A2 | 0.1 | F1 | 0.1 |
| Example 3-32 | C-15 | 7 | — | 0.3 | A2 | 0.1 | F2 | 0.1 |
| Example 3-33 | C-16 | 7 | — | 0.3 | A2 | 0.1 | F3 | 0.1 |
| Example 3-34 | C-17 | 7 | — | 0.3 | A2 | 0.1 | F3 LD-5 | 0.1 0.1 |
| Comp. example 3-4 | C'-1 | — | 1 | 0.5 | — | — | — | — |
| Comp. Example 3-5 | C'-2 | — | 2 | 0.5 | — | — | — | — |
| Comp. Example 3-6 | C'-3 | — | 3 | 0.5 | — | — | — | — |

TABLE 7

| | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-18 | A | 1100 | 1.97 | A | A | A | Rectangular | Rectangular |
| Example 3-19 | A | 1200 | 1.98 | A | A | A | Rectangular | Rectangular |
| Example 3-20 | A | 1000 | 1.98 | A | A | A | Rectangular | Rectangular |
| Example 3-21 | A | 900 | 1.98 | A | A | A | Rectangular | Rectangular |
| Example 3-22 | A | 1300 | 1.98 | A | A | A | Rectangular | Rectangular |
| Example 3-23 | A | 1400 | 1.98 | A | A | A | Rectangular | Rectangular |

TABLE 7-continued

| | Storage stability | Exposure sensitivity (mJ/cm²) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-24 | A | 700 | 1.96 | A | A | A | Rectangular | Rectangular |
| Example 3-25 | A | 800 | 1.98 | A | A | A | Rectangular | Rectangular |
| Example 3-26 | A | 600 | 1.98 | A | A | A | Rectangular | Rectangular |
| Example 3-27 | A | 800 | 1.98 | A | A | A | Rectangular | Rectangular |
| Example 3-28 | A | 850 | 1.98 | A | A | A | Rectangular | Rectangular |
| Example 3-29 | A | 850 | 1.98 | A | A | A | Rectangular | Rectangular |
| Example 3-30 | A | 650 | 1.98 | A | A | A | Rectangular | Rectangular |
| Example 3-31 | A | 650 | 1.98 | A | A | A | Rectangular | Rectangular |
| Example 3-32 | A | 650 | 1.98 | A | A | A | Rectangular | Rectangular |
| Example 3-33 | A | 600 | 1.98 | A | A | A | Rectangular | Rectangular |
| Example 3-34 | A | 600 | 1.98 | A | A | A | Rectangular | Rectangular |
| Comp. example 3-4 | B | 3200 | 1.92 | B | B | C | Reverse tapered | Forward tapered |
| Comp. Example 3-5 | A | 2400 | 1.92 | B | C | B | Reverse tapered | Forward tapered |
| Comp. Example 3-6 | A | 4600 | 1.92 | C | B | B | Reverse tapered | Forward tapered |

Example 3-35

The compounds of the following composition D-1 were mixed, and a colored photopolymerizable composition D-1 containing a colorant (pigment) was prepared.

<Composition D-1>

| | |
|---|---|
| Ethyl 3-ethoxypropionate (solvent) | 17.9 parts |
| Colorant (dispersion of C.I. Pigment Red 254) (solid content: 15% by mass; pigment content in solid content: 60 %) | 33.34 parts |
| Colorant (dispersion of C.I. Pigment Yellow 139) (solid content: 15% by mass; pigment content in solid content 60%) | 22.23 parts |
| Radical polymerizable monomer (polymerizable compound) (mixture of 3:7 of pentaerythritol triacrylate and dipentaerythritol hexaacrylate) | 2.5 parts |
| Specific Compound 1 (specific oxime compound) | 0.5 parts |
| Benzyl methacrylate/methacrylic acid copolymer (molar ratio = 70/30) | 2.0 parts |

Example 3-36 to Example 3-51, and Comparative Example 3-7 to Comparative Example 3-9

Colored photopolymerizable compositions D-2 to D-17, and D'-1 to D'-3 were produced respectively in the same manner as in Example 3-35, except that 0.5 parts of Specific Compound 1 (specific oxime compound) included in the composition D-1, which was used in the preparation of the colored photopolymerizable composition D-1 in Example 3-35, was replaced with the compounds and the amounts as shown in the following Table 8, respectively, and, further-more, the sensitizers and co-sensitizers, of which kinds and amounts are shown in Table 8, were added in Example 3-44 to 3-51.

Each of the obtained colored photopolymerizable compositions was evaluated in a manner similar to that in Example 3-1. The results are shown in Table 9.

TABLE 8

| | Colored polymerizable composition | Polymerization initiator | | | Sensitizer | | Co-sensitizer | |
|---|---|---|---|---|---|---|---|---|
| | | Specific compound | Comparative compound | Content (parts) | Kind | Content (parts) | Kind | Content (parts) |
| Example 3-35 | D-1 | 1 | — | 0.5 | — | — | — | — |
| Example 3-36 | D-2 | 2 | — | 0.5 | — | — | — | — |
| Example 3-37 | D-3 | 3 | — | 0.5 | — | — | — | — |
| Example 3-38 | D-4 | 4 | — | 0.5 | — | — | — | — |
| Example 3-39 | D-5 | 5 | — | 0.5 | — | — | — | — |
| Example 3-40 | D-6 | 6 | — | 0.5 | — | — | — | — |
| Example 3-41 | D-7 | 7 | — | 0.5 | — | — | — | — |
| Example 3-42 | D-8 | 8 | — | 0.5 | — | — | — | — |
| Example 3-43 | D-9 | 9 | — | 0.5 | — | — | — | — |
| Example 3-44 | D-10 | 8 | — | 0.4 | A-1 | 0.1 | — | — |
| Example 3-45 | D-11 | 8 | — | 0.4 | A-2 | 0.1 | — | — |
| Example 3-46 | D-12 | 8 | — | 0.4 | A-3 | 0.1 | — | — |
| Example 3-47 | D-13 | 8 | — | 0.4 | — | — | F1 | 0.1 |
| Example 3-48 | D-14 | 8 | — | 0.3 | A-2 | 0.1 | F1 | 0.1 |
| Example 3-49 | D-15 | 8 | — | 0.3 | A-2 | 0.1 | F2 | 0.1 |
| Example 3-50 | D-16 | 8 | — | 0.3 | A-2 | 0.1 | F3 | 0.1 |
| Example 3-51 | D-17 | 8 | — | 0.3 | — | — | F3 LD-5 | 0.1 0.1 |
| Comp. example 3-7 | D'-1 | — | 1 | 0.5 | — | — | — | — |
| Comp. Example 3-8 | D'-2 | — | 2 | 0.5 | — | — | — | — |
| Comp. Example 3-9 | D'-3 | — | 3 | 0.5 | — | — | — | — |

TABLE 9

| | Storage stability | Exposure sensitivity (mJ/cm$^2$) | Pattern size (µm) | Developability | Change in color in forced heat-aging | Adhesion to substrate | Pattern cross-sectional profile | Post-heating pattern cross-sectional profile |
|---|---|---|---|---|---|---|---|---|
| Example 3-35 | A | 1,500 | 1.96 | A | A | A | Rectangular | Rectangular |
| Example 3-36 | A | 1,400 | 1.96 | A | A | A | Rectangular | Rectangular |
| Example 3-37 | B | 1,400 | 1.96 | A | A | A | Rectangular | Rectangular |
| Example 3-38 | A | 1,200 | 1.96 | A | A | A | Rectangular | Rectangular |
| Example 3-39 | A | 1,700 | 1.96 | A | A | A | Rectangular | Rectangular |
| Example 3-40 | A | 1,900 | 1.96 | A | A | A | Rectangular | Rectangular |
| Example 3-41 | A | 900 | 1.94 | A | A | A | Rectangular | Rectangular |
| Example 3-42 | A | 900 | 1.96 | A | A | A | Rectangular | Rectangular |
| Example 3-43 | A | 900 | 1.96 | A | A | A | Rectangular | Rectangular |

TABLE 9-continued

|  | Storage stability | Exposure sensitivity (mJ/cm$^2$) | Pattern size (μm) | Developability | Change in color in forced heat-aging | Adhesion to substrate | Pattern cross-sectional profile | Post-heating pattern cross-sectional profile |
|---|---|---|---|---|---|---|---|---|
| Example 3-44 | A | 850 | 1.96 | A | A | A | Rectangular | Rectangular |
| Example 3-45 | A | 850 | 1.96 | A | A | A | Rectangular | Rectangular |
| Example 3-46 | A | 800 | 1.96 | A | A | A | Rectangular | Rectangular |
| Example 3-47 | A | 800 | 1.96 | A | A | A | Rectangular | Rectangular |
| Example 3-48 | A | 750 | 1.96 | A | A | A | Rectangular | Rectangular |
| Example 3-49 | A | 700 | 1.96 | A | A | A | Rectangular | Rectangular |
| Example 3-50 | A | 700 | 1.96 | A | A | A | Rectangular | Rectangular |
| Example 3-51 | A | 1,200 | 1.96 | A | A | A | Rectangular | Rectangular |
| Comp. example 3-7 | B | 6,000 | 1.92 | C | B | C | Reverse tapered | Forward tapered |
| Comp. Example 3-8 | A | 4,500 | 1.92 | B | C | C | Reverse tapered | Forward tapered |
| Comp. Example 3-9 | A | 7,000 | 1.92 | C | B | C | Reverse tapered | Forward tapered |

From the results of Tables 5, 7 and 9, it is understood that the colored photopolymerizable composition in each Example containing a specific oxime compound (Specific Compound 1 to Specific Compound 9) has excellent storage stability (stability with the passage of time). Further, it is understood that these colored photopolymerizable compositions have high exposure sensitivity and excellent developability when used for forming a colored pattern of a color filter, and the size of the obtained pattern is close to 2 μm that is the mask size, and further these compositions do not cause coloration due to heat-aging of the obtained colored pattern, and these compositions are excellent in any of the adhesion to the substrate, the pattern cross-sectional profile, and the post-heating pattern cross-sectional profile.

Moreover, as is apparent from Table 9, it is understood that these compositions have high exposure sensitivity, even when the content of pigment is high.

Examples 4-1 to 4-38, and Comparative Examples 4-1 to 4-12

Preparation of Black Photopolymerizable Composition

Preparation of Carbon Black Dispersion A

The following composition 1 was subjected to a high viscous dispersing processing using two rolls to obtain a dispersion. At this time, the viscosity of the dispersion was 70,000 mPa·s.

Thereafter, the following composition 2 was added to this dispersion, and the mixture was stirred under the condition of 3,000 rpm by using a homogenizer for 3 hours. The obtained mixed solution was subjected to a fine dispersion processing using a dispersing machine (trade name: DISPERMAT; manufactured by Getzmann GmbH) with 0.3 mm zirconia beads for 4 hours, thereby preparing Carbon Black Dispersion A (hereinafter, denoted as CB Dispersion A). At this time, the viscosity of the mixed solution was 37 mPa·s.

<Composition 1>

| | |
|---|---|
| Carbon black (Pigment Black 7) having an average primary particle diameter of 15 nm | 23 parts |
| 45% Solution of benzyl methacrylate/methacrylic acid copolymer (BzMA/MAA = 70/30; Mw: 30,000) in propylene glycol monomethylether acetate | 22 parts |
| SOLSPERSE 5000 (manufactured by The Lubrizol Corporation) | 1.2 parts |

<Composition 2>

| | |
|---|---|
| 45% Solution of benzyl methacrylate/methacrylic acid copolymer (BzMA/MAA = 70/30; Mw: 30,000) in propylene glycol monomethylether acetate | 22 parts |
| Propylene glycol monomethylether acetate | 200 parts |

<Preparation of Titanium Black Dispersion A>

The following composition 3 was subjected to a high viscous dispersing processing using two rolls to obtain the dispersion. At this time, the viscosity of the dispersion was 40,000 mPa·s.

Prior to the high viscous dispersing processing, kneading may be carried out using a kneader for 30 minutes.

<Composition 3>

| | |
|---|---|
| Titanium black 13M-C having an average primary particle diameter of 75 nm (Pigment Black 35; manufactured by Mitsubishi Materials Corporation) | 39 parts |
| Propylene glycol monomethylether acetate solution of benzyl (meth)acrylate/(meth)acrylic acid copolymer (molar ratio: 70/30; Mw: 30,000) | 8 parts |
| SOLSPERSE 5000 (manufactured by The Lubrizol Corporation) | 1 part |

The following component 4 was added to the obtained dispersion, and the mixture was stirred under the condition of 3,000 rpm by using a homogenizer for 3 hours. The obtained mixed solution was subjected to a dispersing processing using a dispersing machine (trade name: DISPERMAT; manufactured by Getzmann GmbH) using 0.3 mm zirconia beads for 4 hours, thereby preparing Titanium Black Dispersion A (hereinafter, denoted as TB Dispersion A).

At this time, the viscosity of the mixed solution was 7.0 mPa·s.

<Composition 4>

| | |
|---|---|
| Propylene glycol monomethylether acetate solution of copolymer of benzyl (meth)acrylate/(meth)acrylic acid (molar ratio: 70/30; Mw: 30,000) | 8 parts |
| Propylene glycol monomethylether acetate | 200 parts |

<Preparation of Black Photopolymerizable Compositions E-1 to E-18, and E'-1 to E'-6>

The components of following composition E-a were mixed using a stirrer, and the black photopolymerizable compositions E-1 to E-18 and E'-1 to E'-6 were prepared.

<Composition E-a>

| | |
|---|---|
| Methacrylate/acrylic acid copolymer (alkali-soluble resin) (copolymerization molar ratio of 75/25; weight-average molecular weight: 50000) | 1.6 parts |
| Dipentaerythritol hexaacrylate | 2.3 parts |
| Ethoxylated pentaerythritol tetraacrylate | 0.8 parts |
| CB Dispersion A or TB Dispersion A described above | 24 parts |
| Propylene glycol monomethylether acetate | 10 parts |
| Ethyl 3-ethoxypropionate | 8 parts |
| Compound shown in the following Tables 10A and 10B: specific oxime compound or comparative compound: | quantities shown in Tables 10-A and 10B |
| Co-sensitizer: F3 described above | not added or 0.1 parts |

TABLE 10A

| | Black photo-polymerizable composition | Composition | Dispersion | Polymerization initiator | | | Co-sensitizer | |
|---|---|---|---|---|---|---|---|---|
| | | | | Specific compound | Comparative compound | Content (parts by mass) | Kind | Content (parts by mass) |
| Example 4-1 | E-1 | E-a | CB Dispersion A | 1 | — | 0.8 | — | — |
| Example 4-2 | E-2 | E-a | CB Dispersion A | 2 | — | 0.8 | — | — |
| Example 4-3 | E-3 | E-a | CB Dispersion A | 3 | — | 0.8 | — | — |

TABLE 10A-continued

| Black photo-polymerizable composition | Composition | Dispersion | Polymerization initiator Specific compound | Polymerization initiator Comparative compound | Polymerization initiator Content (parts by mass) | Co-sensitizer Kind | Co-sensitizer Content (parts by mass) |
|---|---|---|---|---|---|---|---|
| Example 4-4 | E-4 | E-a | CB Dispersion A | 4 | — | 0.8 | — | — |
| Example 4-5 | E-5 | E-a | CB Dispersion A | 5 | — | 0.8 | — | — |
| Example 4-6 | E-6 | E-a | CB Dispersion A | 6 | — | 0.8 | — | — |
| Example 4-7 | E-7 | E-a | CB Dispersion A | 7 | — | 0.8 | — | — |
| Example 4-8 | E-8 | E-a | CB Dispersion A | 8 | — | 0.7 | — | — |
| Example 4-9 | E-9 | E-a | CB Dispersion A | 9 | — | 0.7 | — | — |
| Example 4-10 | E-10 | E-a | CB Dispersion A | 1 | — | 0.1 | F3 | 0.1 |
| Example 4-11 | E-11 | E-a | TB Dispersion A | 1 | — | 0.8 | — | — |
| Example 4-12 | E-22 | E-a | TB Dispersion A | 2 | — | 0.8 | — | — |
| Example 4-13 | E-13 | E-a | TB Dispersion A | 3 | — | 0.8 | — | — |
| Example 4-14 | E-14 | E-a | TB Dispersion A | 4 | — | 0.8 | — | — |
| Example 4-15 | E-15 | E-a | TB Dispersion A | 7 | — | 0.8 | — | — |
| Example 4-16 | E-16 | E-a | TB Dispersion A | 8 | — | 0.8 | — | — |
| Example 4-17 | E-17 | E-a | TB Dispersion A | 9 | — | 0.8 | — | — |
| Example 4-18 | E-18 | E-a | TB Dispersion A | 9 | — | 0.7 | F3 | 0.1 |

TABLE 10B

| Black photo-polymerizable composition | Composition | Dispersion | Polymerization initiator Specific compound | Polymerization initiator Comparative compound | Polymerization initiator Content (parts by mass) | Co-sensitizer Kind | Co-sensitizer Content (mass by parts) |
|---|---|---|---|---|---|---|---|
| Comparative Example 4-1 | E'-1 | E-a | CB Dispersion A | — | 1 | 0.8 | — | — |
| Comparative Example 4-2 | E'-2 | E-a | CB Dispersion A | — | 2 | 0.8 | — | — |
| Comparative Example 4-3 | E'-3 | E-a | CB Dispersion A | — | 3 | 0.8 | — | — |
| Comparative Example 4-4 | E'-4 | E-a | TB Dispersion A | — | 1 | 0.8 | — | — |
| Comparative Example 4-5 | E'-5 | E-a | TB Dispersion A | — | 2 | 0.8 | — | — |
| Comparative Example 4-6 | E'-6 | E-a | TB Dispersion A | — | 3 | 0.8 | — | — |

Preparation of Black Photopolymerizable Compositions E-19 to E-38, and E'-7 to E'-12

The components of following composition E-b were mixed using a stirrer, and black photopolymerizable compositions E-19 to E-38 and E'-7 to E'-12 were prepared.

<Composition E-b>

| | |
|---|---|
| Dipentaerythritol hexaacrylate | 2.3 parts |
| CB Dispersion A or TB Dispersion A described above | 24 parts |
| Propylene glycol monomethylether acetate | 10 parts |
| Ethyl 3-ethoxypropionate | 8 parts |
| Compound shown in the following Tables 11A and 11B: specific oxime compound or comparative compound: | quantities shown in Tables 11A and 11B |
| Co-sensitizer: F3 described above | not added or 0.1 parts |

TABLE 11A

| Black photo-polymerizable composition | Composition | Dispersion | Polymerization initiator Specific compound | Polymerization initiator Comparative compound | Polymerization initiator Content (parts by mass) | Co-sensitizer Kind | Co-sensitizer Content (mass by parts) |
|---|---|---|---|---|---|---|---|
| Example 4-19 | E-19 | E-b | CB Dispersion A | 1 | — | 0.8 | — | — |
| Example 4-20 | E-20 | E-b | CB Dispersion A | 2 | — | 0.8 | — | — |
| Example 4-21 | E-21 | E-b | CB Dispersion A | 3 | — | 0.8 | — | — |
| Example 4-22 | E-22 | E-b | CB Dispersion A | 4 | — | 0.8 | — | — |
| Example 4-23 | E-23 | E-b | CB Dispersion A | 5 | — | 0.8 | — | — |
| Example 4-24 | E-24 | E-b | CB Dispersion A | 6 | — | 0.8 | — | — |
| Example 4-25 | E-25 | E-b | CB Dispersion A | 7 | — | 0.8 | — | — |

TABLE 11A-continued

|  | Black photo-polymerizable composition | Composition | Dispersion | Polymerization initiator Specific compound | Polymerization initiator Comparative compound | Polymerization initiator Content (parts by mass) | Co-sensitizer Kind | Co-sensitizer Content (mass by parts) |
|---|---|---|---|---|---|---|---|---|
| Example 4-26 | E-26 | E-b | CB Dispersion A | 8 | — | 0.8 | — | — |
| Example 4-27 | E-27 | E-b | CB Dispersion A | 9 | — | 0.8 | — | — |
| Example 4-28 | E-28 | E-b | CB Dispersion A | 8 | — | 0.7 | F3 | 0.1 |
| Example 4-29 | E-29 | E-b | TB Dispersion A | 1 | — | 0.8 | — | — |
| Example 4-30 | E-30 | E-b | TB Dispersion A | 2 | — | 0.8 | — | — |
| Example 4-31 | E-31 | E-b | TB Dispersion A | 3 | — | 0.8 | — | — |
| Example 4-32 | E-32 | E-b | TB Dispersion A | 4 | — | 0.8 | — | — |
| Example 4-33 | E-33 | E-b | TB Dispersion A | 5 | — | 0.8 | — | — |
| Example 4-34 | E-34 | E-b | TB Dispersion A | 6 | — | 0.8 | — | — |
| Example 4-35 | E-35 | E-b | TB Dispersion A | 7 | — | 0.8 | — | — |

TABLE 11B

|  | Black photo-polymerizable composition | Composition | Dispersion | Polymerization initiator Specific compound | Polymerization initiator Comparative compound | Polymerization initiator Content (parts by mass) | Co-sensitizer Kind | Co-sensitizer Content (mass by parts) |
|---|---|---|---|---|---|---|---|---|
| Example 4-36 | E-36 | E-b | TB Dispersion A | 8 | — | 0.8 | — | — |
| Example 4-37 | E-37 | E-b | TB Dispersion A | 9 | — | 0.8 | — | — |
| Example 4-38 | E-38 | E-b | TB Dispersion A | 8 | — | 0.7 | F3 | 0.1 |
| Comparative Example 4-7 | E'-7 | E-b | CB Dispersion A | — | 1 | 0.8 | — | — |
| Comparative Example 4-8 | E'-8 | E-b | CB Dispersion A | — | 2 | 0.8 | — | — |
| Comparative Example 4-9 | E'-9 | E-b | CB Dispersion A | — | 3 | 0.8 | — | — |
| Comparative Example 4-10 | E'-10 | E-b | TB Dispersion A | — | 1 | 0.8 | — | — |
| Comparative Example 4-11 | E'-11 | E-b | TB Dispersion A | — | 2 | 0.8 | — | — |
| Comparative Example 4-12 | E'-12 | E-b | TB Dispersion A | — | 3 | 0.8 | — | — |

The following evaluations were performed using the black photopolymerizable compositions E-1 to E-38 and E'-1 to E'-12 obtained in the above manner. The results are collectively shown in Table 12 and Table 13.

Exposure Sensitivity Evaluation

The exposure sensitivities of the black photopolymerizable compositions E-1 to E-38 and E'-1 to E'-12 obtained in the above manner were determined and evaluated by the following methods.

Each of the black photopolymerizable compositions E-1 to E-38 and E'-1 to E'-12 was used and coated uniformly on a silicon wafer in a manner such that the number of revolutions of spin coating was adjusted so as to attain a film thickness of 1.0 μm after the heat processing, using a hot plate having a surface temperature of 120° C. for 120 seconds, thereby obtaining a coated film having a thickness of 1.0 μm.

Subsequently, the coated film was irradiated with light through a mask having a L&S (line and space) pattern of 10 nm by varying an exposure amount in the range of from 100 to 5,100 mJ/cm$^2$ in increments of 100 mJ/cm$^2$, using an i-line stepper exposure machine FPA-3000i5+ (manufactured by Canon Inc.).

After the irradiation, paddle development was performed using a 0.3% aqueous solution of tetramethyl ammonium hydroxide (TMAH) at 23° C. for 60 seconds. Thereafter, the coated wafer was rinsed with pure water using a spin shower for 20 seconds, and was further washed with pure water. Then, water droplets adhered to the board were removed with highly-cleaned air and the substrate was naturally dried, thereby obtaining a black image pattern.

Each of the colored image patterns thus obtained was evaluated by using an optical microscope in accordance with the following criteria.

Evaluation of the exposure sensitivity was performed. The exposure sensitivity was defined by the minimum exposure amount necessary to achieve 95% or more of the film thickness after development in the area irradiated with light in the exposure process, with respect to 100% of the film thickness before the exposure. This definition indicates that the sensitivity is higher as the value of exposure sensitivity is smaller.

Evaluation of Storage Stability (Stability with Passage of Time)

The storage stability (stability with the passage of time) of the black photopolymerizable compositions E-1 to E-38 and E'-1 to E'-12 obtained in the above was evaluated according the following method.

That is, after each of the colored photopolymerizable compositions E-1 to E-38 and E'-1 to E'-12 was stored for one month at room temperature, the degree of deposition of foreign matters was visually inspected and evaluated in accordance with the following evaluation criteria:

—Evaluation Criteria—

A: No deposition is recognized;

B: Deposition is slightly recognized; and

C: Deposition is recognized.

—Evaluation of Developability—

Further, each of the developability of the black photopolymerizable compositions E-1 to E-38 and E'-1 to E'-12 was evaluated in the following manner.

That is, the developability was evaluated by observing the presence of residues in the area where light was not irradiated (unexposed portion) in the exposure process. The evaluation criteria are as follows.

—Evaluation Criteria—

A: No residues in the unexposed area are recognized at all;

B: Residues in the unexposed area are slightly recognized, but are not at a level of being problematic in practical use; and C: Residues are remarkably recognized in the unexposed area.

TABLE 12

|  | Exposure sensitivity (mJ/cm$^2$) | Storage storability | Developability |
| --- | --- | --- | --- |
| Example 4-1 | 200 | A | A |
| Example 4-2 | 250 | A | A |
| Example 4-3 | 200 | A | A |
| Example 4-4 | 150 | A | A |
| Example 4-5 | 450 | A | A |
| Example 4-6 | 400 | A | A |
| Example 4-7 | 100 | A | A |
| Example 4-8 | 150 | A | A |
| Example 4-9 | 100 | A | A |
| Example 4-10 | 150 | A | A |
| Example 4-11 | 200 | A | A |
| Example 4-12 | 200 | A | A |
| Example 4-13 | 150 | A | A |
| Example 4-14 | 120 | A | A |
| Example 4-15 | 90 | A | A |
| Example 4-16 | 130 | A | A |
| Example 4-17 | 90 | A | A |
| Example 4-18 | 90 | A | A |
| Comparative Example 4-1 | 900 | B | C |
| Comparative Example 4-2 | 700 | A | C |
| Comparative Example 4-3 | 1000 | B | C |
| Comparative Example 4-4 | 800 | B | C |
| Comparative Example 4-5 | 600 | A | B |
| Comparative Example 4-6 | 900 | B | B |

TABLE 13

|  | Exposure sensitivity (mJ/cm$^2$) | Storage storability | Developability |
| --- | --- | --- | --- |
| Example 4-19 | 500 | A | A |
| Example 4-20 | 400 | A | A |
| Example 4-21 | 400 | A | A |
| Example 4-22 | 400 | A | A |
| Example 4-23 | 550 | A | A |
| Example 4-24 | 500 | A | A |
| Example 4-25 | 130 | A | A |
| Example 4-26 | 150 | A | A |
| Example 4-27 | 150 | A | A |
| Example 4-28 | 150 | A | A |
| Example 4-29 | 300 | A | A |
| Example 4-30 | 200 | A | A |
| Example 4-31 | 200 | A | A |
| Example 4-32 | 200 | A | A |
| Example 4-33 | 450 | A | A |
| Example 4-34 | 500 | A | A |
| Example 4-35 | 150 | A | A |
| Example 4-36 | 100 | A | A |
| Example 4-37 | 90 | A | A |
| Example 4-38 | 80 | A | A |
| Comparative Example 4-7 | 1200 | C | C |
| Comparative Example 4-8 | 900 | A | C |
| Comparative Example 4-9 | 1500 | B | C |
| Comparative Example 4-10 | 1000 | C | C |
| Comparative Example 4-11 | 600 | A | C |
| Comparative Example 4-12 | 800 | B | B |

As is clear from the results shown in Table 12 and Table 13, the black photopolymerizable composition in each Example containing the specific oxime compound has excellent storage stability (stability with the passage of time). Further, it is understood that these black photopolymerizable compositions have high exposure sensitivity as compared with Comparative Examples, and since these compositions have excellent developability of unexposed areas, a good black pattern (colored pattern) can be formed even if the exposure amount is small.

Example 5

Production of Full-Color Color Filter

The black image pattern produced in the above-described Example 4-1 was used as a black matrix, and a green (G) colored pattern of 1.6×1.6 μm was formed, by using the above-described colored photopolymerizable composition A-1, on the black matrix in the same manner as the method recited in Example 3-1.

Further, the colored photopolymerizable compositions of blue (B) and red (R) were prepared only by replacing the pigment (30/70 (mass ratio) mixture of C. I. Pigment Green 36 and C. I. Pigment Yellow 219) in the colored photopolymerizable composition A-1, with a blue pigment (30/70 (mass ratio) mixture of C.I. Pigment Blue 15:6 and C.I. Pigment Violet 23), and a red pigment (C.I. Pigment Red 254), respectively.

On the above-described silicon wafer substrate having a black matrix and green pixels provided thereon, a blue color (B) pattern and a red color (R) pattern each having a 1.6×1.6 μm size were sequentially formed in the same manner as in the green (G) photopolymerizable composition A-1, thereby producing a color filter for a solid-state imaging device.

Evaluation of each of the obtained color filter was performed in the same manner as that in Example 3-1 in terms of the cross-sectional profile and the adhesion to substrate of the black image pattern and each of the R, G and B colored patterns. As a result, it was found that each of the patterns had a rectangular profile, no pattern defect and excellent adhesion to substrate.

Example 6

Production of Solid-State Imaging Device

When the full-color color filter obtained in Example 5 was mounted to a solid-state imaging device, it was confirmed that the solid-state imaging device with the color filter exerts high resolution and excellent color separation property.

Examples 7-1 to 7-15, and Comparative Examples 7-1 to 7-4

Production of Support

After the surface of a 0.30 mm thick aluminum plate of 1S material grade was subjected to graining with an 800-mesh pumice stone aqueous suspension by using a nylon brush (No. 8), the surface was sufficiently washed with water. After the plate was etched by immersing it in a 10% aqueous sodium hydroxide solution at 70° C. for 60 seconds, the plate was washed with running water, followed by neutralization with 20% $HNO_3$ and washing with water. The aluminum plate was subjected to an electrolytic surface-roughening in a 1% aqueous nitric acid solution by using sine wave alternating current under the condition of VA=12.7 V with the quantity of electricity of 300 coulomb/$dm^2$ at an anode. The surface roughness measured was 0 to 45 μm (Ra expression). Subsequently, after smut was removed by immersing the aluminum plate in a 30% $H_2SO_4$ aqueous solution at 55° C. for 2 minutes, a cathode was arranged at the grained surface and the plate was subjected to anodic oxidation at a current density of 5 A/$dm^2$ for 50 seconds, in a 20% $H_2SO_4$ aqueous solution at 33° C. As a result, the thickness was 2.7 g/$m^2$.

In this way, Support A-1 for planographic printing plate precursor was obtained.

Formation of Photosensitive Layer

A coating liquid having the following composition for a photosensitive layer was coated on the obtained support so as to attain a dry coating amount of 1.4 g/$m^2$, and dried at 95° C., thereby forming a photosensitive layer.

Composition of Coating Liquid for Photosensitive Layer

| | |
|---|---|
| Addition-polymerizable compound (M, N or O shown in Table 14) | 0.80 parts |
| Binder polymer (B1, B2, or B3 shown in Table 14) | 0.90 parts |
| Sensitizer (A1, A2, or A3 shown in Table 14) | not added, or 0.10 pars |
| Compound shown in Table 8: specific oxime compound, comparative compound or LD-5 | 0.05 parts |
| Co-sensitizer (the above-described F2 or F3 recited in Table 8) | not added or 0.25 parts |
| Fluorine-containing surfactant (MEGAFAC F-177; manufactured by DIC Corporation) | 0.02 parts |
| Thermal-polymerization inhibitor (N-nitrosohydroxylamine aluminum salt) | 0.03 parts |
| ε-type copper phthalocyanine dispersion | 0.2 parts |
| Methyl ethyl ketone | 16.0 parts |
| Propylene glycol monomethylether | 16.0 parts |

—Preparation of ∈ Type Copper Phthalocyanine Dispersion—

In the preparation of pigment dispersion (P1), a pigment dispersion of C. I. Pigment Blue 15:6 was obtained in the same manner as in the preparation of P1, except that the sum of pigments C. I. Pigment Green 36 and CI. Pigment Yellow 219 each of which is a pigment, is replaced with C. I. Pigment Blue 15:6.

TABLE 14

| | | Photosensitive layer | | | | | |
|---|---|---|---|---|---|---|---|
| | Support | Specific compound or comparative compound | Addition polymerizable compound | Binder polymer | Sensitizer | Co-sensitizer | Coating amount (g/$m^2$) |
| Example 7-1 | A-1 | Specific Compound 1 | M | B1 | — | — | 1.4 |
| Example 7-2 | A-1 | Specific Compound 2 | M | B1 | — | — | 1.4 |
| Example 7-3 | A-1 | Specific Compound 3 | M | B1 | — | — | 1.4 |
| Example 7-4 | A-1 | Specific Compound 4 | M | B1 | — | — | 1.4 |
| Example 7-5 | A-1 | Specific Compound 5 | M | B1 | — | — | 1.4 |
| Example 7-6 | A-1 | Specific Compound 6 | M | B1 | — | — | 1.4 |
| Example 7-7 | A-1 | Specific Compound 7 | M | B1 | — | — | 1.4 |
| Example 7-8 | A-1 | Specific Compound 8 | M | B1 | — | — | 1.4 |
| Example 7-9 | A-1 | Specific Compound 9 | M | B1 | — | — | 1.4 |
| Example 7-10 | A-1 | Specific Compound 2 | M | B1 | A1 | F2 | 1.4 |
| Example 7-11 | A-1 | Specific Compound 2 | N | B2 | A1 | F2 | 1.4 |
| Example 7-12 | A-1 | Specific Compound 2 | O | B3 | A1 | F2 | 1.4 |

TABLE 14-continued

| | Support | Specific compound or comparative compound | Addition polymerizable compound | Binder polymer | Sensitizer | Co-sensitizer | Coating amount (g/m$^2$) |
|---|---|---|---|---|---|---|---|
| Example 7-13 | A-1 | Specific Compound 2 | O | B3 | A2 | F2 | 1.4 |
| Example 7-14 | A-1 | Specific Compound 2 | O | B3 | A3 | F3 | 1.4 |
| Example 7-15 | A-1 | Specific Compound 2 | O | B3 | A3 | F3 | 1.4 |
| Comparative Example 7-1 | A-1 | Comparative Compound 1 | M | B1 | — | — | 1.4 |
| Comparative Example 7-2 | A-1 | Comparative Compound 2 | M | B1 | — | — | 1.4 |
| Comparative Example 7-3 | A-1 | Comparative Compound 3 | M | B1 | — | — | 1.4 |
| Comparative Example 7-4 | A-1 | LD-5 | M | B1 | A1 | F2 | 1.4 |

In Table 14, the details of M, N and O in the column of "addition-polymerizable compound" and B1, B2 and B3 in the column of "binder polymer" are as follows. B3 described below is a polymer (weight-average molecular weight: 70000) obtained by polymerizing a mixture of MDI and HMDI (mixing molar ratio: 80/20) and a mixture of DMPA and PPG (m=3) and TEG each of which has the following structure (mixing molar ratio: 52/22/26) in equimolar amount (average).

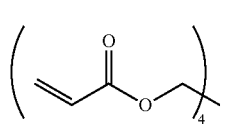

M

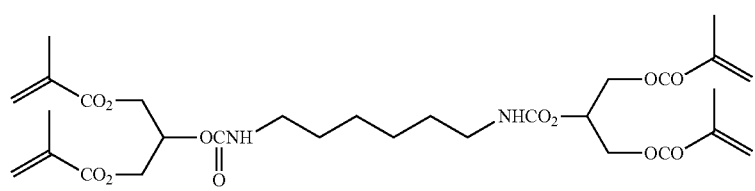

N

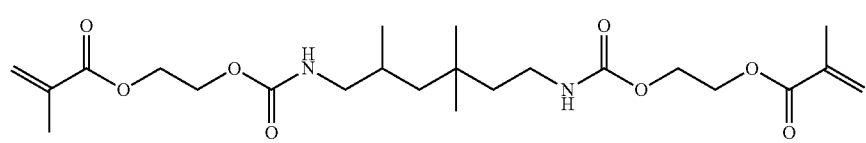

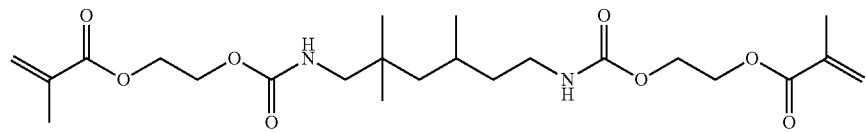

Isomer Mixture

O

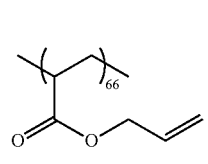 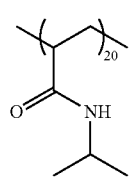 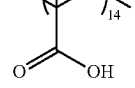

B1

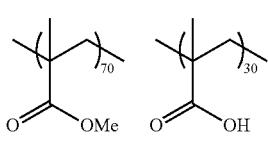

B2

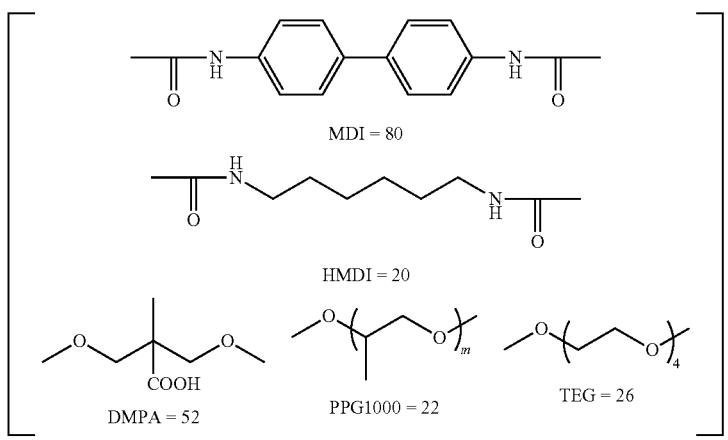

<Formation of Protective Layer>

A 3% aqueous solution of a polyvinyl alcohol (saponification degree of 98% by mol and polymerization degree of 550) was coated on the obtained photosensitive layer so as to attain a dry coating amount of 2 g/m², and dried at 100° C. for 2 minutes thereby forming a protective layer.

In this way, planographic printing plate precursors of Examples and planographic printing plate precursors of Comparative Examples were obtained.

Plate-Making

The planographic printing plate precursors were subjected to the following exposure and development processing.

Exposure

Solid images and 1- to 99-% dot images (in increments of 1%) were formed by scan-exposing the planographic printing plate precursor with an exposure amount of 50 µJ/cm² using a violet LD (VIOLET BOXER manufactured by FFEI Ltd.) at a wavelength of 405 nm, under the conditions of 4,000 dpi and 175 lines/inch.

Development

The planographic printing plate precursor was subjected to a standard processing by using an automatic developing machine (LP-850P2; manufactured by FujiFilm Corporation), in which the following developer 1 and a finishing gum liquid "PF-2W" (manufactured by FujiFilm Corporation) were placed. The condition of preheating was the achieving temperature to the plate surface of 100° C., the temperature of developer was 30° C., and the immersion time in the developer was about 15 seconds.

The developer 1 has the following composition, pH was 11.5 at 25° C., and the electroconductivity was 5 mS/cm.

—Composition of Developer 1—

| Potassium hydroxide | 0.15 g |
| Polyoxyethylene phenyl ether (n = 13) | 5.0 g |
| CHELEST 400 (chelating agent) | 0.1 g |
| Water | 94.75 g |

Evaluation

The sensitivity, the storage stability, and the printing durability of the formed image areas of Examples and Comparative Examples were evaluated in the following methods. The results are collectively shown in Table 8.

(1) Evaluation of Sensitivity

The planographic printing plate precursor was exposed to light under the above conditions, and was developed under the above conditions immediately after the light exposure, thereby forming an image. The percentage of area of 50% halftone dots of the formed image was measured using a dot meter (manufactured by Gretag/Macbeth). This shows that the sensitivity is higher as the numeral value increases.

(2) Test for Printing Durability of Image Area

Printing with the use of the planographic printing plate precursor was performed using "R201" manufactured by Roland as a printing machine, and "GEOS-G(N)" manufactured by DIC Corporation, as an ink. By observing the printed matter on which a solid image area was printed, the printing durability was evaluated based on the number of printed sheets when faint printing of images begins to take place. This shows that the printing durability is higher as the numeral value becomes larger.

(3) Evaluation of the Amount of Change in Forced Aging (Storage Stability)

The measurement of the halftone dot area was carried out in a manner similar to the evaluation of the sensitivity, except that the planographic printing plate precursors, which were sealed together with interleaf paper in aluminum kraft paper and allowed to stand at 60° C. for 4 days, were used. Next, the difference in halftone dot area between the printing plate, which was allowed to stand at 60° C. for 4 days and the printing plate which was not allowed to stand at 60° C. for 4 days, was obtained, and the variation in the dot percentage (A %) due to the forced aging was measured. This shows that the smaller the absolute numeral value, the less the variation in dot is affected by the forced aging, namely, the storage stability is high.

TABLE 15

| | Sensitivity (%) (Area of 50% halftone dot) | Variation in forced aging | Image area print durability test |
|---|---|---|---|
| Example 7-1 | 56 | 2.0 | 70000 |
| Example 7-2 | 56 | 2.0 | 70000 |
| Example 7-3 | 56 | 2.0 | 60000 |
| Example 7-4 | 60 | 2.0 | 100000 |
| Example 7-5 | 52 | 2.0 | 40000 |
| Example 7-6 | 52 | 2.0 | 40000 |

TABLE 15-continued

| | Sensitivity (%) (Area of 50% halftone dot) | Variation in forced aging | Image area print durability test |
|---|---|---|---|
| Example 7-7 | 65 | 2.0 | 100000 |
| Example 7-8 | 67 | 2.0 | 120000 |
| Example 7-9 | 69 | 2.0 | 120000 |
| Example 7-10 | 57 | 2.0 | 70000 |
| Example 7-11 | 57 | 2.0 | 70000 |
| Example 7-12 | 59 | 2.0 | 100000 |
| Example 7-13 | 60 | 2.0 | 100000 |
| Example 7-14 | 62 | 2.0 | 100000 |
| Example 7-15 | 65 | 2.0 | 100000 |
| Comparative Example 7-1 | 45 | 2.0 | 1000 |
| Comparative Example 7-2 | 47 | 2.0 | 5000 |
| Comparative Example 7-3 | 40 | 2.0 | 2000 |
| Comparative Example 7-4 | 48 | 2.0 | 10000 |

As is apparent from Table 15, it is understood that the planographic printing plate precursors of Examples 7-1 to 7-15, whose photosensitive layers each contain the specific oxime compound, according to the invention each have highly sensitive, excellent storage stability and excellent printing durability.

On the other hand, the planographic printing plate precursors used in Comparative Examples 7-1 to 7-4 are inferior to the planographic printing plate precursors used in Examples in terms of both the sensitivity and the printing durability.

The invention claimed is:

1. A photopolymerizable composition comprising: a photopolymerization initiator (A) having a partial structure represented by the following Formula (1); and a polymerizable compound (B):

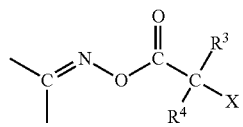
(1)

wherein, in Formula (1), $R^3$ and $R^4$ each independently represent a hydrogen atom, an alkyl group, an alkenyl group, an alkynyl group, an aryl group, a heteroaryl group or an alkoxy group; $R^3$ and $R^4$ may bind to one another to form a ring; X represents $OR^5$, $SR^6$ or $NR^{17}R^{18}$, wherein $R^5$, $R^6$, $R^{17}$ and $R^{18}$ each independently represent a hydrogen atom, an alkyl group, an alkenyl group, an alkynyl group, an aryl group or a heteroaryl group; and $R^{17}$ and $R^{18}$ may bind to one another to directly form a ring, or form a ring via a divalent linking group, wherein the photopolymerization initiator having the partial structure represented by Formula (1) comprises a compound represented by the following Formula (2):

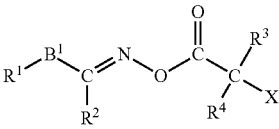
(2)

wherein, in Formula (2), $R^1$ and $R^2$ each independently represents a hydrogen atom, an alkyl group, an alkenyl group, an alkynyl group, an aryl group or a heteroaryl group; $R^1$ and $R^2$ may bind to one another to form a ring; $B^1$ represents a carbonyl group; and $R^3$, $R^4$ and X have the same definition as $R^3$, $R^4$ and X in Formula (1), respectively.

2. The photopolymerizable composition according to claim 1, wherein the photopolymerization initiator having a partial structure represented by Formula (1) comprises a compound represented by the following Formula (3):

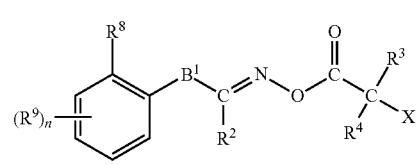
(3)

wherein, in Formula (3), $B^1$, X, $R^2$, $R^3$ and $R^4$ have the same definition as $B^1$, X, $R^2$, $R^3$ and $R^4$ in Formula (2), respectively; $R^8$ represents a hydrogen atom, an alkyl group, an alkoxy group or an alkylthio group; $R^8$ may bind to $R^2$ via a divalent linking group to form a ring structure; $R^9$ represents an alkyl group, an alkenyl group, an aryl group, a heteroaryl group, an alkoxy group, an aryloxy group, an alkylthio group, an arylthio group, an amino group, an arylcarbonyl group, a heteroarylcarbonyl group or a halogen atom; when there is more than one $R^9$, respective $R^9$s may bind to one another via a divalent linking group; n represents an integer of 0 to 2; and when n is 2, respective $R^9$s may be the same as or different from each other.

3. The photopolymerizable composition according to claim 1, further comprising a coloring agent (C).

4. The photopolymerizable composition according to claim 3, which is used for forming a colored area of a color filter.

5. A photopolymerizable composition comprising: a photopolymerization initiator (A) having a partial structure represented by the following Formula (1); and a polymerizable compound (B):

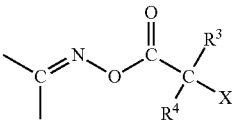
(1)

wherein, in Formula (1), $R^3$ and $R^4$ each independently represents a hydrogen atom, an alkyl group, an alkenyl group, an alkynyl group, an aryl group, a heteroaryl group or an alkoxy group; $R^3$ and $R^4$ may bind to one another to form a ring; X represents $OR^5$, $SR^6$ or $NR^{17}R^{18}$, wherein $R^5$, $R^6$, $R^{17}$ and $R^{18}$ each independently represents a hydrogen atom, an alkyl group, an alkenyl group, an alkynyl group, an aryl group or a heteroaryl group; and $R^{17}$ and $R^{18}$ may bind to one another to directly form a ring, or form a ring via a divalent linking group, wherein the photopolymerization initiator having the partial structure represented by Formula (1) comprises a compound represented by the following Formula (2):

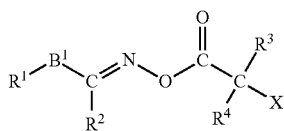

(2)

wherein, in Formula (2), $R^1$ and $R^2$ each independently represents a hydrogen atom, an alkyl group, an alkenyl group, an alkynyl group, an aryl group or a heteroaryl group; $R^1$ and $R^2$ may bind to one another to form a ring; $B^1$ represents a single bond or a carbonyl group; and $R^3$ and $R^4$ have the same definition as $R^3$ and $R^4$ in Formula (1), respectively, and X represents $NR^{17}R^{18}$, wherein $R^{17}$ and $R^{18}$ have the same definition as $R^{17}$ and $R^{18}$ in Formula (1), respectively.

6. The photopolymerizable composition according to claim 5, wherein the photopolymerization initiator having a partial structure represented by Formula (1) comprises a compound represented by the following Formula (3):

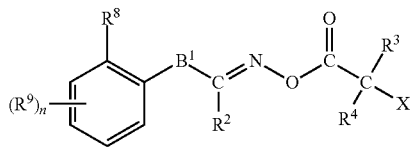

(3)

wherein, in Formula (3), $B^1$, X, $R^2$, $R^3$ and $R^4$ have the same definition as $B^1$, X, $R^2$, $R^3$ and $R^4$ in Formula (2), respectively; $R^8$ represents a hydrogen atom, an alkyl group, an alkoxy group or an alkylthio group; $R^8$ may bind to $R^2$ via a divalent linking group to form a ring structure; $R^9$ represents an alkyl group, an alkenyl group, an aryl group, a heteroaryl group, an alkoxy group, an aryloxy group, an alkylthio group, an arylthio group, an amino group, an arylcarbonyl group, a heteroarylcarbonyl group or a halogen atom; when there is more than one $R^9$, respective $R^9$s may bind to one another via a divalent linking group; n represents an integer of 0 to 2; and when n is 2, respective $R^9$s may be the same as or different from each other.

7. The photopolymerizable composition according to claim 5, wherein the photopolymerization initiator having a partial structure represented by Formula (1) comprises a compound represented by the following Formula (6):

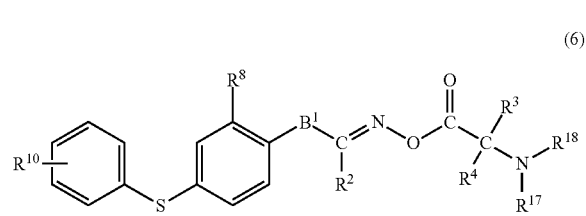

(6)

wherein, in Formula (6), $R^3$, $R^4$, $R^{17}$ and $R^{18}$ have the same definition as $R^3$, $R^4$, $R^{17}$ and $R^{18}$ in Formula (1), respectively; $B^1$ and $R^2$ have the same definition as $B^1$ and $R^2$ in Formula (2), respectively; $R^8$ has the same definition as $R^8$ in Formula (3); and $R^{10}$ has the same definition as $R^{10}$ in Formula (4).

8. The photopolymerizable composition according to claim 5, further comprising a coloring agent (C).

9. The photopolymerizable composition according to claim 8, wherein the coloring agent (C) comprises a pigment, and the photopolymerizable composition further comprises a pigment dispersing agent (D).

10. The photopolymerizable composition according to claim 8, wherein the coloring agent (C) comprises a black coloring agent.

11. The photopolymerizable composition according to claim 8, which is used for forming a colored area of a color filter.

* * * * *